United States Patent [19]

Theobald et al.

[11] Patent Number: 4,943,584
[45] Date of Patent: Jul. 24, 1990

[54] (P-PHENOXYPHENOXY)-METHYL-FIVE-MEMBERED HETARYLS

[75] Inventors: Hans Theobald, Limburgerhof; Christoph Kuenast, Otterstadt; Peter Hofmeister, Neustadt; Hans-Juergen Neubauer, Mannheim; Thomas Kuekenhoehner, Frankenthal; Wolfgang Krieg, Weingarten; Joachim Leyendecker, Mannheim; Uwe Kardorff, Frankenthal, all of Fed. Rep. of Germany

[73] Assignee: BASF Aktiengesellschaft, Ludwigshafen, Fed. Rep. of Germany

[21] Appl. No.: 184,122

[22] Filed: Apr. 20, 1988

[30] Foreign Application Priority Data

Apr. 21, 1987 [DE] Fed. Rep. of Germany ....... 3713337
Feb. 8, 1988 [DE] Fed. Rep. of Germany ....... 3803703

[51] Int. Cl.$^5$ .................... A01N 43/80; A01N 43/76; C07D 261/08; C07D 261/12
[52] U.S. Cl. .................... 514/380; 514/361; 514/363; 514/364; 514/365; 514/369; 514/372; 514/374; 514/376; 514/378; 514/383; 514/384; 514/396; 514/398; 514/406; 514/407; 514/427; 514/438; 514/445; 514/461; 514/473; 548/128; 548/129; 548/131; 548/132; 548/136; 548/143; 548/144; 548/182; 548/183; 548/186; 548/203; 548/206; 548/213; 548/225; 548/226; 548/227; 548/228; 548/229; 548/230; 548/231; 548/232; 548/235; 548/236; 548/243; 548/247; 548/262; 548/263; 548/337; 548/342; 548/375; 548/376; 548/377; 548/378; 548/541; 548/543; 548/547; 548/551; 549/66; 549/78; 549/475; 549/476
[58] Field of Search .................... 548/243, 247; 71/88; 514/378, 380

[56] References Cited

U.S. PATENT DOCUMENTS

| 3,987,102 | 10/1976 | Karrer | 568/331 |
| 4,061,683 | 12/1977 | Karrer | 568/636 |
| 4,069,344 | 1/1978 | Karrer | 514/622 |
| 4,094,989 | 6/1978 | Karrer | 514/466 |
| 4,123,556 | 10/1978 | Karrer | 514/719 |
| 4,153,731 | 5/1979 | Karrer | 514/713 |
| 4,172,146 | 10/1979 | Karrer | 514/543 |
| 4,227,914 | 10/1980 | Föry et al. | 71/88 |
| 4,254,262 | 3/1981 | Koike et al. | 546/287 |
| 4,268,678 | 5/1981 | Diana et al. | 548/247 |
| 4,447,259 | 5/1984 | Ohyama et al. | 71/94 |
| 4,451,476 | 5/1984 | Diana | 514/378 |
| 4,722,934 | 2/1988 | Matsumoto et al. | 514/363 |

FOREIGN PATENT DOCUMENTS 2516331 11/1975 Fed. Rep. of Germany .

OTHER PUBLICATIONS

Derwent Abstract for JP55/124460 (9/25/80).
Derwent Abstract for JP57/175177 (10/28/82).
Derwent Abstract for JP 57/175179 (10/28/82).

Primary Examiner—Mukund J. Shah
Assistant Examiner—F. Bernhardt
Attorney, Agent, or Firm—Keil & Weinkauf

[57] ABSTRACT

Novel (p-phenoxyphenoxy)-methyl-five-membered heeroaromatic radicals of the formula

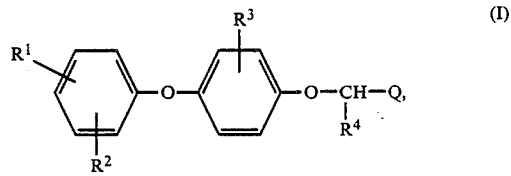

where the substituents have the following meanings:
$R^1$, $R^2$, $R^3$ hydrogen, halogen, $C_1$-$C_8$-alkyl, $C_1$-$C_8$-alkoxy, $C_1$-$C_4$-haloalkyl, $C_1$-$C_4$-haloalkoxy, $C_3$-$C_{10}$-cycloalkyl, nitro or cyano,
$R^4$ hydrogen or $C_1$-$C_4$-alkyl, and a five-membered heteroaromatic ring, and their use for combating pests.

6 Claims, No Drawings

(P-PHENOXYPHENOXY)-METHYL-FIVE-MEMBERED HETARYLS

The present invention relates to novel (p-phenoxyphenoxy)-methyl-fivemembered heteroaromatics of the general formula I

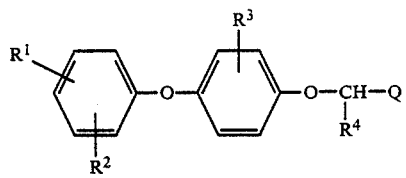
(I)

where the substituents have the following meanings: $R^1$, $R^2$ and $R^3$ are hydrogen, halogen, $C_1$–$C_8$-alkyl, $C_1$–$C_8$-alkoxy, $C_1$–$C_4$-haloalkyl, $C_1$–$C_4$-haloalkoxy, $C_3$–$C_{10}$-cycloalkyl, nitro or cyano, $R_4$ is hydrogen or $C_1$–$C_4$-alkyl and Q is a fivemembered hetaryl radical of the formulae II.1 to II.33

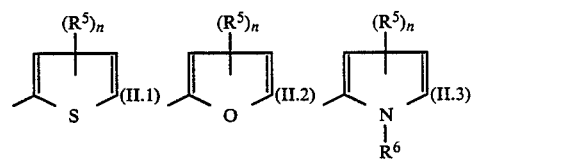

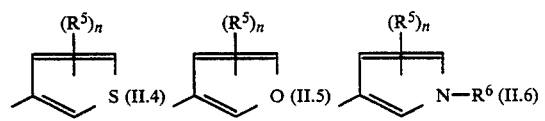

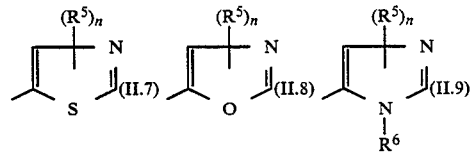

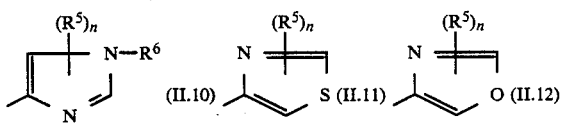

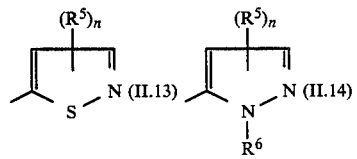

-continued

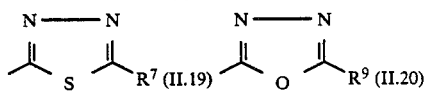

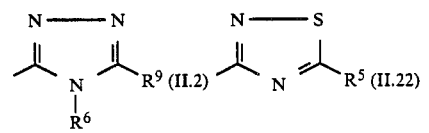

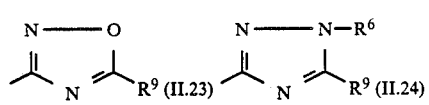

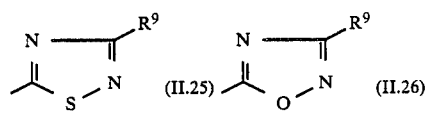

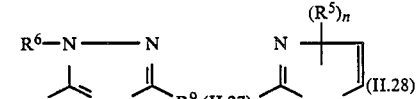

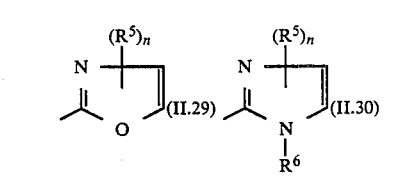

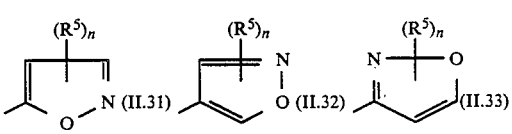

where $R^5$ is halogen, $C_1$–$C_8$-alkyl, $C_2$–$C_8$-alkenyl, $C_1$–$C_4$-haloalkyl, $C_1$–$C_8$-alkoxy, $C_2$–$C_8$-alkoxyalkyl, $C_3$–$C_{10}$-cycloalkyl, aryl or $C_7$–$C_{20}$-arylalkyl, the aryl and $C_7$–$C_{20}$-arylalkyl being unsubstituted or monosubstituted, disubstituted or trisubstituted in the aryl moiety by halogen, $C_1$–$C_8$-alkyl, $C_1$–$C_8$-alkoxy, $C_1$–$C_4$-haloalkyl or $C_1$–$C_4$-haloalkoxy or cyano or monosubstituted or disubstituted by nitro, $R^6$ is hydrogen, $C_1$–$C_8$-alkyl, $C_3$–$C_{10}$-cycloalkyl or aryl, which is unsubstituted or monosubstituted, disubstituted or trisubstituted by halogen, $C_1$–$C_6$-alkyl, $C_1$–$C_8$-alkoxy, $C_1$–$C_4$-haloalkyl or $C_1$–$C_3$-haloalkoxy, $R^7$ is hydrogen or $C_3$–$C_{10}$-cycloalkyl, $R^9$ is hydrogen or $R^5$ and n is 0 (unsubstituted heterocyclic ring), 1, or, where relevant, 2 or 3, with the proviso that $R^4$ is not methyl if Q is the fivemembered hetaryl radical II.26.

The invention further relates to pesticides which contain the compounds I as active ingredients, and to a method for control of pests.

DE-C-2,304,962, DE-B-2,322,853, DE-C-2,418,295, DE-A-2,942,989 and JP 80/124,460 disclose numerous p-phenoxyphenoxy compounds, but these do not contain an alkyl-isoxazole radical. The action of these compounds leaves something to be desired.

(p-Phenoxyphenoxy)-methylpyridine derivatives and (p-phenoxyphenoxy)-methylthiadiazolyl derivatives possessing insecticidal action are known from DE-A-2,516,331 and EP-A-239,047. Further, JP 57/175,179 and JP 57/175,177 recommend (p-phenoxyphenoxy)- methyl-1,2,4-oxadiazol-5-yl derivatives as herbicidal active ingredients.

It is an object of the present invention to provide novel (p-phenoxyphenoxy)-methyl heteroaromatics having improved insecticidal action.

We have found that this object is achieved by the novel (p-phenoxyphenoxy)-methyl-fivemembered heteroaromatics defined at the outset. A process for their preparation has also been found. Further, we have found that the compounds I are outstandingly suitable for control of pests.

The compounds I are obtainable by the following methods:

(a) A (p-phenoxy)-phenol III and a fivemembered hetaryl derivative IV are reacted in the presence of a base at from −20° to 250° C., preferably from 20° to 120° C., in accordance with the following equation:

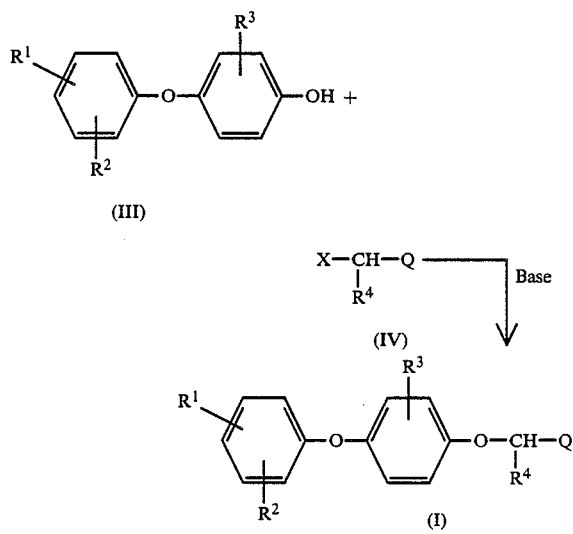

The (p-phenoxy)-phenols III are either known from Houben/Weyl, volume VI, 3, Methoden der org. Chemie, Thieme Verlag, 1965, 585 et seq., or can be prepared by the methods described there.

The hetaryl derivatives IV are either known and, in some cases, commercially available or can be prepared by generally known chemical processes. For example, processes for the preparation of thiophene derivatives (Q=II.1, II.4) may be found in Comprehensive Heterocyclic Chemistry, R. Katritzky and W. Rees, vol. 4, p. 863 et seq., Pergamon Press 1984; processes for the preparation of furan derivatives (Q=II.2, II.5) is, for example, DE-A-3,514,384, DE-A-3,546,371 or Advances in Heterocyclic Chemistry, vol. 30 (1982), p. 167 et seq.; processes for the preparation of pyrrole derivatives (Q=II.3, II.6) in, for example, Comprehensive Heterocyclic Chemistry, R. Katritzky and W. Rees, vol. 4, p. 201 et seq., Pergamon Press, 1984; processes for the preparation of thiazole derivatives (Q=II.7, II.11, II.28), oxazole derivatives (Q=II.8, II.12, II.29), isothiazole derivatives (Q=II.13, II.16, II.18), thiadiazole derivatives (Q=II.19, II.22, II.25) and oxadiazole derivatives (Q=II.20, II.23, II.26) in, for example, Comprehensive Heterocyclic Chemistry, R. Katritzky and W. Rees, vol. 6, p. 166, 177, 235, 386, 425 et seq., Pergamon Press, 1984; processes for the preparation of imidazole derivatives (Q=II.9, II.10, II.30) in, for example, Advances in Heterocyclic Chemistry, vol. 27 (1980), p. 242 et seq.; processes for the preparation of pyrazole derivatives (Q=II.14, II.15, II.17) in, for example, Heteroaromatic Nitrogen Compounds, The Azoles, p. 31 et seq., Cambridge University Press, 1976; processes for the preparation of triazole derivatives (Q=II.21, II.24, II.27) in, for example, Comprehensive Heterocyclic Chemistry, R. Katritzky and W. Rees, vol. 5, p. 733 et seq., Pergamon Press, 1984; and processes for the preparation of isoxazole derivatives (Q=II.31, II.32, II.33) in, for example, DE-A-2,549,962 and DE-A-2,754,832.

Normally the amount of base added to III and/or to IV is at least equivalent to III but the base can also be used in excess or, where appropriate, as a solvent. Examples of suitable bases are alkali metal and alkaline earth metal hydroxides, such as sodium hydroxide, potassium hydroxide and calcium hydroxide; alkali metal and alkaline earth metal alcoholates, such as sodium methylate, sodium ethylate, calcium methylate or potassium tert.butylate; alkali metal or alkaline earth metal hydrides such as sodium hydride, potassium hydride or calcium hydride; alkali metal or alkaline earth metal carbonates such as sodium carbonate, potassium carbonate or calcium carbonate; aliphatic amines such as dimethylamine, triethylamine or diisopropylamine; heterocyclic amines such as piperidine, piperazine or pyrrolidine; aromatic amines, such as pyridine or pyrrole and, where appropriate, also alkyl-lithium compounds such as n-butyl-lithium.

The reaction is advantageously carried out in a solvent or diluent. Examples of suitable solvents or diluents are aliphatic hydrocarbons, such as n-pentane, n-hexane, a hexane isomer mixture and naphtha; aromatic hydrocarbons, such as benzene, toluene, the xylenes and their isomer mixtures; gasoline; alcohols, such as methanol, ethanol, n-propanol and isopropanol; ethers, such as diethyl ether, di-n-butyl ether, methyl tert.-butyl ether, tetrahydrofuran and dioxane; ketones, such as acetone, methyl ethyl ketone and methyl isopropyl ketone; nitriles, such as acetonitrile and propionitrile; and aprotic dipolar solvents such as dimethylformamide, dimethyl sulfoxide or pyridine. Mixtures of these substances may also be used as solvents and diluents.

(b) A phenolate anion of III and a fivemembered hetaryl derivative IV are reacted at from −20° to 120° C., preferably from −20° to 80° C., in accordance with the following equation:

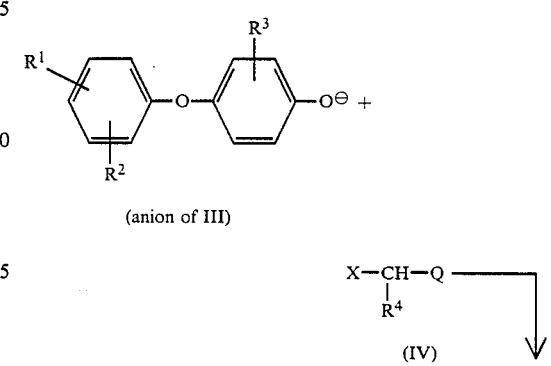

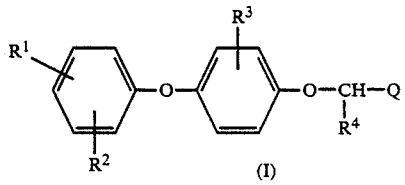

Normally, equimolar amounts of III and IV are used, but an excess of one or other component can also be employed.

The anions of the (p-phenoxy)-phenols III are known in the form of their metal salts, such as the sodium salt or potassium salt, or may be generated in situ from the phenols III known from Houben/Weyl (loc. cit.) or from phenols III which may be prepared by the methods described therein, by reaction with normal metallizing reagents such as sodium methylate, sodium ethylate, potassium tert.-butylate, sodium hydride, potassium hydride or n-butyllithium.

The reaction is advantageously carried out in a solvent or diluent. Examples of suitable solvents or diluents are aliphatic hydrocarbons, such as n-pentane, n-hexane, a hexane isomer mixture and naphtha; halohydrocarbons, such as chlorobenzene, methylene chloride, ethylene chloride, chloroform aand tetrachloroethylene; aromatic hydrocarbons, such as benzene, toluene, the xylenes and their isomer mixtures; gasoline; ethers, such as diethyl ether, di-n-butyl ether, methyl tert.-butyl ether, tetrahydrofuran and dioxane; ketones, such as acetone, methyl ethyl ketone and methyl isopropyl ketone; and aprotic dipolar solvents such as dimethylformamide, dimethyl sulfoxide or pyridine. Mixtures of these substances may also be used as solvents and diluents.

In both cases, the radical X is a leaving group, for example a sulfonic acid radical or a halogen. Among sulfonic acid radicals, methanesulfonyl, trifluoromethanesulfonyl and p-toluenesulfonyl are preferred, while among halogens, chlorine and bromine are preferred, the former particularly so.

To prepare the compounds I according to the invention by the methods described above, the starting materials are usually employed in the stoichiometric ratio. However, in particular cases an excess of one or other starting material may be entirely advantageous.

The reactions usually take place at adequate velocity above $-20°$ C. $120°$ C. should in general not be exceeded. Since the reactions are in some cases exothermic, it can be advantageous to provide means of cooling.

The reaction mixtures are worked up in a conventional manner, for example by adding water, separating the phases and employing column chromatography. Some of the novel compounds of the formula I are obtained as colorless or as slightly brownish viscous oils which can be freed from the last volatile constituents by prolonged heating at a moderately elevated temperature under reduced pressure (incipient distillation), and can thus be purified. If the compounds of the formula I are obtained in crystalline form, they may be purified by recrystallization.

In formula I, the substituents and the index specifically have the following meanings:

$R^1$ is hydrogen,
halogen, preferably fluorine, chlorine and bromine, the meta-position of these being particularly preferred,
linear or branched $C_1-C_8$-alkyl, preferably linear or branched $C_1-C_6$-alkyl, and more especially linear or branched $C_1-C_4$-alkyl in the meta-position, such as m-methyl, m-ethyl, m-(n-propyl), m-(iso-propyl), m-(n-butyl), m-(iso-butyl), m-(sec.-butyl) and m-(tert.-butyl),
linear or branched $C_1-C_8$-alkoxy, preferably linear or branched $C_1-C_4$-alkoxy, more especially $C_1-C_2$-alkoxy in the meta-position, such as m-methoxy and m-ethoxy,
linear or branched $C_1-C_4$-haloalkyl, preferably $C_1-C_2$-fluoroalkyl and -chloroalkyl, more especially m-trifluoromethyl and m-trichloromethyl,
linear or branched $C_1-C_4$-haloalkoxy, preferably $C_1-C_2$-fluoroalkoxy and -chloroalkoxy, more especially m-trifluoromethoxy and m-trichloromethoxy,
$C_3-C_{10}$-cycloalkyl, preferably $C_3-C_6$-cycloalkyl, more especially m-cyclopropyl, m-cyclobutyl, m-cyclopentyl and m-cyclohexyl,
nitro and
cyano,
$R^2$ and $R^3$ are, independently of one another,
hydrogen,
halogen, preferably fluorine and chlorine,
linear or branched $C_1-C_8$-alkyl, preferably linear or branched $C_1-C_4$-alkyl, more especially $C_1-C_2$-alkyl, such as methyl and ethyl,
linear or branched $C_1-C_8$-alkoxy, preferably linear or branched $C_1-C_4$-alkoxy, more especially $C_1-C_2$-alkoxy, such as methoxy and ethoxy,
linear or branched $C_1-C_4$-haloalkyl, preferably $C_1-C_2$-fluoroalkyl and -chloroalkyl, more especially trifluoromethyl and trichloromethyl,
linear or branched $C_1-C_4$-haloalkoxy, preferably $C_1-C_2$-fluoroalkoxy and -chloroalkoxy, more especially trifluoromethoxy and trichloromethoxy,
$C_3-C_{10}$-cycloalkyl, preferably $C_3-C_6$-cycloalkyl, such as cyclopropyl, cyclobutyl, cyclopentyl and cyclohexyl, more especially cyclopropyl,
nitro and
cyano.
$R^4$ is hydrogen, $C_1-C_4$-alkyl, such as methyl, ethyl, n-propyl, isopropyl, n-butyl, isobutyl, sec.-butyl and tert.-butyl, preferably methyl and ethyl, more especially methyl,
$R^5$ is halogen, preferably fluorine, chlorine and bromine,
linear or branched $C_1-C_8$-alkyl, preferably linear or branched $C_1-C_4$-alkyl, such as methyl, ethyl, n-propyl, isobutyl, sec.-butyl and tert.-butyl, preferably methyl and ethyl, n-propyl, isopropyl and tert.-butyl, more especially metthyl, ethyl, isopropyl and tert.-butyl,
$C_2-C_8$-alkenyl, preferably $C_2-C_4$-alkenyl, more especially vinyl, methylvinyl and 2,2-dimethylvinyl,
linear or branched $C_1-C_4$-haloalkyl, preferably $C_1-C_2$-fluoroalkyl and -chloroalkyl, more especially trifluoromethyl and trichloromethyl,
linear or branched $C_1-C_8$-alkoxy, preferably linear or branched $C_1-C_4$-alkoxy, more especially linear or branched $C_1-C_3$-alkoxy, such as methoxy, ethoxy, n-propoxy and isopropoxy,
$C_2-C_8$-alkoxyalkyl, preferably $C_2-C_4$-alkoxyalkyl, such as 3-(methoxymethyl), 3-(methoxy-2-ethyl), 3-(methoxymethyl) and isopropoxymethyl, $C_3$-$C_{10}$-cycloalkyl, preferably $C_3$-$C_6$-cycloalkyl, such as cyclopropyl, cyclobutyl, cyclopentyl and cyclohexyl, more especially cyclopropyl, aryl, preferably phenyl, 1-naphthyl and 2-naphthyl, more especially phenyl, $C_7$-$C_{20}$-arylalkyl, preferably $C_7$-$C_{10}$-phenylalkyl, such as benzyl and phenethyl, aryl monosubstituted, disubstituted or trisubstituted by halogen, preferably phenyl monosubstituted by fluorine or chlorine, such as 2-fluorophenyl, 3-fluorophenyl, 4-fluorophenyl, 2-chlorophenyl, 3-chlorophenyl and 4-chlorophenyl, aryl monosubstituted, disubstituted or trisubstituted by linear or branched $C_1$-$C_8$-alkyl, preferably phenyl monosubstituted by linear or branched $C_1$-$C_4$-alkyl, more especially phenyl monosubstituted by $C_1$-$C_2$-alkyl, such as 4-methylphenyl and 4-ethylphenyl, aryl monosubstituted, disubstituted or trisubstituted by linear or branched $C_1$-$C_8$-alkoxy, preferably phenyl monosubstituted by linear or branched $C_1$-$C_4$-alkoxy, more especially phenyl monosubstituted by $C_1$-$C_2$-alkoxy, such as 4-methoxyphenyl and 4-ethoxyphenyl, aryl monosubstituted, disubstituted or trisubstituted by linear or branched $C_1$-$C_4$-haloalkyl, preferably phenyl monosubstituted by $C_1$-$C_2$-fluoroalkyl and -chloroalkyl, more especially phenyl monosubstituted by trifluoromethyl and trichloromethyl, such as 4-trifluoromethylphenyl and 4-trichloromethylphenyl, aryl monosubstituted, disubstituted or trisubstituted by linear or branched $C_1$-$C_4$-haloalkoxy, preferably phenyl monosubstituted by $C_1$-$C_2$-fluoroalkoxy and -chloroalkoxy, more especially phenyl monosubstituted by trifluoromethoxy and trichloromethoxy, such as trifluoromethoxyphenyl and 4-trichloromethoxyphenyl, aryl monosubstituted, disubstituted or trisubstituted by cyano, preferably phenyl monosubstituted by cyano, such as 4-cyanophenyl, aryl monosubstituted or disubstituted by nitro, preferably phenyl monosubstituted by nitro, such as 3-nitrophenyl, $C_7$-$C_{20}$-arylalkyl monosubstituted, disubstituted or trisubstituted by halogen in the aryl moiety, preferably $C_7$-$C_{10}$-phenylalkyl monosubstituted by fluorine or chlorine in the phenyl moiety, such as 4-fluorobenzyl and 4-chlorobenzyl, $C_7$-$C_{20}$-arylalkyl monosubstituted, disubstituted or trisubstituted by $C_1$-$C_8$-alkyl in the aryl moiety, preferably $C_7$-$C_{10}$-phenylalkyl monosubstituted by $C_1$-$C_4$-alkyl in the phenyl moiety, more especially $C_7$-$C_{10}$-phenylalkyl monosubstituted by $C_1$-$C_2$-alkyl in the phenyl moiety, such as 4-methylphenyl, 4-ethylbenzyl and 4-methylphenethyl, $C_7$-$C_{20}$-arylalkyl monosubstituted, disubstituted or trisubstituted by $C_1$-$C_8$-alkoxy in the aryl moiety, preferably $C_7$-$C_{10}$-phenylalkyl monosubstituted by $C_1$-$C_4$-alkoxy in the phenyl moiety, more especially $C_7$-$C_{10}$-phenylalkyl monosubstituted by $C_1$-$C_2$-alkoxy in the phenyl moiety, such as 4-methoxybenzyl, 4-ethoxybenzyl and 4-methoxyphenethyl, $C_7$-$C_{20}$-arylalkyl monosubstituted, disubstituted or trisubstituted by $C_1$-$C_4$-haloalkyl in the aryl moiety, preferably $C_7$-$C_{10}$-phenylalkyl monosubstituted by $C_1$-$C_2$-fluoroalkyl and -chloroalkyl in the phenyl moiety, more especially $C_7$-$C_{10}$-phenylalkyl monosubstituted by trifluoromethyl and trichloromethyl in the phenyl moiety, such as 4-trifluoromethylbenzyl and 4-trichloromethylbenzyl, $C_7$-$C_{20}$-arylalkyl monosubstituted, disubstituted or trisubstituted by $C_1$-$C_4$-haloalkoxy in the aryl moiety, preferably $C_7$-$C_{10}$-phenylalkyl monosubstituted by $C_1$-$C_2$-haloalkyl in the phenyl moiety, more especially $C_7$-$C_{10}$-phenylalkyl monosubstituted by trifluoromethyl and trichloromethyl, such as 4-trifluoromethoxybenzyl and 4-trichloromethoxybenzyl, $C_7$-$C_{20}$-arylalkyl monosubstituted, disubstituted or trisubstituted by cyano in the aryl moiety, preferably $C_7$-$C_{10}$-phenylalkyl monosubstituted by cyano in the phenyl moiety, such as 4-cyanobenzyl and 4-cyanophenethyl, $C_7$-$C_{20}$-arylalkyl monosubstituted or disubstituted by nitro in the aryl moiety, preferably $C_7$-$C_{10}$-phenylalkyl monosubstituted by nitro, such as 3-nitrobenzyl and $R^6$ is aryl monosubstituted, disubstituted or trisubstituted by halogen, preferably phenyl monosubstituted by fluorine or chlorine, such as 2-fluorophenyl, 3-fluorophenyl, 4-fluorophenyl, 2-chlorophenyl, 3-chlorophenyl and 4-chlorophenyl, hydrogen, branched or linear $C_1$-$C_8$-alkyl, preferably $C_1$-$C_4$-alkyl, more especially methyl, ethyl, n-propyl, isopropyl and tert.-butyl, $C_3$-$C_{10}$-cycloalkyl, preferably $C_3$-$C_8$-cycloalkyl, more especially $C_3$-$C_6$-cycloalkyl, such as cyclopropyl, cyclobutyl, cyclopentyl and cyclohexyl, aryl, preferably phenyl, 1-naphthyl and 2-naphthyl, more especially phenyl, aryl monosubstituted, disubstituted or trisubstituted by halogen, preferably phenyl monosubstituted by fluorine or chlorine, such as 2-fluorophenyl, 3-fluorophenyl, 4-fluorophenyl, 2-chlorophenyl, 3-chlorophenyl and 4-chlorophenyl, aryl monosubstituted, disubstituted or trisubstituted by $C_1$-$C_8$-alkyl, preferably phenyl monosubstituted by $C_1$-$C_4$-alkyl, more especially phenyl monosubstituted by $C_1$-$C_2$-alkyl, such as 4-methylphenyl and 4-ethylphenyl, aryl monosubstituted, disubstituted or trisubstituted by $C_1$-$C_8$-alkoxy, preferably phenyl monosubstituted by $C_1$-$C_4$-alkoxy, more especially phenyl monosubstituted by $C_1$-$C_2$-alkoxy, such as 4-methoxyphenyl and 4-ethoxyphenyl, aryl monosubstituted, disubstituted or trisubstituted by $C_1$-$C_4$-haloalkyl, preferably phenyl monosubstituted by $C_1$-$C_2$-fluoroalkyl and -chloroalkyl, more especially phenyl monosubstituted by trifluoromethyl and trichloroethyl, such as 4-trifluoromethylphenyl and 4-trichloromethylphenyl, and aryl monosubstituted, disubstituted or trisubstituted by $C_1$-$C_4$-haloalkoxy, preferably phenyl monosubstituted by $C_1$-$C_2$-fluoroalkoxy and -chloroalkoxy, more especially phenyl monosubstituted by trifluoromethoxy and trichloromethoxy, such as trifluoromethoxyphenyl and 4-trichloromethoxyphenyl.

$R^7$ is halogen, preferably fluorine, chlorine and bromine, more especially chlorine and bromine and $C_3$-$C_8$-cycloalkyl, preferably $C_3$-$C_7$-cycloalkyl, more especially $C_3$-$C_6$-cycloalkyl, such as cyclopropyl, cyclobutyl, cyclopentyl and cyclohexyl.

$R^9$ is hydrogen and also has the meanings given for $R^5$ and n is zero (an unsubstituted heterocyclic ring), one or, where relevant, two or three.

The (p-phenoxyphenoxy)-methyl five-ring heteroaromatic compounds of the general formula I are suited for effectively combating pests from the class comprising insects, mites and nematodes. They may be used as pesticides for protecting crops, and in the hygiene, stores protection and veterinary sectors. The compounds according to the invention affect the development of the animal organism and are virtually non-toxic for vertebrates. What is more, most of these compounds are readily degraded to substances which occur naturally and are further broken down by microorganisms.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua recticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenlchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 3 parts by weight of compound 31.25 is intimately mixed with 97 parts by weight of particulate kaolin. A dust is obtained containing 3% by weight of the active ingredient.

II. 30 parts by weight of compound 31.25 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound 31.25 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound 31.25 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound 31.25 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt% of active ingredient, or even the active ingredient without additives.

In the open, the amount of active ingredient applied is for example from 0.05 to 10, and preferably from 0.1 to 2, kg/ha. In the case of the isoazole compounds (II.31 and II.32), the preferred application rate is from 0.1 to 0.5 kg/ha.

There may be added to the active ingredient (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methyl-carbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

MANUFACTURING EXAMPLES

EXAMPLE 1

2-Chloro-5-[(4-phenoxyphenoxy)-methyl]-thiophene (compound no. 1.63)

5.57 g of 4-phenoxyphenol and 4.14 g of potassium carbonate are stirred for 1 hour at 70° C. in 50 ml of anhydrous dimethylformamide. Subsequently, 5 g of 2-chloro-5-chloromethylthiophene is dripped in, and the mixture is stirred for a further 12 hours at 80° C. and at room temperature (approx. 20° C.) overnight. The mixture is then stirred into 500 ml of ethyl acetate and washed three times with water. After drying over sodium sulfate and removal of the solvent, the residue is recrystallized from n-hexane. There is obtained 3.7 g of 2-chloro-5-[(4-chlorophenoxy)-methyl]-thiophene; colorless powder; m.p.: 48°-49° C.

EXAMPLE 2

2-Bromo-4-[(phenoxyphenoxy)-methyl]-thiophene (compound no. 4.54)

7.44 g of 4-phenoxyphenol and 5.52 g of potassium carbonate are stirred in 50 ml of anhydrous dimethylformamide for 1 hour at 70° C. 5.52 g of 2-bromo-4-chloromethylthiophene is then dripped in, and the mixture is stirred for a further 12 hours at 80° C., and at room temperature (approx. 20° C.) overnight. The mixture is then stirred into 500 ml of ethyl acetate and washed three times with water. After drying over sodium sulfate and removal of the solvent, the residue is recrystallized from n-hexane. There is obtained 10.7 g of 2-bromo-4-[(phenoxyphenoxy)-methyl]-thiophene; colorless powder; m.p.: 90° C.

EXAMPLE 3

5-Methyl-2-[(4-phenoxyphenoxy)-methyl]-1,3,4-oxadiazole (compound no. 20.24)

9.3 g of 4-phenoxyphenol and 9 g of potassium carbonate are stirred in 75 ml of anhydrous dimethylformamide for 1 hour at 80° C. Subsequently, 6.6 g of 2-chloromethyl-5-methyl-1,3,4-oxadiazole in 20 ml of anhydrous dimethylformamide is dripped in. The mixture is stirred for 10 hours at 80° C. and at room temperature (approx. 20° C.) overnight. The mixture is then stirred into 500 ml of ice water and extracted three times with ethyl acetate. After drying over sodium sulfate and removal of the solvent, the residue is purified by chromatography over silica gel using n-hexane/ethyl acetate (4:1) as eluant. There is obtained 12 g of 5-methyl-2-[(4-phenoxyphenoxy)-methyl]-1,3,4-oxadiazole; colorless crystals; m.p.: 78°-79° C.

EXAMPLE 4

3-Cyclopropyl-5-[(4-phenoxyphenoxy)-methyl]-oxadiazole (compound no. 26.20)

While cooling, 5.58 g of 4-phenoxyphenol as a solution in 30 ml of absolute dimethylformamide is dripped into 1 g of 80% strength sodium hydride in 25 ml of absolute dimethylformamide. Upon completion of hydrogen evolution, 4.76 g of 5-chloromethyl-3-cyclopropyl-1,2,4-oxadiazole is dripped in and the mixture is stirred for 8 hours at 80° C. After the solvent has been removed, the residue is slurried in 250 ml of water, extracted three times, each time with 100 ml of ether, and the combined ethe phases are dried over sodium sulfate. After removal of the solvent under reduced pressure and recrystallization of the crude product from methanol/water (1:1) there is obtained 8.0 g of 3-cyclopropyl-5-[(4-phenoxyphenoxy)-methyl]-1,2,4-oxadiazole; m.p.: 99° C.

EXAMPLE 5

2-Methyl-4-[(phenoxyphenoxy)-methyl]-thiazole (compound no. 11.11)

A solution of 8.83 g of 4-phenoxyphenol in 15 ml of absolute dimethylformamide is dripped into 1.5 g of 80% strength sodium hydride in 15 ml of absolute dimethylformamide. Upon completion of hydrogen evolution, 7.0 g of 4-chloromethyl-2-methylthiazole is dripped in and the mixture stirred for 3 hours at 80° C. After the solvent has been removed, the residue is slurried with 200 ml of water and extracted 3 times, each time with 50 ml of ether. After drying over sodium sulfate and removal of the solvent, the crude product is recrystallized from cyclohexane/methyl tert-butyl ether (20:1). There is obtained 6.5 g of 2-methyl-4-[(phenoxyphenoxy)-methyl]-thiazole; m.p.: 70°–73° C.

EXAMPLE 6

5-[(p-phenoxy)-phenoxymethyl]-3-methylisoxazole (compound no. 31.25)

At 10° to 20° C., 18.6 g of p-phenoxyphenol in 50 ml of dimethyl sulfoxide is dripped into 3.1 g of sodium hydride (85% strength in paraffin) in 100 ml of dimethyl sulfoxide. The mixture is stirred for 30 minutes at 50° C. and then 3-methyl-5-chloromethylisoxazole is dripped in at 15°–20° C. The mixture is worked up in the usual manner after 8 hours at 70° C. There is obtained 26.7 g of compound no. 31.25 of m.p. 48°–51° C.

Analysis: $C_{17}H_{15}O_3N$ (281) Calc.: C, 72.6; H, 5.4; N, 5.0. Found: C, 73.0; H, 5.6; N, 4.8.

The compounds I described in Tables 1 to 33 below may be prepared in accordance with the directions above. Where n=0, the heterocycle is unsubstituted.

TABLE 1

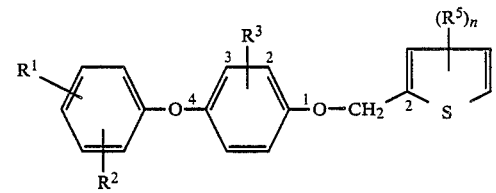

| Comp. No. | $R^1$ | $R^2$ | $R^3$ | $R^5$ | n | Phys. data (mp. °C.) |
|---|---|---|---|---|---|---|
| 1.1 | H | H | H | — | 0 | 55 |
| 1.2 | 3-Cl | H | H | — | 0 | |
| 1.3 | 3-Br | H | H | — | 0 | |
| 1.4 | 3-F | H | H | — | 0 | |
| 1.5 | 3-CF$_3$ | H | H | — | 0 | |
| 1.6 | 3-OCH$_3$ | H | H | — | 0 | |
| 1.7 | 3-CH$_3$ | H | H | — | 0 | |
| 1.8 | 3-C$_2$H$_5$ | H | H | — | 0 | |
| 1.9 | H | 4-F | H | — | 0 | |
| 1.10 | 3-Cl | 4-F | H | — | 0 | |
| 1.11 | H | H | 3-Cl | — | 0 | |
| 1.12 | H | H | 3-F | — | 0 | |
| 1.13 | 3-CH$_3$ | H | 3-F | — | 0 | |
| 1.14 | 3-C$_2$H$_5$ | H | 3-F | — | 0 | |
| 1.15 | 3-Cl | H | 3-F | — | 0 | |
| 1.16 | 3-F | H | 3-F | — | 0 | |
| 1.17 | 3-CF$_3$ | H | 3-F | — | 0 | |
| 1.18 | 3-Br | H | 3-F | — | 0 | |
| 1.19 | 3-OCH$_3$ | H | 3-F | — | 0 | |
| 1.20 | 3-CH$_3$ | H | 3-Cl | — | 0 | |
| 1.21 | 3-C$_2$H$_5$ | H | 3-Cl | — | 0 | |
| 1.22 | 3-Cl | H | 3-Cl | — | 0 | |
| 1.23 | 3-F | H | 3-Cl | — | 0 | |
| 1.24 | 3-CF$_3$ | H | 3-Cl | — | 0 | |
| 1.25 | 3-Br | H | 3-Cl | — | 0 | |
| 1.26 | 3-OCH$_3$ | H | 3-Cl | — | 0 | |
| 1.27 | 3-Cl | 4-F | 3-Cl | — | 0 | |
| 1.28 | 3-Cl | 4-F | 3-F | — | 0 | |
| 1.29 | H | 4-F | 3-F | — | 0 | |
| 1.30 | H | 4-F | 3-Cl | — | 0 | |
| 1.31 | H | H | H | 5-CH$_3$ | 1 | 52 |
| 1.32 | H | H | H | 5-cyclopropyl | 1 | |
| 1.33 | H | H | 3-F | 5-cyclopropyl | 1 | |
| 1.34 | H | H | 3-Cl | 5-cyclopropyl | 1 | |
| 1.35 | 3-F | H | H | 5-CH$_3$ | 1 | |
| 1.36 | 3-Cl | H | H | 5-CH$_3$ | 1 | |
| 1.37 | 3-Br | H | H | 5-CH$_3$ | 1 | |
| 1.38 | 3-CF$_3$ | H | H | 5-CH$_3$ | 1 | |
| 1.39 | 3-CH$_3$ | H | H | 5-CH$_3$ | 1 | |
| 1.40 | 3-C$_2$H$_5$ | H | H | 5-CH$_3$ | 1 | |
| 1.41 | 3-OCH$_3$ | H | H | 5-CH$_3$ | 1 | |
| 1.42 | 3-Cl | 4-F | H | 5-CH$_3$ | 1 | |
| 1.43 | 3-F | H | H | 5-cyclopropyl | 1 | |
| 1.44 | 3-Cl | H | H | 5-cyclopropyl | 1 | |
| 1.45 | 3-Br | H | H | 5-cyclopropyl | 1 | |
| 1.46 | 3-CF$_3$ | H | H | 5-cyclopropyl | 1 | |
| 1.47 | 3-CH$_3$ | H | H | 5-cyclopropyl | 1 | |
| 1.48 | 3-C$_2$H$_5$ | H | H | 5-cyclopropyl | 1 | |
| 1.49 | 3-OCH$_3$ | H | H | 5-cyclopropyl | 1 | |
| 1.50 | 3-Cl | 4-F | H | 5-cyclopropyl | 1 | |
| 1.51 | H | H | H | 4-CH$_3$ | 1 | |
| 1.52 | 3-F | H | H | 4-CH$_3$ | 1 | |

TABLE 1-continued

| Comp. No. | R¹ | R² | R³ | R⁵ | n | Phys. data (mp. °C.) |
|---|---|---|---|---|---|---|
| 1.53 | 3-Cl | H | H | 4-CH₃ | 1 | |
| 1.54 | 3-Br | H | H | 4-CH₃ | 1 | |
| 1.55 | 3-CF₃ | H | H | 4-CH₃ | 1 | |
| 1.56 | 3-CH₃ | H | H | 4-CH₃ | 1 | |
| 1.57 | 3-C₂H₅ | H | H | 4-CH₃ | 1 | |
| 1.58 | 3-OCH₃ | H | H | 4-CH₃ | 1 | |
| 1.59 | 3-Cl | 4-F | H | 4-CH₃ | 1 | |
| 1.60 | H | H | H | 4-cyclopropyl | 1 | |
| 1.61 | H | H | H | 3-CH₃ | 1 | 45 |
| 1.62 | H | H | H | 3-cyclopropyl | 1 | |
| 1.63 | H | H | H | 5-Cl | 1 | 48–49 |
| 1.64 | H | H | H | 5-Br | 1 | 56–57 |
| 1.65 | 3-F | H | H | 5-Cl | 1 | |
| 1.66 | 3-Cl | H | H | 5-Cl | 1 | |
| 1.67 | 3-Br | H | H | 5-Cl | 1 | |
| 1.68 | 3-CF₃ | H | H | 5-Cl | 1 | |
| 1.69 | 3-CH₃ | H | H | 5-Cl | 1 | |
| 1.70 | 3-C₂H₅ | H | H | 5-Cl | 1 | |
| 1.71 | 3-OCH₃ | H | H | 5-Cl | 1 | |
| 1.72 | 3-Cl | 4-F | H | 5-Cl | 1 | |
| 1.73 | H | H | H | 4-Cl | 1 | |
| 1.74 | H | H | H | 4-Br | 1 | 60–61 |
| 1.75 | 3-F | H | H | 4-Br | 1 | |
| 1.76 | 3-Cl | H | H | 4-Br | 1 | |
| 1.77 | 3-Br | H | H | 4-Br | 1 | |
| 1.78 | 3-CF₃ | H | H | 4-Br | 1 | |
| 1.79 | 3-CH₃ | H | H | 4-Br | 1 | |
| 1.80 | 3-C₂H₅ | H | H | 4-Br | 1 | |
| 1.81 | 3-OCH₃ | H | H | 4-Br | 1 | |
| 1.82 | 3-Cl | 4-F | H | 4-Br | 1 | |
| 1.83 | H | H | H | 4,5-dichloro | 2 | |
| 1.84 | 3-CH₃ | H | H | 4,5-dichloro | 2 | |
| 1.85 | H | H | H | 4-OCH₃ | 1 | |
| 1.86 | H | H | H | 4-OC₂H₅ | 1 | |
| 1.87 | H | H | H | 4-OCH₃ | 1 | |
| 1.88 | H | H | H | 4-OC₂H₅ | 1 | |
| 1.89 | 3-F | H | H | 4-OC₂H₅ | 1 | |
| 1.90 | 3-Cl | H | H | 4-OC₂H₅ | 1 | |
| 1.91 | 3-Br | H | H | 4-OC₂H₅ | 1 | |
| 1.92 | 3-CF₃ | H | H | 4-OC₂H₅ | 1 | |
| 1.93 | 3-CH₃ | H | H | 4-OC₂H₅ | 1 | |
| 1.94 | 3-C₂H₅ | H | H | 4-OC₂H₅ | 1 | |
| 1.95 | 3-OCH₃ | H | H | 4-OC₂H₅ | 1 | |
| 1.96 | 3-Cl | 4-F | H | 4-OC₂H₅ | 1 | |
| 1.97 | H | H | 3-F | 4-OC₂H₅ | 1 | |
| 1.98 | H | H | 3-Cl | 4-OC₂H₅ | 1 | |
| 1.99 | 3-F | H | H | 5-Br | 1 | 48–50 |
| 1.100 | 3-Cl | H | H | 5-Br | 1 | 44–45 |
| 1.101 | 3-Br | H | H | 5-Br | 1 | 59–61 |
| 1.102 | 3-CF₃ | H | H | 5-Br | 1 | 38–40 |
| 1.103 | 3-CH₃ | H | H | 5-Br | 1 | 56–57 |
| 1.104 | 3-C₂H₅ | H | H | 5-Br | 1 | 48–50 |
| 1.105 | 3-OCH₃ | H | H | 5-Br | 1 | 58–60 |
| 1.106 | 3-Cl | 4-F | H | 5-Br | 1 | 69–71 |
| 1.107 | H | H | 3-F | 5-Br | 1 | |
| 1.108 | H | H | 3-Cl | 5-Br | 1 | |
| 1.109 | 3-F | H | 3-F | 5-Br | 1 | |
| 1.110 | 3-F | H | 3-Cl | 5-Br | 1 | |
| 1.111 | 3-Cl | H | 3-F | 5-Br | 1 | |
| 1.112 | 3-Cl | H | 3-Cl | 5-Br | 1 | |
| 1.113 | 3-Br | H | 3-F | 5-Br | 1 | |
| 1.114 | 3-Br | H | 3-Cl | 5-Br | 1 | |
| 1.115 | 3-CF₃ | H | 3-F | 5-Br | 1 | 300-MHz-¹H—NMR in CDCl₃ [ppm]: 5.39 (s) |
| 1.116 | 3-CF₃ | H | 3-Cl | 5-Br | 1 | |
| 1.117 | 3-CH₃ | H | 3-F | 5-Br | 1 | |
| 1.118 | 3-CH₃ | H | 3-Cl | 5-Br | 1 | |
| 1.119 | 3-C₂H₅ | H | 3-F | 5-Br | 1 | |

TABLE 1-continued

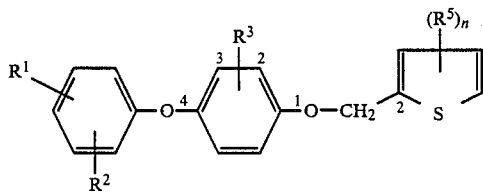

| Comp. No. | $R^1$ | $R^2$ | $R^3$ | $R^5$ | n | Phys. data (mp. °C.) |
|---|---|---|---|---|---|---|
| 1.120 | 3-$C_2H_5$ | H | 3-Cl | 5-Br | 1 | |
| 1.121 | 3-$OCH_3$ | H | 3-F | 5-Br | 1 | |
| 1.122 | 3-Cl | 4-F | 3-F | 5-Br | 1 | |
| 1.123 | 4-F | H | H | 5-Br | 1 | 59-61 |
| 1.124 | 3-t-$C_4H_9$ | H | H | 5-Br | 1 | 300-MHz-$^1$H—NMR in $CDCl_3$ [ppm]: 1.34(s) |

TABLE 2

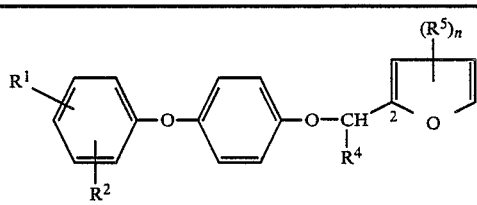

| Comp. No. | $R^1$ | $R^2$ | $R^4$ | $R^5$ | n | Phys. data (mp. °C.) |
|---|---|---|---|---|---|---|
| 2.1 | H | H | H | — | 0 | |
| 2.2 | H | H | $CH_3$ | — | 0 | |
| 2.3 | 3-F | H | H | — | 0 | |
| 2.4 | 3-Cl | H | H | — | 0 | |
| 2.5 | 3-Br | H | H | — | 0 | |
| 2.6 | 3-$CF_3$ | H | H | — | 0 | |
| 2.7 | 3-$CH_3$ | H | H | — | 0 | |
| 2.8 | 3-$C_2H_5$ | H | H | — | 0 | |
| 2.9 | 3-$OCH_3$ | H | H | — | 0 | |
| 2.10 | 3-Cl | 4-F | H | — | 0 | |
| 2.11 | H | H | H | 4-$CH_3$ | 1 | |
| 2.12 | 3-F | H | H | 4-$CH_3$ | 1 | |
| 2.13 | 3-Cl | H | H | 4-$CH_3$ | 1 | |
| 2.14 | 3-Br | H | H | 4-$CH_3$ | 1 | |
| 2.15 | 3-$CF_3$ | H | H | 4-$CH_3$ | 1 | |
| 2.16 | 3-$CH_3$ | H | H | 4-$CH_3$ | 1 | |
| 2.17 | 3-$C_2H_5$ | H | H | 4-$CH_3$ | 1 | |
| 2.18 | 3-$OCH_3$ | H | H | 4-$CH_3$ | 1 | |
| 2.19 | 3-Cl | 4-F | H | 4-$CH_3$ | 1 | |
| 2.20 | H | H | H | 5-$CH_3$ | 1 | |
| 2.21 | 3-F | H | H | 5-$CH_3$ | 1 | |
| 2.22 | 3-Cl | H | H | 5-$CH_3$ | 1 | |
| 2.23 | 3-Br | H | H | 5-$CH_3$ | 1 | |
| 2.24 | 3-$CF_3$ | H | H | 5-$CH_3$ | 1 | |
| 2.25 | 3-$CH_3$ | H | H | 5-$CH_3$ | 1 | |
| 2.26 | 3-$C_2H_5$ | H | H | 5-$CH_3$ | 1 | |
| 2.27 | 3-$OCH_3$ | H | H | 5-$CH_3$ | 1 | |
| 2.28 | 3-Cl | 4-F | H | 5-$CH_3$ | 1 | |
| 2.29 | H | H | H | 5-cyclopropyl | 1 | |
| 2.30 | 3-F | H | H | 5-cyclopropyl | 1 | |
| 2.31 | 3-Cl | H | H | 5-cyclopropyl | 1 | |
| 2.32 | 3-Br | H | H | 5-cyclopropyl | 1 | |
| 2.33 | 3-$CF_3$ | H | H | 5-cyclopropyl | 1 | |
| 2.34 | 3-$CH_3$ | H | H | 5-cyclopropyl | 1 | |
| 2.35 | 3-$C_2H_5$ | H | H | 5-cyclopropyl | 1 | |
| 2.36 | 3-$OCH_3$ | H | H | 5-cyclopropyl | 1 | |
| 2.37 | 3-Cl | 4-F | H | 5-cyclopropyl | 1 | |
| 2.38 | 3-F | H | H | 4-cyclopropyl | 1 | |
| 2.39 | 3-Cl | H | H | 4-cyclopropyl | 1 | |
| 2.40 | 3-Br | H | H | 4-cyclopropyl | 1 | |
| 2.41 | 3-$CF_3$ | H | H | 4-cyclopropyl | 1 | |
| 2.42 | 3-$CH_3$ | H | H | 4-cyclopropyl | 1 | |
| 2.43 | 3-$C_2H_5$ | H | H | 4-cyclopropyl | 1 | |
| 2.44 | 3-$OCH_3$ | H | H | 4-cyclopropyl | 1 | |

TABLE 2-continued

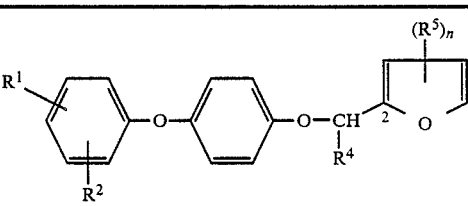

| Comp. No. | $R^1$ | $R^2$ | $R^4$ | $R^5$ | n | Phys. data (mp. °C.) |
|---|---|---|---|---|---|---|
| 2.45 | 3-Cl | H | H | 4-cyclopropyl | 1 | |

TABLE 3

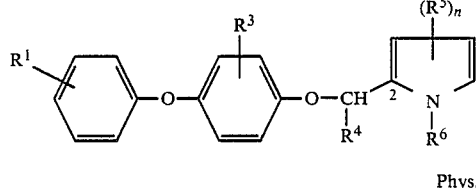

| Comp. No. | $R^1$ | $R^3$ | $R^4$ | $R^5$ | $R^6$ | n | Phys. data (mp. °C.) |
|---|---|---|---|---|---|---|---|
| 3.1 | H | H | H | — | $CH_3$ | 0 | |
| 3.2 | 3-F | H | H | — | $CH_3$ | 0 | |
| 3.3 | 3-Cl | H | H | — | $CH_3$ | 0 | |
| 3.4 | 3-Br | H | H | — | $CH_3$ | 0 | |
| 3.5 | 3-$CF_3$ | H | H | — | $CH_3$ | 0 | |
| 3.6 | 3-$CH_3$ | H | H | — | $CH_3$ | 0 | |
| 3.7 | 4-F | H | H | — | $CH_3$ | 0 | |
| 3.8 | 3-$C_2H_5$ | H | H | — | $CH_3$ | 0 | |
| 3.9 | 3-F | H | H | 4-Cl | $CH_3$ | 1 | |
| 3.10 | 3-Cl | H | H | 4-Cl | $CH_3$ | 1 | |
| 3.11 | 3-Br | H | H | 4-Cl | $CH_3$ | 1 | |
| 3.12 | 3-$CF_3$ | H | H | 4-Cl | $CH_3$ | 1 | |
| 3.13 | 3-$CH_3$ | H | H | 4-Cl | $CH_3$ | 1 | |
| 3.14 | 4-F | H | H | 4-Cl | $CH_3$ | 1 | |
| 3.15 | 3-$C_2H_5$ | H | H | 4-Cl | $CH_3$ | 1 | |
| 3.16 | 3-$OC_2H_5$ | H | H | 4-Cl | $CH_3$ | 1 | |
| 3.17 | 3-$OCH_3$ | H | H | 4-Cl | $CH_3$ | 1 | |
| 3.18 | 3-F | H | H | 4-i-$C_3H_7$ | $CH_3$ | 1 | |
| 3.19 | 3-Cl | H | H | 4-i-$C_3H_7$ | $CH_3$ | 1 | |
| 3.20 | 3-Br | H | H | 4-i-$C_3H_7$ | $CH_3$ | 1 | |
| 3.21 | 3-$CF_3$ | H | H | 4-i-$C_3H_7$ | $CH_3$ | 1 | |
| 3.22 | 3-$CH_3$ | H | H | 4-i-$C_3H_7$ | $CH_3$ | 1 | |
| 3.23 | 4-F | H | H | 4-i-$C_3H_7$ | $CH_3$ | 1 | |
| 3.24 | 3-$C_2H_5$ | H | H | 4-i-$C_3H_7$ | $CH_3$ | 1 | |
| 3.25 | 3-$OC_2H_5$ | H | H | 4-i-$C_3H_7$ | $CH_3$ | 1 | |
| 3.26 | 3-$OCH_3$ | H | H | 4-i-$C_3H_7$ | $CH_3$ | 1 | |
| 3.27 | 3-F | H | H | 5-Cl | $CH_3$ | 1 | |

TABLE 3-continued

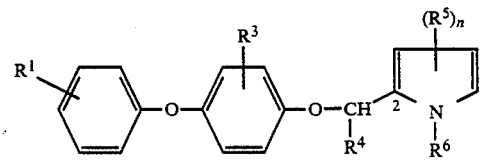

| Comp. No. | $R^1$ | $R^3$ | $R^4$ | $R^5$ | $R^6$ | n | Phys. data (mp. °C.) |
|---|---|---|---|---|---|---|---|
| 3.28 | 3-Cl | H | H | 5-Cl | $CH_3$ | 1 | |
| 3.29 | 3-Br | H | H | 5-Cl | $CH_3$ | 1 | |
| 3.30 | 3-$CF_3$ | H | H | 5-Cl | $CH_3$ | 1 | |
| 3.31 | 3-$CH_3$ | H | H | 5-Cl | $CH_3$ | 1 | |
| 3.32 | 4-F | H | H | 5-Cl | $CH_3$ | 1 | |
| 3.33 | 3-$C_2H_5$ | H | H | 5-Cl | $CH_3$ | 1 | |
| 3.34 | 3-$OC_2H_5$ | H | H | 5-Cl | $CH_3$ | 1 | |
| 3.35 | 3-$OCH_3$ | H | H | 5-Cl | $CH_3$ | 1 | |
| 3.36 | 3-F | H | $CH_3$ | 5-Cl | $CH_3$ | 1 | |
| 3.37 | 3-Cl | H | $CH_3$ | 5-Cl | $CH_3$ | 1 | |

TABLE 3-continued

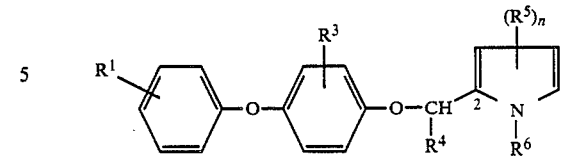

| Comp. No. | $R^1$ | $R^3$ | $R^4$ | $R^5$ | $R^6$ | n | Phys. data (mp. °C.) |
|---|---|---|---|---|---|---|---|
| 3.38 | 3-Br | H | $CH_3$ | 5-Cl | $CH_3$ | 1 | |
| 3.39 | 3-$CF_3$ | H | $CH_3$ | 5-Cl | $CH_3$ | 1 | |
| 3.40 | 4-F | H | $CH_3$ | 5-Cl | $CH_3$ | 1 | |
| 3.41 | 3-$C_2H_5$ | H | $CH_3$ | 5-Cl | $CH_3$ | 1 | |
| 3.42 | 3-$OC_2H_5$ | H | $CH_3$ | 5-Cl | $CH_3$ | 1 | |
| 3.43 | 3-$OCH_3$ | H | $CH_3$ | 5-Cl | $CH_3$ | 1 | |
| 3.44 | 3-F | 3-F | $CH_3$ | — | $CH_3$ | 0 | |
| 3.45 | 3-Cl | 3-F | H | — | $CH_3$ | 0 | |
| 3.46 | 3-Br | 3-F | H | — | $CH_3$ | 0 | |
| 3.47 | 4-F | 3-F | H | — | $CH_3$ | 0 | |

TABLE 4

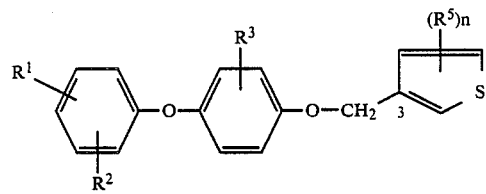

| Comp. No. | $R^1$ | $R^2$ | $R^3$ | $R^5$ | n | Phys data (mp. °C.) |
|---|---|---|---|---|---|---|
| 4.1 | H | H | H | — | 0 | 74 |
| 4.2 | H | H | 3-F | — | 0 | |
| 4.3 | H | H | 3-Cl | — | 0 | |
| 4.4 | 3-F | H | H | — | 0 | |
| 4.5 | 3-Cl | H | H | — | 0 | |
| 4.6 | 3-Br | H | H | — | 0 | |
| 4.7 | 3-$CF_3$ | H | H | — | 0 | |
| 4.8 | 3-$CH_3$ | H | H | — | 0 | |
| 4.9 | 3-$C_2H_5$ | H | H | — | 0 | |
| 4.10 | 3-$OCH_3$ | H | H | — | 0 | |
| 4.11 | 3-Cl | 4-F | H | — | 0 | |
| 4.12 | H | H | H | 4-$CH_3$ | 1 | |
| 4.13 | H | H | H | 4-cyclopropyl | 1 | |
| 4.14 | H | H | H | 5-$CH_3$ | 1 | |
| 4.15 | H | H | H | 5-cyclopropyl | 1 | |
| 4.16 | H | H | H | 4-$OCH_3$ | 1 | |
| 4.17 | H | H | H | 4-$OC_2H_5$ | 1 | |
| 4.18 | H | H | H | 5-$OCH_3$ | 1 | |
| 4.19 | H | H | H | 5-$OC_2H_5$ | 1 | |
| 4.20 | H | H | H | 4-Cl | 1 | |
| 4.21 | H | H | H | 4-Br | 1 | |
| 4.22 | H | H | H | 5-Cl | 1 | 84–85 |
| 4.23 | 3-F | H | H | 5-Cl | 1 | |
| 4.24 | 3-Cl | H | H | 5-Cl | 1 | |
| 4.25 | 3-Br | H | H | 5-Cl | 1 | |
| 4.26 | 3-$CF_3$ | H | H | 5-Cl | 1 | |
| 4.27 | 3-$CH_3$ | H | H | 5-Cl | 1 | |
| 4.28 | 3-$C_2H_5$ | H | H | 5-Cl | 1 | |
| 4.29 | 3-$OCH_3$ | H | H | 5-Cl | 1 | |
| 4.30 | 3-Cl | 4-F | H | 5-Cl | 1 | |
| 4.40 | H | H | 3-Cl | 5-Cl | 1 | |
| 4.41 | H | H | 3-F | 5-Cl | 1 | |
| 4.42 | 3-F | H | 3-F | 5-Cl | 1 | |
| 4.43 | 3-Cl | H | 3-F | 5-Cl | 1 | |
| 4.44 | 3-$CF_3$ | H | 3-F | 5-Cl | 1 | |
| 4.45 | 3-$OCH_3$ | H | 3-F | 5-Cl | 1 | |
| 4.46 | 3-Cl | 4-F | 3-F | 5-Cl | 1 | |
| 4.47 | 3-F | H | 3-Cl | 5-Cl | 1 | |
| 4.48 | 3-Cl | H | 3-Cl | 5-Cl | 1 | |
| 4.49 | 3-Br | H | 3-Cl | 5-Cl | 1 | |
| 4.50 | 3-$CF_3$ | H | 3-Cl | 5-Cl | 1 | |
| 4.51 | 3-$OCH_3$ | H | 3-Cl | 5-Cl | 1 | |
| 4.52 | 3-$CH_3$ | H | 3-Cl | 5-Cl | 1 | |

TABLE 4-continued

Structure: R¹-(phenyl with R²)-O-(phenyl with R³)-O-CH₂-(thiophene with (R⁵)n)

| Comp. No. | R¹ | R² | R³ | R⁵ | n | Phys data (mp. °C.) |
|---|---|---|---|---|---|---|
| 4.53 | 3-Cl | 4-F | 3-Cl | 5-Cl | 1 | |
| 4.54 | H | H | H | 5-Br | 1 | 90 |
| 4.55 | 3-F | H | H | 5-Br | 1 | |
| 4.56 | 3-Cl | H | H | 5-Br | 1 | |
| 4.57 | 3-Br | H | H | 5-Br | 1 | |
| 4.58 | 3-CF$_3$ | H | H | 5-Br | 1 | |
| 4.59 | 3-CH$_3$ | H | H | 5-Br | 1 | |
| 4.60 | 3-C$_2$H$_5$ | H | H | 5-Br | 1 | |
| 4.61 | 3-OCH$_3$ | H | H | 5-Br | 1 | |
| 4.62 | 3-Cl | 4-F | H | 5-Br | 1 | |
| 4.63 | H | H | H | 4,5-dichloro | 2 | 68–71 |
| 4.64 | 3-F | H | H | 4,5-dichloro | 2 | 53–54 |
| 4.65 | 3-Cl | H | H | 4,5-dichloro | 2 | 74–76 |
| 4.66 | 3-Br | H | H | 4,5-dichloro | 2 | 86–90 |
| 4.67 | 3-CF$_3$ | H | H | 4,5-dichloro | 2 | 69–72 |
| 4.68 | 3-CH$_3$ | H | H | 4,5-dichloro | 2 | 67–71 |
| 4.69 | 3-C$_2$H$_5$ | H | H | 4,5-dichloro | 2 | 300-MHz-$^1$H—NMR in CDCl$_3$ [ppm]: 4.96(s) |
| 4.70 | 3-OCH$_3$ | H | H | 4,5-dichloro | 2 | 59–62 |
| 4.71 | 3-Cl | 4-F | H | 4,5-dichloro | 2 | 300-MHz-$^1$H—NMR in CDCl$_3$ [ppm]: 4.95 (s) |
| 4.72 | H | H | 3-Cl | 4,5-dichloro | 2 | |
| 4.73 | H | H | 3-F | 4,5-dichloro | 2 | |
| 4.74 | H | H | H | 4,5-dibromo | 2 | 95 |
| 4.75 | H | H | 3-Cl | 4,5-dibromo | 2 | |
| 4.76 | H | H | 3-F | 4,5-dibromo | 2 | |
| 4.77 | 3-F | H | H | 4,5-dibromo | 2 | 64–67 |
| 4.78 | 3-Cl | H | H | 4,5-dibromo | 2 | 95 |
| 4.79 | 3-Br | H | H | 4,5-dibromo | 2 | 98 |
| 4.80 | 3-CF$_3$ | H | H | 4,5-dibromo | 2 | 81 |
| 4.81 | 3-CH$_3$ | H | H | 4,5-dibromo | 2 | 80 |
| 4.82 | 3-C$_2$H$_5$ | H | H | 4,5-dibromo | 2 | 89–91 |
| 4.83 | 3-OCH$_3$ | H | H | 4,5-dibromo | 2 | 75 |
| 4.84 | 3-Cl | 4-F | H | 4,5-dibromo | 2 | 300 MHz-$^1$H—NMR in CDCl$_3$ [ppm]: 4.96 (s) |
| 4.85 | 3-F | H | 3-Cl | 4,5-dibromo | 2 | |
| 4.86 | 3-Cl | H | 3-Cl | 4,5-dibromo | 2 | |
| 4.87 | 3-Br | H | 3-Cl | 4,5-dibromo | 2 | |
| 4.88 | 3-CF$_3$ | H | 3-Cl | 4,5-dibromo | 2 | |
| 4.89 | 3-CH$_3$ | H | 3-Cl | 4,5-dibromo | 2 | 92–95 |
| 4.90 | 3-C$_2$H$_5$ | H | 3-Cl | 4,5-dibromo | 2 | |
| 4.91 | 3-OCH$_3$ | H | 3-Cl | 4,5-dibromo | 2 | |
| 4.92 | 3-Cl | 4-F | 3-Cl | 4,5-dibromo | 2 | |
| 4.93 | 3-F | H | 3-F | 4,5-dibromo | 2 | |
| 4.94 | 3-Cl | H | 3-F | 4,5-dibromo | 2 | |
| 4.95 | 3-Br | H | 3-F | 4,5-dibromo | 2 | |
| 4.96 | 3-CF$_3$ | H | 3-F | 4,5-dibromo | 2 | |
| 4.97 | 3-CH$_3$ | H | 3-F | 4,5-dibromo | 2 | |
| 4.98 | 3-OCH$_3$ | H | 3-F | 4,5-dibromo | 2 | |
| 4.99 | H | H | H | 2,4,5-tribromo | 3 | |
| 4.100 | 3-Cl | 4-F | 3-F | 4,5-dibromo | 2 | |
| 4.101 | H | 4-F | 3-F | 4,5-dibromo | 2 | |
| 4.102 | H | 4-F | 3-Cl | 4,5-dibromo | 2 | |
| 4.103 | 4-F | H | H | 4,5-dichloro | 2 | 57–58 |

TABLE 5

![Structure: R¹-phenyl-O-phenyl-O-CH(R⁴)-furan(R⁵)n with R² on first ring]

| Comp. No. | R¹ | R² | R⁴ | R⁵ | n | Phys. data (mp. °C.) |
|---|---|---|---|---|---|---|
| 5.1 | H | H | H | — | 0 | |
| 5.2 | H | H | CH₃ | — | 0 | |
| 5.3 | 3-F | H | H | — | 0 | |
| 5.4 | 3-Cl | H | H | — | 0 | |
| 5.5 | 3-Br | H | H | — | 0 | |
| 5.6 | 3-CF₃ | H | H | — | 0 | |
| 5.7 | 3-CH₃ | H | H | — | 0 | |
| 5.8 | 3-C₂H₅ | H | H | — | 0 | |
| 5.9 | 3-OCH₃ | H | H | — | 0 | |
| 5.10 | 3-Cl | 4-F | H | — | 0 | |
| 5.11 | H | H | H | 4-CH₃ | 1 | |
| 5.12 | 3-F | H | H | 4-CH₃ | 1 | |
| 5.13 | 3-Cl | H | H | 4-CH₃ | 1 | |
| 5.14 | 3-Br | H | H | 4-CH₃ | 1 | |
| 5.15 | 3-CF₃ | H | H | 4-CH₃ | 1 | |
| 5.16 | 3-CH₃ | H | H | 4-CH₃ | 1 | |
| 5.17 | 3-C₂H₅ | H | H | 4-CH₃ | 1 | |
| 5.18 | 3-OCH₃ | H | H | 4-CH₃ | 1 | |
| 5.19 | 3-Cl | 4-F | H | 4-CH₃ | 1 | |
| 5.20 | H | H | H | 4-cyclopropyl | 1 | |
| 5.21 | 3-F | H | H | 4-cyclopropyl | 1 | |
| 5.22 | 3-Cl | H | H | 4-cyclopropyl | 1 | |
| 5.23 | 3-Br | H | H | 4-cyclopropyl | 1 | |
| 5.24 | 3-CF₃ | H | H | 4-cyclopropyl | 1 | |
| 5.25 | 3-CH₃ | H | H | 4-cyclopropyl | 1 | |
| 5.26 | 3-C₂H₅ | H | H | 4-cyclopropyl | 1 | |
| 5.27 | 3-OCH₃ | H | H | 4-cyclopropyl | 1 | |
| 5.28 | 3-Cl | 4-F | H | 4-cyclopropyl | 1 | |
| 5.29 | H | H | H | 5-CH₃ | 1 | |
| 5.30 | H | H | H | 5-iso-C₃H₇ | 1 | 300-MHz-¹H—NMR in CDCl₃ [ppm]: 4.86 (s) |
| 5.31 | 3-F | H | H | 5-CH₃ | 1 | |
| 5.32 | 3-Cl | H | H | 5-CH₃ | 1 | |
| 5.33 | 3-Br | H | H | 5-CH₃ | 1 | |
| 5.34 | 3-CF₃ | H | H | 5-CH₃ | 1 | |
| 5.35 | 3-CH₃ | H | H | 5-CH₃ | 1 | |
| 5.36 | 3-C₂H₅ | H | H | 5-CH₃ | 1 | |
| 5.37 | 3-OCH₃ | H | H | 5-CH₃ | 1 | |
| 5.38 | 3-Cl | 4-F | H | 5-CH₃ | 1 | |
| 5.39 | H | H | H | 5-cyclopropyl | 1 | |
| 5.40 | 3-F | H | H | 5-cyclopropyl | 1 | |
| 5.41 | 3-Cl | H | H | 5-cyclopropyl | 1 | |
| 5.42 | 3-Br | H | H | 5-cyclopropyl | 1 | |
| 5.43 | 3-CF₃ | H | H | 5-cyclopropyl | 1 | |
| 5.44 | 3-CH₃ | H | H | 5-cyclopropyl | 1 | |
| 5.45 | 3-C₂H₅ | H | H | 5-cyclopropyl | 1 | |
| 5.46 | 3-OCH₃ | H | H | 5-cyclopropyl | 1 | |
| 5.47 | 3-Cl | 4-F | H | 5-cyclopropyl | 1 | |

TABLE 6

![Structure: R¹-phenyl-O-phenyl(R³)-O-CH(R⁴)-pyrrole(R⁵)n-N-R⁶]

| Comp. No. | R¹ | R³ | R⁴ | R⁵ | R⁶ | n | Phys. data (mp. °C.) |
|---|---|---|---|---|---|---|---|
| 6.1 | H | H | H | — | CH₃ | 0 | |
| 6.2 | H | H | CH₃ | — | CH₃ | 0 | |
| 6.3 | 3-F | H | H | — | CH₃ | 0 | |
| 6.4 | 3-Cl | H | H | — | CH₃ | 0 | |
| 6.5 | 3-Br | H | H | — | CH₃ | 0 | |
| 6.6 | 3-CF₃ | H | H | — | CH₃ | 0 | |
| 6.7 | 3-CH₃ | H | H | — | CH₃ | 0 | |
| 6.8 | 3-C₂H₅ | H | H | — | CH₃ | 0 | |
| 6.9 | 3-OCH₃ | H | H | — | CH₃ | 0 | |
| 6.10 | 3-OC₂H₅ | H | H | — | CH₃ | 0 | |
| 6.11 | 4-F | H | H | — | CH₃ | 0 | |
| 6.12 | 3-F | H | H | 4-Cl | CH₃ | 1 | |
| 6.13 | 3-Cl | H | H | 4-Cl | CH₃ | 1 | |
| 6.14 | 3-Br | H | H | 4-Cl | CH₃ | 1 | |
| 6.15 | 3-CF₃ | H | H | 4-Cl | CH₃ | 1 | |
| 6.16 | 3-CH₃ | H | H | 4-Cl | CH₃ | 1 | |
| 6.17 | 3-C₂H₅ | H | H | 4-Cl | CH₃ | 1 | |
| 6.18 | 3-CH₃ | H | H | 4-Cl | CH₃ | 1 | |
| 6.19 | 3-OC₂H₅ | H | H | 4-Cl | CH₃ | 1 | |
| 6.20 | 4-F | H | H | 4-Cl | CH₃ | 1 | |
| 6.21 | 3-F | 3-F | CH₃ | 4-Cl | CH₃ | 1 | |
| 6.22 | 3-Cl | 3-F | CH₃ | 4-Cl | CH₃ | 1 | |
| 6.23 | 3-Br | 3-F | CH₃ | 4-Cl | CH₃ | 1 | |
| 6.24 | 3-CF₃ | 3-F | CH₃ | 4-Cl | CH₃ | 1 | |
| 6.25 | 3-CH₃ | 3-F | CH₃ | 4-Cl | CH₃ | 1 | |
| 6.26 | 3-C₂H₅ | 3-F | CH₃ | 4-Cl | CH₃ | 1 | |
| 6.27 | 3-OCH₃ | 3-F | CH₃ | 4-Cl | CH₃ | 1 | |
| 6.28 | 3-OC₂H₅ | 3-F | CH₃ | 4-Cl | CH₃ | 1 | |
| 6.29 | 4-F | 3-F | CH₃ | 4-Cl | CH₃ | 1 | |
| 6.30 | 3-F | 3-F | CH₃ | 5-Cl | CH₃ | 1 | |
| 6.31 | 3-Cl | 3-F | CH₃ | 5-Cl | CH₃ | 1 | |
| 6.32 | 3-Br | 3-F | CH₃ | 5-Cl | CH₃ | 1 | |
| 6.33 | 3-CF₃ | 3-F | CH₃ | 5-Cl | CH₃ | 1 | |
| 6.34 | 3-CH₃ | 3-F | CH₃ | 5-Cl | CH₃ | 1 | |
| 6.35 | 3-C₂H₅ | 3-F | CH₃ | 5-Cl | CH₃ | 1 | |
| 6.36 | 3-OCH₃ | 3-F | CH₃ | 5-Cl | CH₃ | 1 | |
| 6.37 | 3-OC₂H₅ | 3-F | CH₃ | 5-Cl | CH₃ | 1 | |
| 6.38 | 4-F | 3-F | CH₃ | 5-Cl | CH₃ | 1 | |
| 6.39 | 3-F | H | H | 4-CH₃ | CH₃ | 1 | |
| 6.40 | 3-Cl | H | H | 4-CH₃ | CH₃ | 1 | |
| 6.41 | 3-Br | H | H | 4-CH₃ | CH₃ | 1 | |
| 6.42 | 3-CF₃ | H | H | 4-CH₃ | CH₃ | 1 | |
| 6.43 | 3-CH₃ | H | H | 4-CH₃ | CH₃ | 1 | |
| 6.44 | 3-C₂H₅ | H | H | 4-CH₃ | CH₃ | 1 | |
| 6.45 | 3-OCH₃ | H | H | 4-CH₃ | CH₃ | 1 | |
| 6.46 | 3-OC₂H₅ | H | H | 4-CH₃ | CH₃ | 1 | |
| 6.47 | 4-F | H | H | 4-CH₃ | CH₃ | 1 | |

TABLE 7

![Structure: R¹-phenyl-O-phenyl(R³)-O-CH(R⁴)-thiazole(R⁵)n]

| Comp. No. | R¹ | R² | R³ | R⁴ | R⁵ | n | Phys. data (mp. °C.) |
|---|---|---|---|---|---|---|---|
| 7.1 | H | H | H | H | — | 0 | |
| 7.2 | H | H | H | CH₃ | — | 0 | |
| 7.3 | 3-F | H | H | H | — | 0 | |
| 7.4 | 3-Cl | H | H | H | — | 0 | |
| 7.5 | 3-Br | H | H | H | — | 0 | |
| 7.6 | 3-CF₃ | H | H | H | — | 0 | |
| 7.7 | 3-CH₃ | H | H | H | — | 0 | |
| 7.8 | 3-C₂H₅ | H | H | H | — | 0 | |

TABLE 7-continued

Structure: $R^1, R^2$ on first phenyl ring connected via O to second phenyl ring with $R^3$, connected via O—CH($R^4$) to a thiophene ring bearing $(R^5)_n$

| Comp. No. | $R^1$ | $R^2$ | $R^3$ | $R^4$ | $R^5$ | n | Phys. data (mp. °C.) |
|---|---|---|---|---|---|---|---|
| 7.9  | 3-OCH$_3$ | H    | H    | H   | —           | 0 | |
| 7.10 | 3-Cl      | 4-F  | H    | H   | —           | 0 | |
| 7.11 | H         | H    | H    | H   | 2-CH$_3$    | 1 | |
| 7.12 | 3-F       | H    | H    | H   | 2-CH$_3$    | 1 | |
| 7.13 | 3-Cl      | H    | H    | H   | 2-CH$_3$    | 1 | |
| 7.14 | 3-Br      | H    | H    | H   | 2-CH$_3$    | 1 | |
| 7.15 | 3-CF$_3$  | H    | H    | H   | 2-CH$_3$    | 1 | |
| 7.16 | 3-CH$_3$  | H    | H    | H   | 2-CH$_3$    | 1 | |
| 7.17 | 3-C$_2$H$_5$ | H | H    | H   | 2-CH$_3$    | 1 | |
| 7.18 | 3-OCH$_3$ | H    | H    | H   | 2-CH$_3$    | 1 | |
| 7.19 | 3-Cl      | 4-F  | H    | H   | 2-CH$_3$    | 1 | |
| 7.20 | H         | H    | H    | H   | 2-cyclopropyl | 1 | |
| 7.21 | 3-F       | H    | H    | H   | 2-cyclopropyl | 1 | |
| 7.22 | 3-Cl      | H    | H    | H   | 2-cyclopropyl | 1 | |
| 7.23 | 3-Br      | H    | H    | H   | 2-cyclopropyl | 1 | |
| 7.24 | 3-CF$_3$  | H    | H    | H   | 2-cyclopropyl | 1 | |
| 7.25 | 3-C$_2$H$_5$ | H | H    | H   | 2-cyclopropyl | 1 | |
| 7.26 | 3-CH$_3$  | H    | H    | H   | 2-cyclopropyl | 1 | |
| 7.27 | 3-OCH$_3$ | H    | H    | H   | 2-cyclopropyl | 1 | |
| 7.28 | 3-Cl      | 4-Cl | H    | H   | 2-cyclopropyl | 1 | |
| 7.29 | H         | H    | 3-F  | H   | 2-cyclopropyl | 1 | |
| 7.30 | H         | H    | 3-Cl | H   | 2-cyclopropyl | 1 | |
| 7.31 | 3-F       | H    | 3-F  | H   | 2-cyclopropyl | 1 | |
| 7.32 | 3-Cl      | H    | 3-F  | H   | 2-cyclopropyl | 1 | |
| 7.33 | 3-Br      | H    | 3-F  | H   | 2-cyclopropyl | 1 | |
| 7.34 | H         | H    | H    | CH$_3$ | 2-cyclopropyl | | |
| 7.35 | 3-Br      | H    | H    | CH$_3$ | 2-cyclopropyl | 1 | |
| 7.36 | 3-C$_2$H$_5$ | H | H    | CH$_3$ | 2-cyclopropyl | 1 | |
| 7.37 | 3-OCH$_3$ | H    | H    | CH$_3$ | 2-cyclopropyl | 1 | |
| 7.38 | 3-Cl      | 4-F  | H    | H   | 2-cyclopropyl | 1 | |
| 7.39 | H         | H    | H    | H   | 2-OCH$_3$   | 1 | |
| 7.40 | H         | H    | H    | H   | 2-OC$_2$H$_5$ | 1 | |
| 7.41 | 3-F       | H    | H    | CH$_3$ | 2-OC$_2$H$_5$ | 1 | |
| 7.42 | 3-Cl      | H    | H    | H   | 2-OC$_2$H$_5$ | 1 | |
| 7.43 | 3-Br      | H    | H    | CH$_3$ | 2-OC$_2$H$_5$ | 1 | |
| 7.44 | 3-CF$_3$  | H    | H    | H   | 2-OC$_2$H$_5$ | 1 | |
| 7.45 | 3-CH$_3$  | H    | H    | CH$_3$ | 2-OC$_2$H$_5$ | 1 | |
| 7.46 | 3-C$_2$H$_5$ | H | H    | H   | 2-OC$_2$H$_5$ | 1 | |
| 7.47 | 3-OCH$_3$ | H    | H    | CH$_3$ | 2-OC$_2$H$_5$ | 1 | |
| 7.48 | 3-Cl      | 3-F  | H    | H   | 2-OC$_2$H$_5$ | 1 | |
| 7.49 | H         | H    | H    | H   | 2-Cl        | 1 | |
| 7.50 | 3-F       | H    | H    | CH$_3$ | 2-Cl      | 1 | |
| 7.51 | 3-Cl      | H    | H    | H   | 2-Cl        | 1 | |
| 7.52 | 3-Br      | H    | H    | CH$_3$ | 2-Cl      | 1 | |
| 7.53 | 3-CF$_3$  | H    | H    | H   | 2-Cl        | 1 | |
| 7.54 | 3-CH$_3$  | H    | H    | CH$_3$ | 2-Cl      | 1 | |
| 7.55 | 3-C$_2$H$_5$ | H | H    | H   | 2-Cl        | 1 | |
| 7.56 | 3-OCH$_3$ | H    | H    | CH$_3$ | 2-Cl      | 1 | |
| 7.57 | 3-Cl      | 4-F  | H    | H   | 2-Cl        | 1 | |
| 7.61 | H         | H    | H    | CH$_3$ | 2-cyclopropyl | 1 | |
| 7.62 | H         | H    | H    | CH$_3$ | 2-OCH$_3$ | 1 | |
| 7.63 | H         | H    | H    | CH$_3$ | 2-OC$_2$H$_5$ | 1 | |
| 7.64 | H         | H    | H    | CH$_3$ | 2-Cl      | 1 | |

TABLE 8

Structure: $R^1, R^2$ on first phenyl ring connected via O to second phenyl ring with $R^3$, connected via O—CH$_2$ to a furan ring bearing $(R^5)_n$

| Comp. No. | $R^1$ | $R^2$ | $R^3$ | $R^5$ | n | Phys. data (mp. °C.) |
|---|---|---|---|---|---|---|
| 8.1  | H         | H   | H    | —           | 0 | |
| 8.2  | 3-F       | H   | H    | —           | 0 | |
| 8.3  | 3-Cl      | H   | H    | —           | 0 | |
| 8.4  | 3-Br      | H   | H    | —           | 0 | |
| 8.5  | 3-CF$_3$  | H   | H    | —           | 0 | |
| 8.6  | 3-CH$_3$  | H   | H    | —           | 0 | |
| 8.7  | 3-C$_2$H$_5$ | H | H  | —           | 0 | |
| 8.8  | 3-OCH$_3$ | H   | H    | —           | 0 | |
| 8.9  | 3-Cl      | 4-F | H    | —           | 0 | |
| 8.10 | H         | H   | H    | 2-CH$_3$    | 1 | |
| 8.11 | 3-F       | H   | H    | 2-CH$_3$    | 1 | |
| 8.12 | 3-Cl      | H   | H    | 2-CH$_3$    | 1 | |
| 8.13 | 3-Br      | H   | H    | 2-CH$_3$    | 1 | |
| 8.14 | 3-CF$_3$  | H   | H    | 2-CH$_3$    | 1 | |
| 8.15 | 3-CH$_3$  | H   | H    | 2-CH$_3$    | 1 | |
| 8.16 | 3-C$_2$H$_5$ | H | H  | 2-CH$_3$    | 1 | |
| 8.17 | 3-OCH$_3$ | H   | H    | 2-CH$_3$    | 1 | |
| 8.18 | 3-Cl      | 4-F | H    | 2-CH$_3$    | 1 | |
| 8.19 | H         | H   | 3-F  | 2-CH$_3$    | 1 | |
| 8.20 | H         | H   | 3-Cl | 2-CH$_3$    | 1 | |
| 8.21 | 3-F       | H   | 3-F  | 2-CH$_3$    | 1 | |
| 8.22 | 3-F       | H   | 3-Cl | 2-CH$_3$    | 1 | |
| 8.23 | 3-Cl      | H   | 3-F  | 2-CH$_3$    | 1 | |
| 8.24 | 3-Cl      | H   | 3-Cl | 2-CH$_3$    | 1 | |
| 8.25 | 3-CH$_3$  | H   | 3-F  | 2-CH$_3$    | 1 | |
| 8.26 | 3-CH$_3$  | H   | 3-Cl | 2-CH$_3$    | 1 | |
| 8.27 | H         | H   | H    | 2-cyclopropyl | 1 | |
| 8.28 | 3-F       | H   | H    | 2-cyclopropyl | 1 | |
| 8.29 | 3-Cl      | H   | H    | 2-cyclopropyl | 1 | |
| 8.30 | 3-Br      | H   | H    | 2-cyclopropyl | 1 | |
| 8.31 | 3-CF$_3$  | H   | H    | 2-cyclopropyl | 1 | |
| 8.32 | 3-CH$_3$  | H   | H    | 2-cyclopropyl | 1 | |
| 8.33 | 3-C$_2$H$_5$ | H | H  | 2-cyclopropyl | 1 | |
| 8.34 | 3-OCH$_3$ | H   | H    | 2-cyclopropyl | 1 | |
| 8.35 | 3-Cl      | 4-F | H    | 2-cyclopropyl | 1 | |
| 8.36 | H         | H   | H    | 2-OCH$_3$   | 1 | |
| 8.37 | H         | H   | H    | 2-OC$_2$H$_5$ | 1 | |
| 8.38 | 3-F       | H   | H    | 2-OC$_2$H$_5$ | 1 | |
| 8.39 | 3-Cl      | H   | H    | 2-OC$_2$H$_5$ | 1 | |
| 8.40 | 3-Br      | H   | H    | 2-OC$_2$H$_5$ | 1 | |
| 8.41 | 3-CF$_3$  | H   | H    | 2-OC$_2$H$_5$ | 1 | |
| 8.42 | 3-CH$_3$  | H   | H    | 2-OC$_2$H$_5$ | 1 | |
| 8.42 | 3-C$_2$H$_5$ | H | H  | 2-OC$_2$H$_5$ | 1 | |
| 8.43 | 3-OCH$_3$ | H   | H    | 2-OC$_2$H$_5$ | 1 | |
| 8.44 | 3-Cl      | 4-F | H    | 2-OC$_2$H$_5$ | 1 | |

TABLE 9

Structure: R¹,R² substituted phenyl — O — phenyl(R³) — O — CH(R⁴) — C(=CH-N(R⁶)-N=C-)(R⁵)n (azole ring)

| Comp. No. | R¹ | R² | R³ | R⁴ | R⁵ | R⁶ | n | Phys. data (mp. °C.) |
|---|---|---|---|---|---|---|---|---|
| 9.1 | H | H | H | H | 4-CH₃ | CH₃ | 1 | |
| 9.2 | H | H | H | CH₃ | 4-CH₃ | CH₃ | 1 | |
| 9.3 | 3-F | H | H | H | 4-CH₃ | CH₃ | 1 | |
| 9.4 | 3-Cl | H | H | H | 4-CH₃ | CH₃ | 1 | |
| 9.5 | 3-Br | H | H | H | 4-CH₃ | CH₃ | 1 | |
| 9.6 | 3-CF₃ | H | H | H | 4-CH₃ | CH₃ | 1 | |
| 9.7 | 3-CH₃ | H | H | H | 4-CH₃ | CH₃ | 1 | |
| 9.8 | 3-C₂H₅ | H | H | H | 4-CH₃ | CH₃ | 1 | |
| 9.9 | 3-OCH₃ | H | H | H | 4-CH₃ | CH₃ | 1 | |
| 9.10 | 3-OC₂H₅ | H | H | H | 4-CH₃ | CH₃ | 1 | |
| 9.11 | 4-F | H | H | H | 4-CH₃ | CH₃ | 1 | |
| 9.12 | 3-F | H | H | H | 2,4-dimethyl | CH₃ | 2 | |
| 9.13 | 3-Cl | H | H | H | 2,4-dimethyl | CH₃ | 2 | |
| 9.14 | 3-Br | H | H | H | 2,4-dimethyl | CH₃ | 2 | |
| 9.15 | 3-CF₃ | H | H | H | 2,4-dimethyl | CH₃ | 2 | |
| 9.16 | 3-CH₃ | H | H | H | 2,4-dimethyl | CH₃ | 2 | |
| 9.17 | 3-C₂H₅ | H | H | H | 2,4-dimethyl | CH₃ | 2 | |
| 9.18 | 3-OCH₃ | H | H | H | 2,4-dimethyl | CH₃ | 2 | |
| 9.19 | 3-OC₂H₅ | H | H | H | 2,4-dimethyl | CH₃ | 2 | |
| 9.20 | 4-F | H | H | H | 2,4-dimethyl | CH₃ | 2 | |
| 9.21 | 3-F | H | H | CH₃ | — | CH₃ | 0 | |
| 9.22 | 3-Cl | H | H | CH₃ | — | CH₃ | 0 | |
| 9.23 | 3-Br | H | H | CH₃ | — | CH₃ | 0 | |
| 9.24 | 3-CF₃ | H | H | CH₃ | — | CH₃ | 0 | |
| 9.25 | 3-CH₃ | H | H | CH₃ | — | CH₃ | 0 | |
| 9.26 | 3-C₂H₅ | H | H | CH₃ | — | CH₃ | 0 | |
| 9.27 | 3-OCH₃ | H | H | CH₃ | — | CH₃ | 0 | |
| 9.28 | 3-OC₂H₅ | H | H | CH₃ | — | CH₃ | 0 | |
| 9.29 | 4-F | H | H | CH₃ | — | CH₃ | 0 | |
| 9.30 | 3-F | H | H | CH₃ | 2-CH₃ | CH₃ | 1 | |
| 9.31 | 3-Cl | H | H | CH₃ | 2-CH₃ | CH₃ | 1 | |
| 9.32 | 3-Br | H | H | CH₃ | 2-CH₃ | CH₃ | 1 | |
| 9.33 | 3-CF₃ | H | H | CH₃ | 2-CH₃ | CH₃ | 1 | |
| 9.34 | 3-CH₃ | H | H | CH₃ | 2-CH₃ | CH₃ | 1 | |
| 9.35 | 3-C₂H₅ | H | H | CH₃ | 2-CH₃ | CH₃ | 1 | |
| 9.36 | 3-OCH₃ | H | H | CH₃ | 2-CH₃ | CH₃ | 1 | |
| 9.37 | 3-OC₂H₅ | H | H | CH₃ | 2-CH₃ | CH₃ | 1 | |
| 9.38 | 4-F | H | H | CH₃ | 5-CH₃ | CH₃ | 1 | |
| 9.39 | 3-F | H | 3-F | H | 4-CH₃ | CH₃ | 1 | |
| 9.40 | 3-Cl | H | 3-F | H | 4-CH₃ | CH₃ | 1 | |
| 9.41 | 3-Br | H | 3-F | H | 4-CH₃ | CH₃ | 1 | |
| 9.42 | 3-CF₃ | H | 3-F | H | 4-CH₃ | CH₃ | 1 | |
| 9.43 | 3-CH₃ | H | 3-F | H | 4-CH₃ | CH₃ | 1 | |
| 9.44 | 3-C₂H₅ | H | 3-F | H | 4-CH₃ | CH₃ | 1 | |
| 9.45 | 3-OCH₃ | H | 3-F | H | 4-CH₃ | CH₃ | 1 | |
| 9.46 | 3-OC₂H₅ | H | 3-F | H | 4-CH₃ | CH₃ | 1 | |
| 9.47 | 4-F | H | 3-F | H | 4-CH₃ | CH₃ | 1 | |
| 9.48 | H | H | H | H | 2-cyclopropyl | CH₃ | 1 | |
| 9.49 | 3-F | H | H | H | 2-cyclopropyl | CH₃ | 1 | |
| 9.50 | 3-Cl | H | H | H | 2-cyclopropyl | CH₃ | 1 | |
| 9.51 | 3-Br | H | H | H | 2-cyclopropyl | CH₃ | 1 | |
| 9.52 | 3-CF₃ | H | 3 | H | 2-cyclopropyl | CH₃ | 1 | |
| 9.53 | 3-CH₃ | H | H | H | 2-cyclopropyl | CH₃ | 1 | |
| 9.54 | 3-C₂H₅ | H | H | H | 2-cyclopropyl | CH₃ | 1 | |
| 9.55 | 3-OCH₃ | H | H | H | 2-cyclopropyl | CH₃ | 1 | |
| 9.56 | 4-F | H | H | H | 2-cyclopropyl | CH₃ | 1 | |
| 9.57 | H | H | 3-F | H | 2-cyclopropyl | CH₃ | 1 | |
| 9.58 | H | H | 3-Cl | H | 2-cyclopropyl | CH₃ | 1 | |

TABLE 10

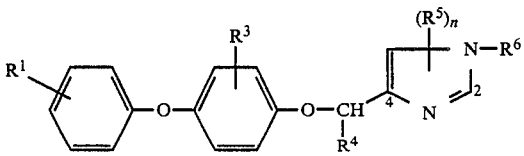

| Comp. No. | R¹ | R³ | R⁴ | R⁵ | R⁶ | n | Phys. data (mp. °C.) |
|---|---|---|---|---|---|---|---|
| 10.1 | H | H | H | — | $CH_3$ | 0 | |
| 10.2 | H | H | $CH_3$ | 5-$CH_3$ | $CH_3$ | 1 | |
| 10.3 | 3-F | H | H | 5-$CH_3$ | $CH_3$ | 1 | |
| 10.4 | 3-Cl | H | H | 5-$CH_3$ | $CH_3$ | 1 | |
| 10.5 | 3-Br | H | H | 5-$CH_3$ | $CH_3$ | 1 | |
| 10.6 | 3-$CF_3$ | H | H | 5-$CH_3$ | $CH_3$ | 1 | |
| 10.7 | 3-$CH_3$ | H | H | 5-$CH_3$ | $CH_3$ | 1 | |
| 10.8 | 3-$C_2H_5$ | H | H | 5-$CH_3$ | $CH_3$ | 1 | |
| 10.9 | 3-$OCH_3$ | H | H | 5-$CH_3$ | $CH_3$ | 1 | |
| 10.10 | 3-$OC_2H_5$ | H | H | 5-$CH_3$ | $CH_3$ | 1 | |
| 10.11 | 4-F | H | H | 5-$CH_3$ | $CH_3$ | 1 | |
| 10.12 | 3-F | H | H | 2-$CH_3$ | $CH_3$ | 1 | |
| 10.13 | 3-Cl | H | H | 2-$CH_3$ | $CH_3$ | 1 | |
| 10.14 | 3-Br | H | H | 2-$CH_3$ | $CH_3$ | 1 | |
| 10.15 | 3-$CF_3$ | H | H | 2-$CH_3$ | $CH_3$ | 1 | |
| 10.16 | 3-$CH_3$ | H | H | 2-$CH_3$ | $CH_3$ | 1 | |
| 10.17 | 3-$C_2H_5$ | H | H | 2-$CH_3$ | $CH_3$ | 1 | |
| 10.18 | 3-$OCH_3$ | H | H | 2-$CH_3$ | $CH_3$ | 1 | |
| 10.19 | 3-$OC_2H_5$ | H | H | 2-$CH_3$ | $CH_3$ | 1 | |
| 10.20 | 4-F | H | H | — | $CH_3$ | 0 | |
| 10.21 | 3-F | H | $CH_3$ | 5-$CH_3$ | $CH_3$ | 1 | |
| 10.22 | 3-Cl | H | $CH_3$ | 5-$CH_3$ | $CH_3$ | 1 | |
| 10.23 | 3-Br | H | $CH_3$ | 5-$CH_3$ | $CH_3$ | 1 | |
| 10.24 | 3-$CF_3$ | H | $CH_3$ | 5-$CH_3$ | $CH_3$ | 1 | |
| 10.25 | 3-$CH_3$ | H | $CH_3$ | 5-$CH_3$ | $CH_3$ | 1 | |
| 10.26 | 3-$C_2H_5$ | H | $CH_3$ | 5-$CH_3$ | $CH_3$ | 1 | |
| 10.27 | 3-$OCH_3$ | H | $CH_3$ | 5-$CH_3$ | $CH_3$ | 1 | |
| 10.28 | 3-$OC_2H_5$ | H | $CH_3$ | 5-$CH_3$ | $CH_3$ | 1 | |
| 10.29 | 4-F | H | $CH_3$ | 5-$CH_3$ | $CH_3$ | 1 | |
| 10.30 | 3-F | H | $CH_3$ | 2-$CH_3$ | $CH_3$ | 1 | |
| 10.31 | 3-Cl | H | $CH_3$ | 2-$CH_3$ | $CH_3$ | 1 | |
| 10.32 | 3-Br | H | $CH_3$ | 2-$CH_3$ | $CH_3$ | 1 | |
| 10.33 | 3-$CF_3$ | H | $CH_3$ | 2-$CH_3$ | $CH_3$ | 1 | |
| 10.34 | 3-$CH_3$ | H | $CH_3$ | 2-$CH_3$ | $CH_3$ | 1 | |
| 10.35 | 3-$C_2H_5$ | H | $CH_3$ | 2-$CH_3$ | $CH_3$ | 1 | |
| 10.36 | 3-$OCH_3$ | H | $CH_3$ | 2-$CH_3$ | $CH_3$ | 1 | |
| 10.37 | 3-$OC_2H_5$ | H | $CH_3$ | 2-$CH_3$ | $CH_3$ | 1 | |
| 10.38 | 4-F | H | $CH_3$ | 2-$CH_3$ | $CH_3$ | 1 | |
| 10.39 | 3-F | 3-F | H | 5-$CH_3$ | $CH_3$ | 1 | |
| 10.40 | 3-Cl | 3-F | H | 5-$CH_3$ | $CH_3$ | 1 | |
| 10.41 | 3-Br | 3-F | H | 5-$CH_3$ | $CH_3$ | 1 | |
| 10.42 | 3-$CF_3$ | 3-F | H | 5-$CH_3$ | $CH_3$ | 1 | |
| 10.43 | 3-$CH_3$ | 3-F | H | 5-$CH_3$ | $CH_3$ | 1 | |
| 10.44 | 3-$C_2H_5$ | 3-F | H | 5-$CH_3$ | $CH_3$ | 1 | |
| 10.45 | 3-$OCH_3$ | 3-F | H | 5-$CH_3$ | $CH_3$ | 1 | |
| 10.46 | 3-$OC_2H_5$ | 3-F | H | 5-$CH_3$ | $CH_3$ | 1 | |
| 10.47 | 4-F | 3-F | H | 5-$CH_3$ | $CH_3$ | 1 | |
| 10.48 | H | H | H | 2-cyclopropyl | $CH_3$ | 1 | |
| 10.49 | 3-F | H | H | 2-cyclopropyl | $CH_3$ | 1 | |
| 10.50 | 3-Cl | H | H | 2-cyclopropyl | $CH_3$ | 1 | |
| 10.51 | 3-Br | H | H | 2-cyclopropyl | $CH_3$ | 1 | |
| 10.52 | 3-$CF_3$ | H | H | 2-cyclopropyl | $CH_3$ | 1 | |
| 10.53 | 3-$CH_3$ | H | H | 2-cyclopropyl | $CH_3$ | 1 | |
| 10.54 | 3-$C_2H_5$ | H | H | 2-cyclopropyl | $CH_3$ | 1 | |
| 10.55 | 3-$OCH_2$ | H | H | 2-cyclopropyl | $CH_3$ | 1 | |
| 10.56 | H | H | H | 2-cyclopropyl | cyclopropyl | 1 | |
| 10.57 | H | 3-F | H | 2-cyclopropyl | $CH_3$ | 1 | |
| 10.58 | 3-$C_2H_5$ | 3-F | H | 2-cyclopropyl | $CH_3$ | 1 | |
| 10.59 | H | H | H | 2-$CH_3$ | cyclopropyl | 1 | |
| 10.60 | 3-$C_2H_5$ | H | H | 2-$CH_3$ | cyclopropyl | 1 | |

TABLE 11

| Comp. No. | R¹ | R² | R³ | R⁴ | R⁵ | n | Phys. data (mp. °C.) |
|---|---|---|---|---|---|---|---|
| 11.1 | H | H | H | H | — | 0 | |
| 11.2 | H | H | H | CH₃ | — | 0 | |
| 11.3 | 3-F | H | H | H | — | 0 | |
| 11.4 | 3-Cl | H | H | H | — | 0 | |
| 11.5 | 3-Br | H | H | H | — | 0 | |
| 11.6 | 3-CF₃ | H | H | H | — | 0 | |
| 11.7 | 3-CH₃ | H | H | H | — | 0 | |
| 11.8 | 3-C₂H₅ | H | H | H | — | 0 | |
| 11.9 | 3-OCH₃ | H | H | H | — | 0 | |
| 11.10 | 3-Cl | 4-F | H | H | — | 0 | |
| 11.11 | H | H | H | H | 2-CH₃ | 1 | 67–68 |
| 11.12 | H | H | H | CH₃ | 2-CH₃ | 1 | |
| 11.13 | 3-F | H | H | H | 2-CH₃ | 1 | 300-MHz ¹H-NMR in CDCl₃ [ppm]: 2.72(s) |
| 11.14 | 3-Cl | H | H | H | 2-CH₃ | 1 | |
| 11.15 | 3-Br | H | H | H | 2-CH₃ | 1 | |
| 11.16 | 3-CF₃ | H | H | H | 2-CH₃ | 1 | 73–74 |
| 11.17 | 3-CH₃ | H | H | H | 2-CH₃ | 1 | |
| 11.18 | 3-C₂H₅ | H | H | H | 2-CH₃ | 1 | |
| 11.19 | 3-OCH₃ | H | H | H | 2-CH₃ | 1 | |
| 11.20 | 3-Cl | 4-F | H | H | 2-CH₃ | 1 | 96–99 |
| 11.21 | 3-F | H | 3-F | H | 2-CH₃ | 1 | |
| 11.22 | 3-Cl | H | 3-Cl | H | 2-CH₃ | 1 | |
| 11.23 | 3-CF₃ | H | 3-F | H | 2-CH₃ | 1 | |
| 11.24 | 3-CH₃ | H | 3-Cl | H | 2-CH₃ | 1 | |
| 11.25 | 3-C₂H₅ | H | 3-F | H | 2-CH₃ | 1 | |
| 11.26 | 3-OCH₃ | H | 3-Cl | H | 2-CH₃ | 1 | |
| 11.27 | 3-Cl | 4-F | 3-F | H | 2-CH₃ | 1 | |
| 11.28 | H | H | H | H | 2-cyclopropyl | 1 | 300-MHz-¹H-NMR in CDCl₃ [ppm]: 5.08 (s) |
| 11.29 | H | H | H | CH₃ | 2-cyclopropyl | 1 | |
| 11.30 | 3-F | H | H | H | 2-cyclopropyl | 1 | |
| 11.31 | 3-Cl | H | H | H | 2-cyclopropyl | 1 | |
| 11.32 | 3-Br | H | H | H | 2-cyclopropyl | 1 | |
| 11.33 | 3-CF₃ | H | H | H | 2-cyclopropyl | 1 | |
| 11.34 | 3-CH₃ | H | H | H | 2-cyclopropyl | 1 | |
| 11.35 | 3-C₂H₅ | H | H | H | 2-cyclopropyl | 1 | |
| 11.36 | 3-OCH₃ | H | H | H | 2-cyclopropyl | 1 | |
| 11.37 | 3-Cl | 4-F | H | H | 2-cyclopropyl | 1 | |
| 11.38 | 3-F | H | 3-F | H | 2-cyclopropyl | 1 | |
| 11.39 | 3-Cl | H | 3-Cl | H | 2-cyclopropyl | 1 | |
| 11.40 | 3-CF₃ | H | 3-F | H | 2-cyclopropyl | 1 | |
| 11.41 | 3-CH₃ | H | 3-Cl | H | 2-cyclopropyl | 1 | |
| 11.42 | 3-C₂H₅ | H | 3-F | H | 2-cyclopropyl | 1 | |
| 11.43 | 3-OCH₃ | H | 3-Cl | H | 2-cyclopropyl | 1 | |
| 11.44 | 3-Cl | 4-F | 3-F | H | 2-cyclopropyl | 1 | |
| 11.45 | H | H | H | H | 2-Cl | 1 | |
| 11.46 | H | H | H | CH₃ | 2-Cl | 1 | |
| 11.47 | 3-F | H | H | H | 2-Cl | 1 | |
| 11.48 | 3-Cl | H | H | H | 2-Cl | 1 | |
| 11.49 | 3-Br | H | H | H | 2-Cl | 1 | |
| 11.50 | 3-CF₃ | H | H | H | 2-Cl | 1 | |
| 11.51 | 3-CH₃ | H | H | H | 2-Cl | 1 | |
| 11.52 | 3-C₂H₅ | H | H | H | 2-Cl | 1 | |
| 11.53 | 3-OCH₃ | H | H | H | 2-Cl | 1 | |
| 11.54 | 3-Cl | 4-F | H | H | 2-Cl | 1 | |
| 11.55 | H | H | H | H | 2-OCH₃ | 1 | |
| 11.56 | H | H | H | CH₃ | 2-OCH₃ | 1 | |
| 11.57 | H | H | H | H | 2-OC₂H₅ | 1 | |
| 11.58 | H | H | H | CH₃ | 2-OC₂H₅ | 1 | |
| 11.59 | 3-F | H | H | H | 2-OC₂H₅ | 1 | |
| 11.60 | 3-Cl | H | H | H | 2-OC₂H₅ | 1 | |
| 11.61 | 3-Br | H | H | H | 2-OC₂H₅ | 1 | |
| 11.62 | 3-CF₃ | H | H | H | 2-OC₂H₅ | 1 | |
| 11.63 | 3-CH₃ | H | H | H | 2-OC₂H₅ | 1 | |
| 11.64 | 3-C₂H₅ | H | H | H | 2-OC₂H₅ | 1 | |
| 11.65 | 3-OCH₃ | H | H | H | 2-OC₂H₅ | 1 | |

TABLE 11-continued

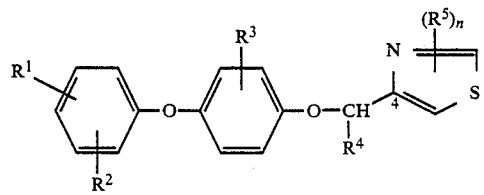

| Comp. No. | R¹ | R² | R³ | R⁴ | R⁵ | n | Phys. data (mp. °C.) |
|---|---|---|---|---|---|---|---|
| 11.66 | 3-Cl | 4-F | H | H | 2-OC$_2$H$_5$ | 1 | |

TABLE 12

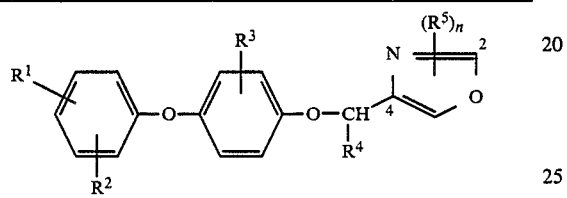

| Comp. No. | R¹ | R² | R³ | R⁴ | R⁵ | n | Phys. data (mp. °C.) |
|---|---|---|---|---|---|---|---|
| 12.1 | H | H | H | H | — | 0 | |
| 12.2 | H | H | H | CH$_3$ | — | 0 | |
| 12.3 | 3-F | H | H | H | — | 0 | |
| 12.4 | 3-Cl | H | H | H | — | 0 | |
| 12.5 | 3-Br | H | H | H | — | 0 | |
| 12.6 | 3-CF$_3$ | H | H | H | — | 0 | |
| 12.7 | 3-CH$_3$ | H | H | H | — | 0 | |
| 12.8 | 3-C$_2$H$_5$ | H | H | H | — | 0 | |
| 12.9 | 3-OCH$_3$ | H | H | H | — | 0 | |
| 12.10 | 3-Cl | 4-F | H | H | — | 0 | |
| 12.11 | H | H | H | H | 2-CH$_3$ | 1 | |
| 12.12 | H | H | H | CH$_3$ | 2-CH$_3$ | 1 | |
| 12.13 | 3-F | H | H | H | 2-CH$_3$ | 1 | |
| 12.14 | 3-Cl | H | H | H | 2-CH$_3$ | 1 | |
| 12.15 | 3-Br | H | H | H | 2-CH$_3$ | 1 | |
| 12.16 | 3-CF$_3$ | H | H | H | 2-CH$_3$ | 1 | |
| 12.17 | 3-CH$_3$ | H | H | H | 2-CH$_3$ | 1 | |
| 12.18 | 3-C$_2$H$_5$ | H | H | H | 2-CH$_3$ | 1 | |
| 12.19 | 3-OCH$_3$ | H | H | H | 2-CH$_3$ | 1 | |
| 12.20 | 3-Cl | 4-F | H | H | 2-CH$_3$ | 1 | |
| 12.21 | H | H | 3-F | H | 2-CH$_3$ | 1 | |
| 12.22 | H | H | 3-Cl | H | 2-CH$_3$ | 1 | |
| 12.23 | 3-F | H | 3-F | H | 2-CH$_3$ | 1 | |
| 12.24 | 3-Cl | H | 3-Cl | H | 2-CH$_3$ | 1 | |
| 12.25 | 3-CH$_3$ | H | 3-F | H | 2-CH$_3$ | 1 | |
| 12.26 | 3-CH$_3$ | H | 3-Cl | H | 2-CH$_3$ | 1 | |
| 12.27 | H | H | H | H | 2-cyclopropyl | 1 | |
| 12.28 | H | H | H | CH$_3$ | 2-cyclopropyl | 1 | |
| 12.29 | 3-F | H | H | H | 2-cyclopropyl | 1 | |
| 12.30 | 3-Cl | H | H | H | 2-cyclopropyl | 1 | |
| 12.31 | 3-Br | H | H | H | 2-cyclopropyl | 1 | |
| 12.32 | 3-CF$_3$ | H | H | H | 2-cyclopropyl | 1 | |
| 12.33 | 3-CH$_3$ | H | H | H | 2-cyclopropyl | 1 | |
| 12.34 | 3-C$_2$H$_5$ | H | H | H | 2-cyclopropyl | 1 | |
| 12.35 | 3-OCH$_3$ | H | H | H | 2-cyclopropyl | 1 | |
| 12.36 | 3-Cl | 4-F | H | H | 2-cyclopropyl | 1 | |
| 12.37 | H | H | H | H | 2-OCH$_3$ | 1 | |
| 12.38 | H | H | H | H | 2-OC$_2$H$_5$ | 1 | |
| 12.39 | 3-F | H | H | H | 2-OC$_2$H$_5$ | 1 | |
| 12.40 | 3-Cl | H | H | H | 2-OC$_2$H$_5$ | 1 | |
| 12.41 | 3-Br | H | H | H | 2-OC$_2$H$_5$ | 1 | |
| 12.42 | 3-CF$_3$ | H | H | H | 2-OC$_2$H$_5$ | 1 | |
| 12.43 | 3-CH$_3$ | H | H | H | 2-OC$_2$H$_5$ | 1 | |
| 12.44 | 3-C$_2$H$_5$ | H | H | H | 2-OC$_2$H$_5$ | 1 | |
| 12.45 | 3-OCH$_3$ | H | H | H | 2-OC$_2$H$_5$ | 1 | |
| 12.46 | 3-Cl | 4-F | H | H | 2-OC$_2$H$_5$ | 1 | |

TABLE 13

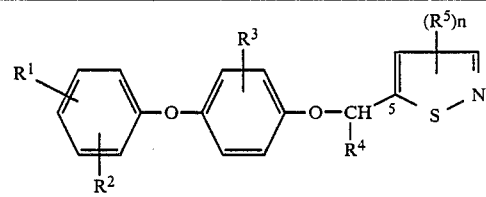

| Comp. No. | R¹ | R² | R³ | R⁴ | R⁵ | n | Phys. data (mp. °C.) |
|---|---|---|---|---|---|---|---|
| 13.1 | H | H | H | H | — | 0 | |
| 13.2 | 3-F | H | H | H | — | 0 | |
| 13.3 | 3-Cl | H | H | H | — | 0 | |
| 13.4 | 3-Br | H | H | H | — | 0 | |
| 13.5 | 3-CF$_3$ | H | H | H | — | 0 | |
| 13.6 | 3-CH$_3$ | H | H | H | — | 0 | |
| 13.7 | 3-C$_2$H$_5$ | H | H | H | — | 0 | |
| 13.8 | 3-OCH$_3$ | H | H | H | — | 0 | |
| 13.9 | 3-Cl | 4-F | H | H | — | 0 | |
| 13.10 | H | H | H | H | 3-CH$_3$ | 1 | 61–64 |
| 13.11 | 3-F | H | H | H | 3-CH$_3$ | 1 | |
| 13.12 | 3-Cl | H | H | H | 3-CH$_3$ | 1 | |
| 13.13 | 3-Br | H | H | H | 3-CH$_3$ | 1 | |
| 13.14 | 3-CH$_3$ | H | H | H | 3-CH$_3$ | 1 | |
| 13.15 | 3-C$_2$H$_5$ | H | H | H | 3-CH$_3$ | 1 | |
| 13.16 | 3-OCH$_3$ | H | H | H | 3-CH$_3$ | 1 | |
| 13.17 | 3-Cl | 4-F | H | H | 3-CH$_3$ | 1 | |
| 13.18 | 3-CF$_3$ | H | H | H | 3-cyclopropyl | 1 | |
| 13.19 | 3-F | H | H | H | 3-cyclopropyl | 1 | |
| 13.20 | 3-Cl | H | H | H | 3-cyclopropyl | 1 | |
| 13.21 | 3-Br | H | H | H | 3-cyclopropyl | 1 | |
| 13.22 | 3-CF$_3$ | H | H | H | 3-cyclopropyl | 1 | |
| 13.23 | 3-CH$_3$ | H | H | H | 3-cyclopropyl | 1 | |
| 13.24 | 3-C$_2$H$_5$ | H | H | H | 3-cyclopropyl | 1 | |
| 13.25 | 3-OCH$_3$ | H | H | H | 3-cyclopropyl | 1 | |
| 13.26 | 3-Cl | 4-F | H | H | 3-cyclopropyl | 1 | |
| 13.27 | H | H | H | CH$_3$ | 3-CH$_3$ | 1 | |
| 13.28 | H | H | 3-F | H | — | 0 | |
| 13.29 | H | H | 3-F | H | 3-CH$_3$ | 1 | |
| 13.30 | H | H | 3-F | H | 3-cyclopropyl | 1 | |
| 13.31 | H | H | H | CH$_3$ | 3-cyclopropyl | 1 | |
| 13.32 | H | H | H | H | 3-OC$_2$H$_5$ | 1 | |
| 13.33 | 3-F | H | H | H | 3-OC$_2$H$_5$ | 1 | |
| 13.34 | 3-Cl | H | H | H | 3-OC$_2$H$_5$ | 1 | |
| 13.35 | 3-Br | H | H | H | 3-OC$_2$H$_5$ | 1 | |
| 13.36 | 3-CF$_3$ | H | H | H | 3-OC$_2$H$_5$ | 1 | |
| 13.37 | 3-CH$_3$ | H | H | H | 3-OC$_2$H$_5$ | 1 | |
| 13.38 | 3-C$_2$H$_5$ | H | H | H | 3-OC$_2$H$_5$ | 1 | |
| 13.39 | 3-Cl | 4-F | H | H | 3-OC$_2$H$_5$ | 1 | |

TABLE 14

Structure: $R^1, R^2$-phenyl-O-phenyl($R^3$)-O-CH($R^4$)-pyrazole($(R^5)_n$, $R^6$)

| Comp. No. | $R^1$ | $R^2$ | $R^3$ | $R^4$ | $R^5$ | $R^6$ | n | Phys. data (mp. °C.) |
|---|---|---|---|---|---|---|---|---|
| 14.1 | H | H | H | H | — | $CH_3$ | 0 | |
| 14.2 | H | H | H | $CH_3$ | 4-$CH_3$ | $CH_3$ | 1 | |
| 14.3 | 3-F | H | H | H | 4-$CH_3$ | $CH_3$ | 1 | |
| 14.4 | 3-Cl | H | H | H | 4-$CH_3$ | $CH_3$ | 1 | |
| 14.5 | 3-Br | H | H | H | 4-$CH_3$ | $CH_3$ | 1 | |
| 14.6 | 3-$CF_3$ | H | H | H | 4-$CH_3$ | $CH_3$ | 1 | |
| 14.7 | 3-$CH_3$ | H | H | H | 4-$CH_3$ | $CH_3$ | 1 | |
| 14.8 | 3-$C_2H_5$ | H | H | H | 4-$CH_3$ | $CH_3$ | 1 | |
| 14.9 | 3-$OCH_3$ | H | H | H | 4-$CH_3$ | $CH_3$ | 1 | |
| 14.10 | 3-$OC_2H_5$ | H | H | H | 4-$CH_3$ | $CH_3$ | 1 | |
| 14.11 | 4-F | H | H | H | 4-$CH_3$ | $CH_3$ | 1 | |
| 14.12 | 3-F | H | H | H | 3-$CH_3$ | $CH_3$ | 1 | |
| 14.13 | 3-Cl | H | H | H | 3-$CH_3$ | $CH_3$ | 1 | |
| 14.14 | 3-Br | H | H | H | 3-$CH_3$ | $CH_3$ | 1 | |
| 14.15 | 3-$CF_3$ | H | H | H | 3-$CH_3$ | $CH_3$ | 1 | |
| 14.16 | 3-$CH_3$ | H | H | H | 3-$CH_3$ | $CH_3$ | 1 | |
| 14.17 | 3-$C_2H_5$ | H | H | H | 3-$CH_3$ | $CH_3$ | 1 | |
| 14.18 | 3-$OCH_3$ | H | H | H | 3-$CH_3$ | $CH_3$ | 1 | |
| 14.19 | 3-$OC_2H_5$ | H | H | H | 5-$CH_3$ | $CH_3$ | 1 | |
| 14.20 | 4-F | H | H | H | 3-$CH_3$ | $CH_3$ | 1 | |
| 14.21 | 3-F | H | H | $CH_3$ | 4-$CH_3$ | $CH_3$ | 1 | |
| 14.22 | 3-Cl | H | H | $CH_3$ | 4-$CH_3$ | $CH_3$ | 1 | |
| 14.23 | 3-Br | H | H | $CH_3$ | 4-$CH_3$ | $CH_3$ | 1 | |
| 14.24 | 3-$CF_3$ | H | H | $CH_3$ | 4-$CH_3$ | $CH_3$ | 1 | |
| 14.25 | 3-$CH_3$ | H | H | $CH_3$ | 4-$CH_3$ | $CH_3$ | 1 | |
| 14.26 | 3-$C_2H_5$ | H | H | $CH_3$ | 4-$CH_3$ | $CH_3$ | 1 | |
| 14.27 | 3-$OCH_3$ | H | H | $CH_3$ | 4-$CH_3$ | $CH_3$ | 1 | |
| 14.28 | 3-$OC_2H_5$ | H | H | $CH_3$ | 4-$CH_3$ | $CH_3$ | 1 | |
| 14.29 | 4-F | H | H | $CH_3$ | 4-$CH_3$ | $CH_3$ | 1 | |
| 14.30 | 3-F | H | H | $CH_3$ | 3-$CH_3$ | $CH_3$ | 1 | |
| 14.31 | 3-Cl | H | H | $CH_3$ | 3-$CH_3$ | $CH_3$ | 1 | |
| 14.32 | 3-Br | H | H | $CH_3$ | 3-$CH_3$ | $CH_3$ | 1 | |
| 14.33 | 3-$CF_3$ | H | H | $CH_3$ | 3-$CH_3$ | $CH_3$ | 1 | |
| 14.34 | 3-$CH_3$ | H | H | $CH_3$ | 3-$CH_3$ | $CH_3$ | 1 | |
| 14.35 | 3-$C_2H_5$ | H | H | $CH_3$ | 3-$CH_3$ | $CH_3$ | 1 | |
| 14.36 | 3-$OCH_3$ | H | H | $CH_3$ | 3-$CH_3$ | $CH_3$ | 1 | |
| 14.37 | 3-$OC_2H_5$ | H | H | $CH_3$ | 3-$CH_3$ | $CH_3$ | 1 | |
| 14.38 | 4-F | H | H | $CH_3$ | 3-$CH_3$ | $CH_3$ | 1 | |
| 14.39 | 3-F | H | 3-F | H | 4-$CH_3$ | $CH_3$ | 1 | |
| 14.40 | 3-Cl | H | 3-F | H | 4-$CH_3$ | $CH_3$ | 1 | |
| 14.41 | 3-Br | H | 3-F | H | 4-$CH_3$ | $CH_3$ | 1 | |
| 14.42 | 3-$CF_3$ | H | 3-F | H | 4-$CH_3$ | $CH_3$ | 1 | |
| 14.43 | 3-$CH_3$ | H | 3-F | H | 4-$CH_3$ | $CH_3$ | 1 | |
| 14.44 | 3-$C_2H_5$ | H | 3-F | H | 4-$CH_3$ | $CH_3$ | 1 | |
| 14.45 | 3-$OCH_3$ | H | 3-F | H | 4-$CH_3$ | $CH_3$ | 1 | |
| 14.46 | 3-$OC_2H_5$ | H | 3-F | H | 4-$CH_3$ | $CH_3$ | 1 | |
| 14.47 | 4-F | H | 3-F | H | 4-$CH_3$ | $CH_3$ | 1 | |
| 14.48 | H | H | H | H | 3-cyclopropyl | $CH_3$ | 1 | 87–89 |
| 14.49 | 4-F | H | H | H | 3-cyclopropyl | $CH_3$ | 1 | |
| 14.50 | 3-Cl | H | H | H | 3-cyclopropyl | $CH_3$ | 1 | |
| 14.51 | 3-Br | H | H | H | 3-cyclopropyl | $CH_3$ | 1 | |
| 14.52 | 3-$CF_3$ | H | H | H | 3-cyclopropyl | $CH_3$ | 1 | 96–99 |
| 14.53 | 3-$OCH_3$ | H | H | H | 3-cyclopropyl | $CH_3$ | 1 | |
| 14.54 | 3-$CH_3$ | H | H | H | 3-cyclopropyl | $CH_3$ | 1 | |
| 14.55 | 3-$C_2H_5$ | H | H | H | 3-cyclopropyl | $CH_3$ | 1 | |
| 14.56 | 3-Cl | 4-F | H | H | 3-cyclopropyl | $CH_3$ | 1 | |
| 14.57 | H | H | 3-F | H | 3-cyclopropyl | $CH_3$ | 1 | |
| 14.58 | H | H | H | H | 3-$CH_3$ | cyclo-propyl | 1 | |
| 14.59 | 3-F | H | H | H | 3-cyclopropyl | $CH_3$ | 1 | 85–87 |

TABLE 15

Structure: R¹-phenyl-O-phenyl(R³)-O-CH(R⁴)-C(=N-N(R⁶))-pyrazoline with (R⁵)n, with R² on first ring.

| Comp. No. | R¹ | R² | R³ | R⁴ | R⁵ | R⁶ | n | Phys. data (mp. °C.) |
|---|---|---|---|---|---|---|---|---|
| 15.1 | H | H | H | H | — | CH₃ | 0 | |
| 15.2 | H | H | H | CH₃ | 4-CH₃ | CH₃ | 1 | |
| 15.3 | 3-F | H | H | H | 4-CH₃ | CH₃ | 1 | |
| 15.4 | 3-Cl | H | H | H | 4-CH₃ | CH₃ | 1 | |
| 15.5 | 3-Br | H | H | H | 4-CH₃ | CH₃ | 1 | |
| 15.6 | 3-CF₃ | H | H | H | 4-CH₃ | CH₃ | 1 | |
| 15.7 | 3-CH₃ | H | H | H | 4-CH₃ | CH₃ | 1 | |
| 15.8 | 3-C₂H₅ | H | H | H | 4-CH₃ | CH₃ | 1 | |
| 15.9 | 3-OCH₃ | H | H | H | 4-CH₃ | CH₃ | 1 | |
| 15.10 | 3-OC₂H₅ | H | H | H | 4-CH₃ | CH₃ | 1 | |
| 15.11 | 4-F | H | H | H | 4-CH₃ | CH₃ | 1 | |
| 15.12 | 3-F | H | H | H | 4-OCH₃ | CH₃ | 1 | |
| 15.13 | 3-Cl | H | H | H | 4-OCH₃ | CH₃ | 1 | |
| 15.14 | 3-Br | H | H | H | 4-OCH₃ | CH₃ | 1 | |
| 15.15 | 3-CF₃ | H | H | H | 4-OCH₃ | CH₃ | 1 | |
| 15.16 | 3-CH₃ | H | H | H | 4-OCH₃ | CH₃ | 1 | |
| 15.17 | 3-C₂H₅ | H | H | H | 4-OCH₃ | CH₃ | 1 | |
| 15.18 | 3-OCH₃ | H | H | H | 4-OCH₃ | CH₃ | 1 | |
| 15.19 | 3-OC₂H₅ | H | H | H | 4-OCH₃ | CH₃ | 1 | |
| 15.20 | 4-F | H | H | H | 4-OCH₃ | CH₃ | 1 | |
| 15.21 | 3-F | H | H | CH₃ | 4-CH₃ | CH₃ | 1 | |
| 15.22 | 3-Cl | H | H | CH₃ | 4-CH₃ | CH₃ | 1 | |
| 15.23 | 3-Br | H | H | CH₃ | 4-CH₃ | CH₃ | 1 | |
| 15.24 | 3-CF₃ | H | H | CH₃ | 4-CH₃ | CH₃ | 1 | |
| 15.25 | 3-CH₃ | H | H | CH₃ | 4-CH₃ | CH₃ | 1 | |
| 15.26 | 3-C₂H₅ | H | H | CH₃ | 4-CH₃ | CH₃ | 1 | |
| 15.27 | 3-OCH₃ | H | H | CH₃ | 4-CH₃ | CH₃ | 1 | |
| 15.28 | 3-OC₂H₅ | H | H | CH₃ | 4-CH₃ | CH₃ | 1 | |
| 15.29 | 4-F | H | H | CH₃ | 4-CH₃ | CH₃ | 1 | |
| 15.30 | 3-F | H | H | CH₃ | 4-OCH₃ | CH₃ | 1 | |
| 15.31 | 3-Cl | H | H | CH₃ | 4-OCH₃ | CH₃ | 1 | |
| 15.32 | 3-Br | H | H | CH₃ | 4-OCH₃ | CH₃ | 1 | |
| 15.33 | 3-CF₃ | H | H | CH₃ | 4-OCH₃ | CH₃ | 1 | |
| 15.34 | 3-CH₃ | H | H | CH₃ | 4-OCH₃ | CH₃ | 1 | |
| 15.35 | 3-C₂H₅ | H | H | CH₃ | 4-OCH₃ | CH₃ | 1 | |
| 15.36 | 3-OCH₃ | H | H | CH₃ | 4-OCH₃ | CH₃ | 1 | |
| 15.37 | 3-OC₂H₅ | H | H | CH₃ | 4-OCH₃ | CH₃ | 1 | |
| 15.38 | 4-F | H | H | CH₃ | 4-OCH₃ | CH₃ | 1 | |
| 15.39 | 3-F | H | 3-F | H | 5-CH₃ | CH₃ | 1 | |
| 15.40 | 3-Cl | H | 3-F | H | 5-CH₃ | CH₃ | 1 | |
| 15.41 | 3-Br | H | 3-F | H | 5-CH₃ | CH₃ | 1 | |
| 15.42 | 3-CF₃ | H | 3-F | H | 5-CH₃ | CH₃ | 1 | |
| 15.43 | 3-CH₃ | H | 3-F | H | 5-CH₃ | CH₃ | 1 | |
| 15.44 | 3-C₂H₅ | H | 3-F | H | 5-CH₃ | CH₃ | 1 | |
| 15.45 | 3-OCH₃ | H | 3-F | H | 5-CH₃ | CH₃ | 1 | |
| 15.46 | 3-OC₂H₅ | H | 3-F | H | 5-CH₃ | CH₃ | 1 | |
| 15.47 | 4-F | H | 3-F | H | 5-CH₃ | CH₃ | 1 | |
| 15.48 | H | H | H | H | 5-i-C₃H₇ | CH₃ | 1 | 300-MHz-¹H-NMR in CDCl₃ [ppm]: 4.98 (s) |
| 15.49 | H | H | H | H | 5-cyclopropyl | CH₃ | 1 | 57–58 |
| 15.50 | 3-F | H | H | H | 5-cyclopropyl | CH₃ | 1 | 46–48 |
| 15.51 | 3-Cl | H | H | H | 5-cyclopropyl | CH₃ | 1 | |
| 15.52 | 3-Br | H | H | H | 5-cyclopropyl | CH₃ | 1 | |
| 15.53 | 3-CF₃ | H | H | H | 5-cyclopropyl | CH₃ | 1 | 57–58 |
| 15.54 | 3-OCH₃ | H | H | H | 5-cyclopropyl | CH₃ | 1 | |
| 15.55 | 3-CH₃ | H | H | H | 5-cyclopropyl | CH₃ | 1 | |
| 15.56 | 3-C₂H₅ | H | H | H | 5-cyclopropyl | CH₃ | 1 | |
| 15.57 | 3-Cl | 4-F | H | H | 5-cyclopropyl | CH₃ | 1 | |
| 15.58 | H | H | H | H | 5-CH₃ | cyclopropyl | 1 | |
| 15.59 | 3-Br | H | H | H | 5-CH₃ | cyclopropyl | 1 | |
| 15.60 | 3-C₂H₅ | H | H | H | 5-CH₃ | cyclopropyl | 1 | |

TABLE 16

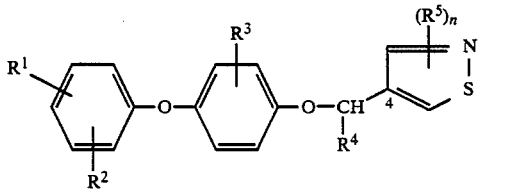

| Comp. No. | R¹ | R² | R³ | R⁴ | R⁵ | n | Phys. data (mp. °C.) |
|---|---|---|---|---|---|---|---|
| 16.1 | H | H | H | H | 3-CH₃ | 1 | 57–60 |
| 16.2 | 3-F | H | H | H | 3-CH₃ | 1 | |
| 16.3 | 3-Cl | H | H | H | 3-CH₃ | 1 | |
| 16.4 | 3-Br | H | H | H | 3-CH₃ | 1 | |
| 16.5 | 3-OCH₃ | H | H | H | 3-CH₃ | 1 | |
| 16.6 | 3-CF₃ | H | H | H | 3-CH₃ | 1 | |
| 16.7 | 3-CH₃ | H | H | H | 3-CH₃ | 1 | |
| 16.8 | 3-C₂H₅ | H | H | H | 3-CH₃ | 1 | |

TABLE 17

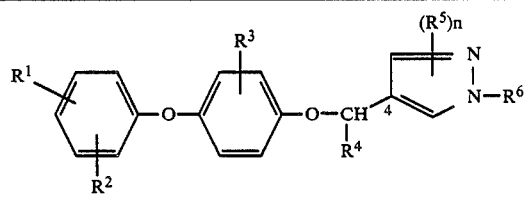

| Comp. No. | R¹ | R³ | R⁴ | R⁵ | R⁶ | n | Phys. data (mp. °C.) |
|---|---|---|---|---|---|---|---|
| 17.1 | H | H | H | — | CH₃ | 0 | 90–91 |
| 17.2 | H | H | H | — | cyclopropyl | 0 | |
| 17.3 | 3-F | H | H | — | cyclopropyl | 0 | |
| 17.4 | 3-Cl | H | H | — | cyclopropyl | 0 | |
| 17.5 | 3-Br | H | H | — | cyclopropyl | 0 | |
| 17.6 | 3-CF₃ | H | H | — | cyclopropyl | 0 | |
| 17.7 | 3-CH₃ | H | H | — | cyclopropyl | 0 | |
| 17.8 | 3-C₂H₅ | H | H | — | cyclopropyl | 0 | |
| 17.9 | 3-OCH₃ | H | H | — | cyclopropyl | 0 | |
| 17.10 | 3-OC₂H₅ | H | H | — | cyclopropyl | 0 | |
| 17.11 | 4-F | H | H | — | cyclopropyl | 0 | |
| 17.12 | 3-F | H | H | 3-CH₃ | cyclopropyl | 1 | |
| 17.13 | 3-Cl | H | H | 3-CH₃ | cyclopropyl | 1 | |
| 17.14 | 3-Br | H | H | 3-CH₃ | cyclopropyl | 1 | |
| 17.15 | 3-CF₃ | H | H | 3-CH₃ | cyclopropyl | 1 | |
| 17.16 | 3-CH₃ | H | H | 3-CH₃ | cyclopropyl | 1 | |
| 17.17 | 3-C₂H₅ | H | H | 3-CH₃ | cyclopropyl | 1 | |
| 17.18 | 3-OCH₃ | H | H | 3-CH₃ | cyclopropyl | 1 | |
| 17.19 | 3-OC₂H₅ | H | H | 3-CH₃ | cyclopropyl | 1 | |
| 17.20 | 4-F | H | H | 3-CH₃ | cyclopropyl | 1 | |
| 17.21 | 3-F | H | H | 3-CH₃ | CH₃ | 1 | |
| 17.22 | 3-Cl | H | H | 3-CH₃ | CH₃ | 1 | |
| 17.23 | 3-Br | H | H | 3-CH₃ | CH₃ | 1 | |
| 17.24 | 3-CF₃ | H | H | 3-CH₃ | CH₃ | 1 | |
| 17.25 | 3-CH₃ | H | H | 3-CH₃ | CH₃ | 1 | |
| 17.26 | 3-C₂H₅ | H | H | 3-CH₃ | CH₃ | 1 | |
| 17.27 | 3-OCH₃ | H | H | 3-CH₃ | CH₃ | 1 | |
| 17.28 | 3-OC₂H₅ | H | H | 3-CH₃ | CH₃ | 1 | |
| 17.29 | 4-F | H | H | 3-CH₃ | CH₃ | 1 | |
| 17.30 | 3-F | H | CH₃ | 5-CH₃ | CH₃ | 1 | |
| 17.31 | 3-Cl | H | CH₃ | 5-CH₃ | CH₃ | 1 | |
| 17.32 | 3-Br | H | CH₃ | 5-CH₃ | CH₃ | 1 | |
| 17.33 | 3-CF₃ | H | CH₃ | 5-CH₃ | CH₃ | 1 | |
| 17.34 | 3-CH₃ | H | CH₃ | 5-CH₃ | CH₃ | 1 | |
| 17.35 | 3-C₂H₅ | H | CH₃ | 5-CH₃ | CH₃ | 1 | |
| 17.36 | 3-OCH₃ | H | CH₃ | 5-CH₃ | CH₃ | 1 | |
| 17.37 | 3-OC₂H₅ | H | CH₃ | 5-CH₃ | CH₃ | 1 | |
| 17.38 | 4-F | H | CH₃ | 5-CH₃ | CH₃ | 1 | |
| 17.39 | 3-F | 3-F | H | 5-CH₃ | CH₃ | 1 | |
| 17.40 | 3-Cl | 3-F | H | 5-CH₃ | CH₃ | 1 | |
| 17.41 | 3-Br | 3-F | H | 5-CH₃ | CH₃ | 1 | |
| 17.42 | 3-CF₃ | 3-F | H | 5-CH₃ | CH₃ | 1 | |
| 17.43 | 3-CH₃ | 3-F | H | 5-CH₃ | CH₃ | 1 | |
| 17.44 | 3-C₂H₅ | 3-F | H | 5-CH₃ | CH₃ | 1 | |
| 17.45 | 3-OCH₃ | 3-F | H | 5-CH₃ | CH₃ | 1 | |
| 17.46 | 3-OC₂H₅ | 3-F | H | 5-CH₃ | CH₃ | 1 | |
| 17.47 | 4-F | 3-F | H | 5-CH₃ | CH₃ | 1 | |

TABLE 18

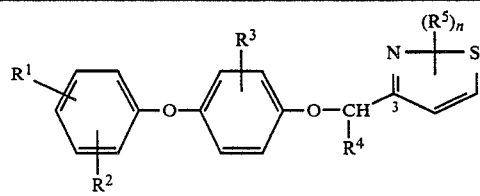

| Comp. No. | R¹ | R² | R⁴ | R⁵ | n | Phys. data (mp. °C.) |
|---|---|---|---|---|---|---|
| 18.1 | H | H | H | — | 0 | |
| 18.2 | H | H | H | 5-CH₃ | 1 | |
| 18.3 | 3-F | H | H | 5-CH₃ | 1 | |
| 18.4 | 3-Cl | H | H | 5-CH₃ | 1 | |
| 18.5 | 3-Br | H | H | 5-CH₃ | 1 | |
| 18.6 | 3-CF₃ | H | H | 5-CH₃ | 1 | |
| 18.7 | 3-OCH₃ | H | H | 5-CH₃ | 1 | |
| 18.8 | 3-CH₃ | H | H | 5-CH₃ | 1 | |
| 18.9 | 3-C₂H₅ | H | H | 5-CH₃ | 1 | |
| 18.10 | H | H | H | 5-cyclopropyl | 1 | |
| 18.11 | 3-F | H | H | 5-cyclopropyl | 1 | |
| 18.12 | 3-Cl | H | H | 5-cyclopropyl | 1 | |
| 18.13 | 3-Br | H | H | 5-cyclopropyl | 1 | |
| 18.14 | 3-CF₃ | H | H | 5-cyclopropyl | 1 | |
| 18.15 | 3-OCH₃ | H | H | 5-cyclopropyl | 1 | |
| 18.16 | 3-CH₃ | H | H | 5-cyclopropyl | 1 | |
| 18.17 | 3-C₂H₅ | H | H | 5-cyclopropyl | 1 | |
| 18.18 | 3-Cl | 4-F | H | 5-cyclopropyl | 1 | |
| 18.19 | H | H | H | 5-OC₂H₅ | 1 | |
| 18.20 | H | H | CH₃ | 5-CH₃ | 1 | |
| 18.21 | H | H | CH₃ | 5-cyclopropyl | 1 | |

TABLE 19

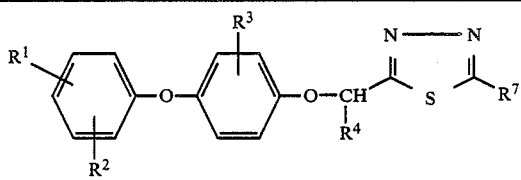

| Comp. No. | R¹ | R³ | R⁴ | R⁷ | Phys. data (mp. °C.) |
|---|---|---|---|---|---|
| 19.1 | H | H | H | cyclopropyl | |
| 19.2 | H | H | CH₃ | cyclopropyl | |
| 19.3 | 3-F | H | H | cyclopropyl | |
| 19.4 | 3-Cl | H | H | cyclopropyl | |
| 19.5 | 3-Br | H | H | cyclopropyl | |
| 19.6 | 3-CF₃ | H | H | cyclopropyl | |
| 19.7 | 3-CH₃ | H | H | cyclopropyl | |
| 19.8 | 3-C₂H₅ | H | H | cyclopropyl | |
| 19.9 | 3-OCH₃ | H | H | cyclopropyl | |
| 19.10 | 3-OC₂H₅ | H | H | cyclopropyl | |
| 19.11 | 4-F | H | CH₃ | cyclopropyl | |
| 19.12 | 3-F | H | CH₃ | cyclopropyl | |
| 19.13 | 3-Cl | H | CH₃ | cyclopropyl | |
| 19.14 | 3-Br | H | CH₃ | cyclopropyl | |
| 19.15 | 3-CF₃ | H | CH₃ | cyclopropyl | |
| 19.16 | 3-CH₃ | H | CH₃ | cyclopropyl | |
| 19.17 | 3-C₂H₅ | H | CH₃ | cyclopropyl | |
| 19.18 | 3-OCH₃ | H | CH₃ | cyclopropyl | |
| 19.19 | 3-OC₂H₅ | H | CH₃ | cyclopropyl | |
| 19.20 | 4-F | H | H | cyclopropyl | |
| 19.21 | 3-F | 3-F | H | cyclopropyl | |
| 19.22 | 3-Cl | 3-F | H | cyclopropyl | |
| 19.23 | 3-Br | 3-F | H | cyclopropyl | |
| 19.24 | 3-CF₃ | 3-F | H | cyclopropyl | |
| 19.25 | 3-CH₃ | 3-F | H | cyclopropyl | |
| 19.26 | 3-C₂H₅ | 3-F | H | cyclopropyl | |
| 19.27 | 3-OCH₃ | 3-F | H | cyclopropyl | |
| 19.28 | 3-OC₂H₅ | 3-F | H | cyclopropyl | |
| 19.29 | 4-F | 3-F | H | cyclopropyl | |
| 19.30 | 3-F | 3-F | CH₃ | cyclopropyl | |
| 19.31 | 3-Cl | 3-F | CH₃ | cyclopropyl | |
| 19.32 | 3-Br | 3-F | CH₃ | cyclopropyl | |
| 19.33 | 3-CF₃ | 3-F | CH₃ | cyclopropyl | |
| 19.34 | 3-CH₃ | 3-F | CH₃ | cyclopropyl | |
| 19.35 | 3-C₂H₅ | 3-F | CH₃ | cyclopropyl | |
| 19.36 | 3-OCH₃ | 3-F | CH₃ | cyclopropyl | |
| 19.37 | 3-OC₂H₅ | 3-F | CH₃ | cyclopropyl | |
| 19.38 | 4-F | 3-F | CH₃ | cyclopropyl | |
| 19.39 | H | 3-F | CH₃ | cyclopropyl | |
| 19.40 | H | 3-F | H | cyclopropyl | |

TABLE 19-continued

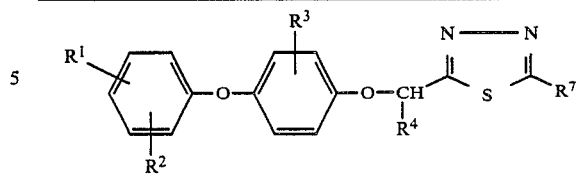

TABLE 20

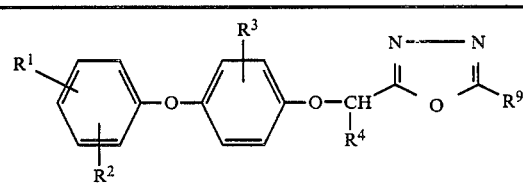

| Comp. No. | R¹ | R² | R³ | R⁴ | R⁹ | Phys. data (mp. °C.) |
|---|---|---|---|---|---|---|
| 20.1 | H | H | H | H | H | |
| 20.2 | H | H | H | CH₃ | H | |
| 20.3 | 3-F | H | H | H | H | |
| 20.4 | 3-Cl | H | H | H | H | |
| 20.5 | 3-Br | H | H | H | H | |
| 20.6 | 3-CF₃ | H | H | H | H | |
| 20.7 | 3-CH₃ | H | H | H | H | |
| 20.8 | 3-C₂H₅ | H | H | H | H | |
| 20.9 | 3-OCH₃ | H | H | H | H | |
| 20.10 | 3-Cl | 4-F | H | H | H | |
| 20.11 | 3-F | H | 3-F | H | H | |
| 20.12 | 3-Cl | H | 3-F | H | H | |
| 20.13 | 3-CF₃ | H | 3-F | H | H | |
| 20.14 | 3-CH₃ | H | 3-F | H | H | |
| 20.15 | 3-OCH₃ | H | 3-F | H | H | |
| 20.16 | 3-Cl | 4-F | 3-F | H | H | |

TABLE 20-continued $$R^1 - \text{Ph}(R^2) - O - \text{Ph}(R^3) - O - \underset{R^4}{CH} - C(=N-N=)O - C - R^9$$

| Comp. No. | R¹ | R² | R³ | R⁴ | R⁹ | Phys. data (mp. °C.) |
|---|---|---|---|---|---|---|
| 20.17 | 3-F | H | 3-Cl | H | H | |
| 20.18 | 3-Cl | H | 3-Cl | H | H | |
| 20.19 | 3-Br | H | 3-Cl | H | H | |
| 20.20 | 3-CF₃ | H | 3-Cl | H | H | |
| 20.21 | 3-CH₃ | H | 3-Cl | H | H | |
| 20.22 | 3-OCH₃ | H | 3-Cl | H | H | |
| 20.23 | 3-Cl | 4-F | 3-Cl | H | H | |
| 20.24 | H | H | H | H | CH₃ | 78–79 |
| 20.25 | H | H | H | CH₃ | CH₃ | |
| 20.26 | 3-F | H | H | H | CH₃ | |
| 20.27 | 3-Cl | H | H | H | CH₃ | |
| 20.28 | 3-Br | H | H | H | CH₃ | |
| 20.29 | 3-CF₃ | H | H | H | CH₃ | |
| 20.30 | 3-CH₃ | H | H | H | CH₃ | 88–89 |
| 20.31 | 3-C₂H₅ | H | H | H | CH₃ | |
| 20.32 | 3-OCH₃ | H | H | H | CH₃ | |
| 20.33 | 3-Cl | 4-F | H | H | CH₃ | 81 |
| 20.34 | 3-F | H | 3-F | H | CH₃ | |
| 20.35 | 3-Cl | H | 3-F | H | CH₃ | |
| 20.36 | 3-CF₃ | H | 3-F | H | CH₃ | 300 MHz-¹H—NMR in CDCl₃ [ppm]:2.60(s) |
| 20.37 | 3-CH₃ | H | 3-F | H | CH₃ | |
| 20.38 | 3-OCH₃ | H | 3-F | H | CH₃ | |
| 20.39 | 3-Cl | 4-F | 3-F | H | CH₃ | |
| 20.40 | 3-F | H | 3-Cl | H | CH₃ | |
| 20.41 | 3-Cl | H | 3-Cl | H | CH₃ | |
| 20.42 | 3-Br | H | 3-Cl | H | CH₃ | |
| 20.43 | 3-CF₃ | H | 3-Cl | H | CH₃ | |
| 20.44 | 3-CH₃ | H | 3-Cl | H | CH₃ | |
| 20.45 | 3-C₂H₅ | H | 3-Cl | H | CH₃ | |
| 20.46 | 3-OCH₃ | H | 3-Cl | H | CH₃ | |
| 20.47 | 3-Cl | H | 3-Cl | H | CH₃ | |
| 20.48 | H | H | H | H | cyclopropyl | 65–68 |
| 20.49 | H | H | H | CH₃ | cyclopropyl | |
| 20.50 | 3-F | H | H | H | cyclopropyl | 300-MHz-¹NMR in CDCl₃ [ppm]:5.17(s) |
| 20.51 | 3-Cl | H | H | H | cyclopropyl | 300-MHz-¹NMR in CDCl₃ [ppm]:5.16(s) |
| 20.52 | 3-Br | H | H | H | cyclopropyl | 61–64 |
| 20.53 | 3-CF₃ | H | H | H | cyclopropyl | 300 MHz-¹H—NMR in CDCl₃ [ppm]:5.20(s) |
| 20.54 | 3-CH₃ | H | H | H | cyclopropyl | 300 MHz-¹H—NMR in CDCl₃ [ppm]:2.36(s) |
| 20.55 | 3-C₂H₅ | H | H | H | cyclopropyl | 57–58 |
| 20.56 | 3-OCH₃ | H | H | H | cyclopropyl | 300-MHz-¹NMR in CDCl₃ [ppm]:3.73(s) |
| 20.57 | 3-Cl | 4-F | H | H | cyclopropyl | 300 MHz-¹H—NMR in CDCl₃ [ppm]:5.20(s) |
| 20.58 | 3-F | H | 3-F | H | cyclopropyl | |
| 20.59 | 3-Cl | H | 3-F | H | cyclopropyl | |
| 20.60 | 3-Br | H | 3-F | H | cyclopropyl | |
| 20.61 | 3-CF₃ | H | 3-F | H | cyclopropyl | 300 MHz-¹H—NMR in CDCl₃ [ppm]:5.49(s) |
| 20.62 | 3-CH₃ | H | 3-F | H | cyclopropyl | |
| 20.63 | 3-C₂H₅ | H | 3-F | H | cyclopropyl | |
| 20.64 | 3-OCH₃ | H | 3-F | H | cyclopropyl | |
| 20.65 | 3-Cl | 4-F | 3-F | H | cyclopropyl | |
| 20.66 | 3-F | H | 3-Cl | H | cyclopropyl | |
| 20.67 | 3-Cl | H | 3-Cl | H | cyclopropyl | |
| 20.68 | 3-Br | H | 3-Cl | H | cyclopropyl | |
| 20.69 | 3-CF₃ | H | 3-Cl | H | cyclopropyl | |
| 20.70 | 3-CH₃ | H | 3-Cl | H | cyclopropyl | |
| 20.71 | 3-C₂H₅ | H | 3-Cl | H | cyclopropyl | |
| 20.72 | 3-OCH₃ | H | 3-Cl | H | cyclopropyl | |
| 20.73 | 3-Cl | 4-F | 3-Cl | H | cyclopropyl | |
| 20.74 | H | H | H | H | Cl | |
| 20.75 | H | H | H | H | Br | |
| 20.76 | 3-F | H | H | H | Cl | |
| 20.77 | 3-Cl | H | H | H | Cl | |
| 20.78 | 3-Br | H | H | H | Cl | |
| 20.79 | 3-CF₃ | H | H | H | Cl | |

TABLE 20-continued

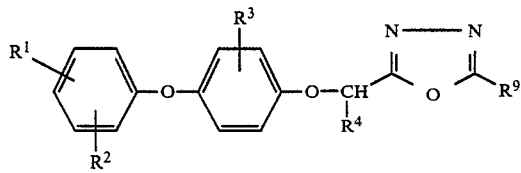

| Comp. No. | R¹ | R² | R³ | R⁴ | R⁹ | Phys. data (mp. °C.) |
|---|---|---|---|---|---|---|
| 20.80 | 3-CH₃ | H | H | H | Cl | |
| 20.81 | 3-C₂H₅ | H | H | H | Cl | |
| 20.82 | 3-OCH₃ | H | H | H | Cl | |
| 20.83 | 3-Cl | 4-F | H | H | Cl | |
| 20.84 | H | H | H | H | OCH₃ | |
| 20.85 | H | H | H | H | OC₂H₅ | |
| 20.86 | 3-F | H | H | H | OC₂H₅ | |
| 20.87 | 3-Cl | H | H | H | OC₂H₅ | |
| 20.88 | 3-Br | H | H | H | OC₂H₅ | |
| 20.89 | 3-CF₃ | H | H | H | OC₂H₅ | |
| 20.90 | 3-CH₃ | H | H | H | OC₂H₅ | |
| 20.91 | 3-CH₃ | H | H | H | OC₂H₅ | |
| 20.92 | 3-C₂H₅ | H | H | H | OC₂H₅ | |
| 20.93 | 3-OCH₃ | H | H | H | OC₂H₅ | |
| 20.94 | 3-Cl | 4-F | H | H | OC₂H₅ | |
| 20.95 | 3-F | H | 3-Cl | H | OC₂H₅ | |
| 20.96 | 3-F | H | 3-F | H | OC₂H₅ | |
| 20.97 | 3-Cl | H | 3-F | H | OC₂H₅ | |
| 20.98 | 3-CF₃ | H | 3-F | H | OC₂H₅ | |
| 20.99 | 3-OCH₃ | H | 3-Cl | H | OC₂H₅ | |
| 20.100 | H | H | H | H | C₂H₅ | 300 MHz ¹H—NMR in CDCl₃ [ppm]:1.39(t) |
| 20.101 | 4-F | H | H | H | cyclopropyl | 55–56 |

TABLE 21

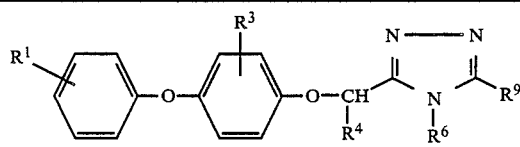

| Comp. No. | R¹ | R³ | R⁴ | R⁹ | R⁶ | Phys. data (mp. °C.) |
|---|---|---|---|---|---|---|
| 21.1 | H | H | H | H | CH₃ | |
| 21.2 | H | H | CH₃ | H | CH₃ | |
| 21.3 | 3-F | H | H | H | CH₃ | |
| 21.4 | 3-Cl | H | H | H | CH₃ | |
| 21.5 | 3-Br | H | H | H | CH₃ | |
| 21.6 | 3-CF₃ | H | H | H | CH₃ | |
| 21.7 | 3-CH₃ | H | H | H | CH₃ | |
| 21.8 | 3-C₂H₅ | H | H | H | CH₃ | |
| 21.9 | 3-OCH₃ | H | H | H | CH₃ | |
| 21.10 | 3-OC₂H₅ | H | H | H | CH₃ | |
| 21.11 | 4-F | H | H | H | CH₃ | |
| 21.12 | 3-F | H | CH₃ | H | CH₃ | |
| 21.13 | 3-Cl | H | CH₃ | H | CH₃ | |
| 21.14 | 3-Br | H | CH₃ | H | CH₃ | |
| 21.15 | 3-CF₃ | H | CH₃ | H | CH₃ | |
| 21.16 | 3-CH₃ | H | CH₃ | H | CH₃ | |
| 21.17 | 3-C₂H₅ | H | CH₃ | H | CH₃ | |
| 21.18 | 3-OCH₃ | H | CH₃ | H | CH₃ | |
| 21.19 | 3-OC₂H₅ | H | CH₃ | H | CH₃ | |
| 21.20 | 4-F | H | CH₃ | H | CH₃ | |
| 21.21 | 3-F | 3-F | H | cyclopropyl | CH₃ | |
| 21.22 | 3-Cl | 3-F | H | cyclopropyl | CH₃ | |
| 21.23 | 3-Br | 3-F | H | cyclopropyl | CH₃ | |
| 21.24 | 3-CF₃ | 3-F | H | cyclopropyl | CH₃ | |
| 21.25 | 3-CH₃ | 3-F | H | cyclopropyl | CH₃ | |
| 21.26 | 3-C₂H₅ | 3-F | H | cyclopropyl | CH₃ | |
| 21.27 | 3-OCH₃ | 3-F | H | cyclopropyl | CH₃ | |
| 21.28 | 3-OC₂H₅ | 3-F | H | cyclopropyl | CH₃ | |
| 21.29 | 4-F | 3-F | H | cyclopropyl | CH₃ | |
| 21.30 | 3-F | H | CH₃ | cyclopropyl | CH₃ | |
| 21.31 | 3-Cl | H | CH₃ | cyclopropyl | CH₃ | |
| 21.32 | 3-Br | H | CH₃ | cyclopropyl | CH₃ | |
| 21.33 | 3-CF₃ | H | CH₃ | cyclopropyl | CH₃ | |

TABLE 21-continued

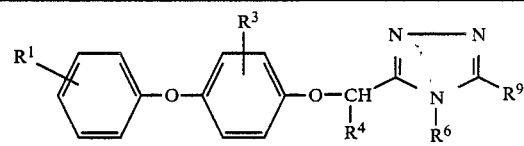

| Comp. No. | R¹ | R³ | R⁴ | R⁹ | R⁶ | Phys. data (mp. °C.) |
|---|---|---|---|---|---|---|
| 21.34 | 3-CH₃ | H | CH₃ | cyclopropyl | CH₃ | |
| 21.35 | 3-C₂H₅ | H | CH₃ | cyclopropyl | CH₃ | |
| 21.36 | 3-OCH₃ | H | CH₃ | cyclopropyl | CH₃ | |
| 21.37 | 3-OC₂H₅ | H | CH₃ | cyclopropyl | CH₃ | |
| 21.38 | 4-F | H | CH₃ | cyclopropyl | CH₃ | |
| 21.39 | 3-F | H | H | CH₃ | CH₃ | |
| 21.40 | 3-Cl | H | H | CH₃ | CH₃ | |
| 21.41 | 3-Br | H | H | CH₃ | CH₃ | |
| 21.42 | 3-CF₃ | H | H | CH₃ | CH₃ | |
| 21.43 | 3-CH₃ | H | H | CH₃ | CH₃ | |
| 21.44 | 3-C₂H₅ | H | H | CH₃ | CH₃ | |
| 21.45 | 3-OCH₃ | H | H | CH₃ | CH₃ | |
| 21.46 | 3-OC₃H₅ | H | H | CH₃ | CH₃ | |
| 21.47 | 4-F | H | H | CH₃ | CH₃ | |

TABLE 22

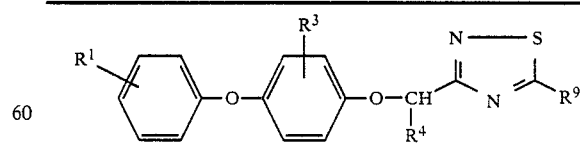

| Comp. No. | R¹ | R³ | R⁴ | R⁹ | Phys. data (mp. °C.) |
|---|---|---|---|---|---|
| 22.1 | H | H | H | H | |
| 22.2 | H | H | CH₃ | H | |
| 22.3 | 3-F | H | H | H | |
| 22.4 | 3-Cl | H | H | H | |
| 22.5 | 3-Br | H | H | H | |

TABLE 22-continued

Structure: $R^1$-phenyl-O-phenyl($R^3$)-O-CH($R^4$)-C(=N-S-C($R^9$)=N ring)

| Comp. No. | $R^1$ | $R^3$ | $R^4$ | $R^9$ | Phys. data (mp. °C.) |
|---|---|---|---|---|---|
| 22.6 | 3-CF$_3$ | H | H | H | |
| 22.7 | 3-CH$_3$ | H | H | H | |
| 22.8 | 3-C$_2$H$_5$ | H | H | H | |
| 22.9 | 3-OCH$_3$ | H | H | H | |
| 22.10 | 3-OC$_2$H$_5$ | H | H | H | |
| 22.11 | 4-F | H | H | H | |
| 22.12 | 3-F | H | H | cyclopropyl | |
| 22.13 | 3-Cl | H | H | cyclopropyl | |
| 22.14 | 3-Br | H | H | cyclopropyl | |
| 22.15 | 3-CF$_3$ | H | H | cyclopropyl | |
| 22.16 | 3-CH$_3$ | H | H | cyclopropyl | |
| 22.17 | 3-C$_2$H$_5$ | H | H | cyclopropyl | |
| 22.18 | 3-OCH$_3$ | H | H | cyclopropyl | |
| 22.19 | 3-OC$_2$H$_5$ | H | H | cyclopropyl | |
| 22.20 | 4-F | H | H | CH$_3$ | |
| 22.21 | 3-F | H | H | CH$_3$ | |
| 22.22 | 3-Cl | H | H | CH$_3$ | |
| 22.23 | 3-Br | H | H | CH$_3$ | |
| 22.24 | 3-CF$_3$ | H | H | CH$_3$ | |
| 22.25 | 3-CH$_3$ | H | H | CH$_3$ | |
| 22.26 | 3-C$_2$H$_5$ | H | H | CH$_3$ | |
| 22.27 | 3-OCH$_3$ | H | H | CH$_3$ | |
| 22.28 | 3-OC$_2$H$_5$ | H | H | CH$_3$ | |
| 22.29 | 4-F | H | H | CH$_3$ | |
| 22.30 | 3-F | 3-F | H | CH$_3$ | |
| 22.31 | 3-Cl | 3-F | H | CH$_3$ | |
| 22.32 | 3-Br | 3-F | H | CH$_3$ | |
| 22.33 | 3-CF$_3$ | 3-F | H | CH$_3$ | |
| 22.34 | 3-CH$_3$ | 3-F | H | CH$_3$ | |
| 22.35 | 3-C$_2$H$_5$ | 3-F | H | CH$_3$ | |
| 22.36 | 3-OCH$_3$ | 3-F | H | CH$_3$ | |
| 22.37 | 3-OC$_2$H$_5$ | 3-F | H | CH$_3$ | |
| 22.38 | 4-F | 3-F | H | CH$_3$ | |
| 22.39 | 3-F | H | CH$_3$ | cyclopropyl | |
| 22.40 | 3-Cl | H | CH$_3$ | cyclopropyl | |
| 22.41 | 3-Br | H | CH$_3$ | cyclopropyl | |
| 22.42 | 3-CF$_3$ | H | CH$_3$ | cyclopropyl | |
| 22.43 | 3-CH$_3$ | H | CH$_3$ | cyclopropyl | |
| 22.44 | 3-C$_2$H$_5$ | H | CH$_3$ | cyclopropyl | |
| 22.45 | 3-OCH$_3$ | H | CH$_3$ | cyclopropyl | |
| 22.46 | 3-OC$_2$H$_5$ | H | CH$_3$ | cyclopropyl | |
| 22.47 | 4-F | H | CH$_3$ | cyclopropyl | |

TABLE 23

Structure: $R^1$-phenyl-O-phenyl-O-CH$_2$-C(=N-O-C($R^9$)=N ring) with $R^2$ on first phenyl

| Comp. No. | $R^1$ | $R^2$ | $R^9$ | Phys. data (mp. °C.) |
|---|---|---|---|---|
| 23.1 | H | H | H | |
| 23.2 | H | H | CH$_3$ | |
| 23.3 | 3-F | H | CH$_3$ | |
| 23.4 | 3-Cl | H | CH$_3$ | |
| 23.5 | 3-Br | H | CH$_3$ | |
| 23.6 | 3-OCH$_3$ | H | CH$_3$ | |
| 23.7 | 3-CF$_3$ | H | CH$_3$ | |
| 23.8 | 3-CH$_3$ | H | CH$_3$ | |
| 23.9 | 3-C$_2$H$_5$ | H | CH$_3$ | |
| 23.10 | 3-Cl | 4-F | CH$_3$ | |
| 23.11 | H | H | cyclopropyl | |
| 23.12 | 3-F | H | cyclopropyl | |
| 23.13 | 3-Cl | H | cyclopropyl | |
| 23.14 | 3-Br | H | cyclopropyl | |
| 23.15 | 3-OCH$_3$ | H | cyclopropyl | |
| 23.16 | 3-CF$_3$ | H | cyclopropyl | |
| 23.17 | 3-CH$_3$ | H | cyclopropyl | |
| 23.18 | 3-C$_2$H$_5$ | H | cyclopropyl | |
| 23.19 | H | H | OC$_2$H$_5$ | |
| 23.20 | 3-F | H | OC$_2$H$_5$ | |
| 23.21 | 3-Br | H | OC$_2$H$_5$ | |
| 23.22 | 3-C$_2$H$_5$ | H | OC$_2$H$_5$ | |

TABLE 24

Structure: $R^1$-phenyl-O-phenyl($R^3$)-O-CH($R^4$)-C(=N-N($R^6$)-C($R^9$)=N ring)

| Comp. No. | $R^1$ | $R^3$ | $R^4$ | $R^9$ | $R^6$ | Phys. data (mp. °C.) |
|---|---|---|---|---|---|---|
| 24.1 | H | H | H | H | CH$_3$ | |
| 24.2 | H | H | CH$_3$ | H | CH$_3$ | |
| 24.3 | 3-F | H | H | H | CH$_3$ | |
| 24.4 | 3-Cl | H | H | H | CH$_3$ | |
| 24.5 | 3-Br | H | H | H | CH$_3$ | |
| 24.6 | 3-CF$_3$ | H | H | H | CH$_3$ | |
| 24.7 | 3-CH$_3$ | H | H | H | CH$_3$ | |
| 24.8 | 3-C$_2$H$_5$ | H | H | H | CH$_3$ | |
| 24.9 | 3-OCH$_3$ | H | H | H | CH$_3$ | |
| 24.10 | 3-OC$_2$H$_5$ | H | H | H | CH$_3$ | |
| 24.11 | 4-F | H | H | H | CH$_3$ | |
| 24.12 | 3-F | H | H | cyclopropyl | CH$_3$ | |
| 24.13 | 3-Cl | H | H | cyclopropyl | CH$_3$ | |
| 24.14 | 3-Br | H | H | cyclopropyl | CH$_3$ | |
| 24.15 | 3-CF$_3$ | H | H | cyclopropyl | CH$_3$ | |
| 24.16 | 3-CH$_3$ | H | H | cyclopropyl | CH$_3$ | |
| 24.17 | 3-C$_2$H$_5$ | H | H | cyclopropyl | CH$_3$ | |
| 24.18 | 3-OCH$_3$ | H | H | cyclopropyl | CH$_3$ | |
| 24.19 | 3-OC$_2$H$_5$ | H | H | cyclopropyl | CH$_3$ | |
| 24.20 | 4-F | H | H | cyclopropyl | CH$_3$ | |
| 24.21 | 3-F | H | CH$_3$ | cyclopropyl | CH$_3$ | |
| 24.22 | 3-Cl | H | CH$_3$ | cyclopropyl | CH$_3$ | |
| 24.23 | 3-Br | H | CH$_3$ | cyclopropyl | CH$_3$ | |
| 24.24 | 3-CF$_3$ | H | CH$_3$ | cyclopropyl | CH$_3$ | |
| 24.25 | 3-CH$_3$ | H | CH$_3$ | cyclopropyl | CH$_3$ | |
| 24.26 | 3-C$_2$H$_5$ | H | CH$_3$ | cyclopropyl | CH$_3$ | |
| 24.27 | 3-OCH$_3$ | H | CH$_3$ | cyclopropyl | CH$_3$ | |
| 24.28 | 3-OC$_2$H$_5$ | H | CH$_3$ | cyclopropyl | CH$_3$ | |
| 24.29 | 4-F | H | CH$_3$ | cyclopropyl | CH$_3$ | |
| 24.30 | 3-F | 3-F | H | cyclopropyl | CH$_3$ | |
| 24.31 | 3-Cl | 3-F | H | cyclopropyl | CH$_3$ | |
| 24.32 | 3-Br | 3-F | H | cyclopropyl | CH$_3$ | |
| 24.33 | 3-CF$_3$ | 3-F | H | cyclopropyl | CH$_3$ | |
| 24.34 | 3-CH$_3$ | 3-F | H | cyclopropyl | CH$_3$ | |
| 24.35 | 3-C$_2$H$_5$ | 3-F | H | cyclopropyl | CH$_3$ | |
| 24.36 | 3-OCH$_3$ | 3-F | H | cyclopropyl | CH$_3$ | |
| 24.37 | 3-OC$_2$H$_5$ | 3-F | H | cyclopropyl | CH$_3$ | |
| 24.38 | 4-F | 3-F | H | cyclopropyl | CH$_3$ | |
| 24.39 | 3-F | H | H | CH$_3$ | CH$_3$ | |
| 24.40 | 3-Cl | H | H | CH$_3$ | CH$_3$ | |
| 24.41 | 3-Br | H | H | CH$_3$ | CH$_3$ | |
| 24.42 | 3-CF$_3$ | H | H | CH$_3$ | CH$_3$ | |
| 24.43 | 3-CH$_3$ | H | H | CH$_3$ | CH$_3$ | |
| 24.44 | 3-C$_2$H$_5$ | H | H | CH$_3$ | CH$_3$ | |
| 24.45 | 3-OCH$_3$ | H | H | CH$_3$ | CH$_3$ | |
| 24.46 | 3-OC$_2$H$_5$ | H | H | CH$_3$ | CH$_3$ | |
| 24.47 | 4-F | H | H | CH$_3$ | CH$_3$ | |

TABLE 25

Structure: R¹-phenyl-O-phenyl(R³)-O-CH(R⁴)-C(=N-S-N=)R⁹ (thiadiazole)

| Comp. No. | R¹ | R³ | R⁴ | R⁹ | Phys. data (mp. °C.) |
|---|---|---|---|---|---|
| 25.1 | H | H | H | H | |
| 25.2 | H | H | CH₃ | H | |
| 25.3 | 3-F | H | H | H | |
| 25.4 | 3-Cl | H | H | H | |
| 25.5 | 3-Br | H | H | H | |
| 25.6 | 3-CF₃ | H | H | H | |
| 25.7 | 3-CH₃ | H | H | H | |
| 25.8 | 3-C₂H₅ | H | H | H | |
| 25.9 | 3-OCH₃ | H | H | H | |
| 25.10 | 3-OC₂H₅ | H | H | H | |
| 25.11 | 4-F | H | H | H | |
| 25.12 | 3-F | H | H | CH₃ | |
| 25.13 | 3-Cl | H | H | CH₃ | |
| 25.14 | 3-Br | H | H | CH₃ | |
| 25.15 | 3-CF₃ | H | H | CH₃ | |
| 25.16 | 3-CH₃ | H | H | CH₃ | |
| 25.17 | 3-C₂H₅ | H | H | CH₃ | |
| 25.18 | 3-OCH₃ | H | H | CH₃ | |
| 25.19 | 3-OC₂H₅ | H | H | CH₃ | |
| 25.20 | 4-F | H | H | CH₃ | |
| 25.21 | 3-F | H | H | cyclopropyl | |
| 25.22 | 3-Cl | H | H | cyclopropyl | |
| 25.23 | 3-Br | H | H | cyclopropyl | |
| 25.24 | 3-CF₃ | H | H | cyclopropyl | |
| 25.25 | 3-CH₃ | H | H | cyclopropyl | |
| 25.26 | 3-C₂H₅ | H | H | cyclopropyl | |
| 25.27 | 3-OCH₃ | H | H | cyclopropyl | |
| 25.28 | 3-OC₂H₅ | H | H | cyclopropyl | |
| 25.29 | 4-F | H | H | cyclopropyl | |
| 25.30 | 3-F | 3-F | H | CH₃ | |
| 25.31 | 3-Cl | 3-F | H | CH₃ | |
| 25.32 | 3-Br | 3-F | H | CH₃ | |
| 25.33 | 3-CF₃ | 3-F | H | CH₃ | |
| 25.34 | 3-CH₃ | 3-F | H | CH₃ | |
| 25.35 | 3-C₂H₅ | 3-F | H | CH₃ | |
| 25.36 | 3-OCH₃ | 3-F | H | CH₃ | |
| 25.37 | 3-OC₂H₅ | 3-F | H | CH₃ | |
| 25.38 | 4-F | 3-F | H | CH₃ | |
| 25.39 | 3-F | H | CH₃ | CH₃ | |
| 25.40 | 3-Cl | H | CH₃ | CH₃ | |
| 25.41 | 3-Br | H | CH₃ | CH₃ | |
| 25.42 | 3-CF₃ | H | CH₃ | CH₃ | |
| 25.43 | 3-CH₃ | H | CH₃ | CH₃ | |
| 25.44 | 3-C₂H₅ | H | CH₃ | CH₃ | |
| 25.45 | 3-OCH₃ | H | CH₃ | CH₃ | |
| 25.46 | 3-OC₂H₅ | H | CH₃ | CH₃ | |
| 25.47 | 4-F | H | CH₃ | CH₃ | |

TABLE 26

Structure: R¹-phenyl-O-phenyl(R³)-O-CH(R⁴)-C(=N-O-N=)R⁹ (oxadiazole)

| Comp. No. | R¹ | R² | R³ | R⁴ | R⁹ | Phys. data (mp. °C.) |
|---|---|---|---|---|---|---|
| 26.1 | H | H | H | H | H | |
| 26.2 | 3-F | H | H | H | H | |
| 26.3 | 3-Cl | H | H | H | H | |
| 26.4 | 3-Br | H | H | H | H | |
| 26.5 | 3-CF₃ | H | H | H | H | |
| 26.6 | 3-OCH₃ | H | H | H | H | |
| 26.7 | 3-C₂H₅ | H | H | H | H | |
| 26.8 | 3-CH₃ | H | H | H | H | |
| 26.9 | H | H | H | H | CH₃ | |
| 26.10 | 3-F | H | H | H | CH₃ | |
| 26.11 | 3-Cl | H | H | H | CH₃ | |
| 26.12 | 3-Br | H | H | H | CH₃ | |
| 26.13 | 3-CF₃ | H | H | H | CH₃ | |
| 26.14 | 3-OCH₃ | H | H | H | CH₃ | |
| 26.15 | 3-C₂H₅ | H | H | H | CH₃ | |
| 26.16 | 3-CH₃ | H | H | H | CH₃ | |
| 26.17 | 3-Cl | 4-F | H | H | CH₃ | |
| 26.18 | H | H | H | H | OC₂H₅ | 70–72 |
| 26.19 | H | H | H | H | OCH₃ | 93–94 |
| 26.20 | H | H | H | H | cyclopropyl | 99 |
| 26.21 | 3-F | H | H | H | cyclopropyl | 101 |
| 26.22 | 3-Cl | H | H | H | cyclopropyl | 82 |
| 26.23 | 3-Br | H | H | H | cyclopropyl | 83 |
| 26.24 | 3-CF₃ | H | H | H | cyclopropyl | 102 |
| 26.25 | 3-OCH₃ | H | H | H | cyclopropyl | 66 |
| 26.26 | 3-CH₃ | H | H | H | cyclopropyl | 76 |
| 26.27 | 3-C₂H₅ | H | H | H | cyclopropyl | |
| 26.28 | 3-Cl | 4-F | H | H | cyclopropyl | |
| 26.32 | H | H | 3-F | H | cyclopropyl | |
| 26.33 | H | H | 3-F | H | CH₃ | |
| 26.34 | H | H | 3-F | H | OC₂H₅ | |
| 26.35 | H | H | H | H | iso-C₃H₇ | |
| 26.36 | 3-F | H | 3-F | H | cyclopropyl | |
| 26.37 | 3-CF | H | 3-Cl | H | cyclopropyl | |
| 26.38 | 3-Cl | H | 3-F | H | cyclopropyl | |
| 26.39 | 3-Cl | H | 3-Cl | H | cyclopropyl | |
| 26.40 | 3-Br | H | 3-F | H | cyclopropyl | |
| 26.41 | 3-Br | H | 3-Cl | H | cyclopropyl | |
| 26.42 | 3-CF₃ | H | 3-F | H | cyclopropyl | 300 MHz-¹H—NMR in CDCl₃ [ppm]: 5.49(s) |
| 26.43 | 3-CF₃ | H | 3-Cl | H | cyclopropyl | |
| 26.44 | 3-CH₃ | H | 3-F | H | cyclopropyl | |
| 26.45 | 3-CH₃ | H | 3-Cl | H | cyclopropyl | |
| 26.46 | 3-C₂H₅ | H | 3-F | H | cyclopropyl | |
| 26.47 | 3-C₂H₅ | H | 3-Cl | H | cyclopropyl | |
| 26.48 | 3-OCH₃ | H | 3-F | H | cyclopropyl | |
| 26.49 | 3-OCH₃ | H | 3-Cl | H | cyclopropyl | |
| 26.50 | 3-Cl | 4-F | 3-F | H | cyclopropyl | |
| 26.51 | 3-Cl | 4-F | 3-Cl | H | cyclopropyl | |
| 26.52 | H | 4-F | H | H | cyclopropyl | |
| 26.53 | H | 4-F | 3-F | H | cyclopropyl | |
| 26.54 | H | 4-F | 3-Cl | H | cyclopropyl | |

TABLE 27

Structure: R¹-phenyl-O-phenyl(R³)-O-CH(R⁴)-C(=N-N(R⁶)-)=N-R⁹ (triazole)

| Comp. No. | R¹ | R³ | R⁴ | R⁹ | R⁶ | Phys. data (mp. °C.) |
|---|---|---|---|---|---|---|
| 27.1 | H | H | H | | CH₃ | |
| 27.2 | H | H | CH₃ | | CH₃ | |
| 27.3 | 3-F | H | H | | CH₃ | |
| 27.4 | 3-Cl | H | H | | CH₃ | |
| 27.5 | 3-Br | H | H | | CH₃ | |
| 27.6 | 3-CF₃ | H | H | | CH₃ | |
| 27.7 | 3-CH₃ | H | H | | CH₃ | |
| 27.8 | 3-C₂H₅ | H | H | | CH₃ | |
| 27.9 | 3-OCH₃ | H | H | | CH₃ | |
| 27.10 | 3-OC₂H₅ | H | H | | CH₃ | |
| 27.11 | 4-F | H | H | | CH₃ | |

TABLE 27-continued

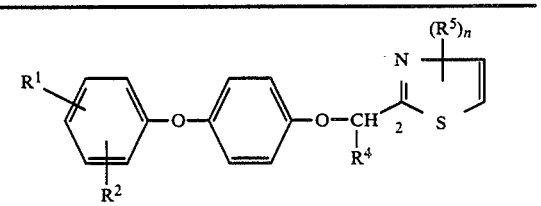

| Comp. No. | R¹ | R³ | R⁴ | R⁹ | R⁶ | Phys. data (mp. °C.) |
|---|---|---|---|---|---|---|
| 27.12 | 3-F | H | H | CH₃ | CH₃ | 82–84 |
| 27.13 | 3-Cl | H | H | CH₃ | CH₃ | |
| 27.14 | 3-Br | H | H | CH₃ | CH₃ | |
| 27.15 | 3-CF₃ | H | H | CH₃ | CH₃ | |
| 27.16 | 3-CH₃ | H | H | CH₃ | CH₃ | |
| 27.17 | 3-C₂H₅ | H | H | CH₃ | CH₃ | 79–80 |
| 27.18 | 3-OCH₃ | H | H | CH₃ | CH₃ | |
| 27.19 | 3-H | H | H | CH₃ | CH₃ | 109–110 |
| 27.20 | 4-F | H | H | CH₃ | CH₃ | |
| 27.21 | 3-F | H | H | cyclopropyl | CH₃ | 64–66 |
| 27.22 | 3-Cl | H | H | cyclopropyl | CH₃ | 82–85 |
| 27.23 | 3-Br | H | H | cyclopropyl | CH₃ | 85–88 |
| 27.24 | 3-CF₃ | H | H | cyclopropyl | CH₃ | 77–79 |
| 27.25 | 3-CH₃ | H | H | cyclopropyl | CH₃ | |
| 27.26 | 3-C₂H₅ | H | H | cyclopropyl | CH₃ | 59–61 |
| 27.27 | 3-OCH₃ | H | H | cyclopropyl | CH₃ | |
| 27.28 | 3-H | H | H | cyclopropyl | CH₃ | 80–82 |
| 27.29 | 4-F | H | H | cyclopropyl | CH₃ | |
| 27.30 | 3-F | H | CH₃ | cyclopropyl | CH₃ | |
| 27.31 | 3-Cl | H | CH₃ | cyclopropyl | CH₃ | |
| 27.32 | 3-Br | H | CH₃ | cyclopropyl | CH₃ | |
| 27.33 | 3-CF₃ | H | CH₃ | cyclopropyl | CH₃ | |
| 27.34 | 3-CH₃ | H | CH₃ | cyclopropyl | CH₃ | |
| 27.35 | 3-C₂H₅ | H | CH₃ | cyclopropyl | CH₃ | |
| 27.36 | 3-OCH₃ | H | CH₃ | cyclopropyl | CH₃ | |
| 27.37 | 3-OC₂H₅ | H | CH₃ | cyclopropyl | CH₃ | |
| 27.38 | 4-F | H | CH₃ | cyclopropyl | CH₃ | |
| 27.39 | 3-F | 3-F | H | cyclopropyl | CH₃ | |
| 27.40 | 3-Cl | 3-F | H | cyclopropyl | CH₃ | |
| 27.41 | 3-Br | 3-F | H | cyclopropyl | CH₃ | |
| 27.42 | 3-CF₃ | 3-F | H | cyclopropyl | CH₃ | |
| 27.43 | 3-CH₃ | 3-F | H | cyclopropyl | CH₃ | |
| 27.44 | 3-C₂H₅ | 3-F | H | cyclopropyl | CH₃ | |
| 27.45 | 3-OCH₃ | 3-F | H | cyclopropyl | CH₃ | |
| 27.46 | 3-OC₂H₅ | 3-F | H | cyclopropyl | CH₃ | |
| 27.47 | 4-F | 3-F | H | cyclopropyl | CH₃ | |

TABLE 28

| Comp. No. | R¹ | R² | R⁴ | R⁵ | n | Phys. data (mp. °C.) |
|---|---|---|---|---|---|---|
| 28.1 | H | H | H | — | 0 | |
| 28.2 | H | H | CH₃ | — | 0 | |
| 28.3 | 3-F | H | H | — | 0 | |
| 28.4 | 3-Cl | H | CH₃ | — | 0 | |
| 28.5 | 3-Br | H | H | — | 0 | |
| 28.6 | 3-CF₃ | H | CH₃ | — | 0 | |
| 28.7 | 3-CH₃ | H | H | — | 0 | |
| 28.8 | 3-C₂H₅ | H | CH₃ | — | 0 | |
| 28.9 | 3-OCH₃ | H | H | — | 0 | |
| 28.10 | 3-Cl | 4-F | CH₃ | — | 0 | |
| 28.11 | H | H | H | 5-CH₃ | 1 | |
| 28.12 | H | H | CH₃ | 5-CH₃ | 1 | |
| 28.13 | 3-F | H | H | 5-CH₃ | 1 | |
| 28.14 | 3-F | H | CH₃ | 5-CH₃ | 1 | |
| 28.15 | 3-Cl | H | H | 5-CH₃ | 1 | |
| 28.16 | 3-Cl | H | CH₃ | 5-CH₃ | 1 | |
| 28.17 | 3-Br | H | H | 5-CH₃ | 1 | |
| 28.18 | 3-Br | H | CH₃ | 5-CH₃ | 1 | |
| 28.19 | 3-CF₃ | H | H | 5-CH₃ | 1 | |
| 28.20 | 3-CF₃ | H | CH₃ | 5-CH₃ | 1 | |

TABLE 28-continued

| Comp. No. | R¹ | R² | R⁴ | R⁵ | n | Phys. data (mp. °C.) |
|---|---|---|---|---|---|---|
| 28.21 | 3-CH₃ | H | H | 5-CH₃ | 1 | |
| 28.22 | 3-CH₃ | H | CH₃ | 5-CH₃ | 1 | |
| 28.23 | 3-C₂H₅ | H | H | 5-CH₃ | 1 | |
| 28.24 | 3-C₂H₅ | H | CH₃ | 5-CH₃ | 1 | |
| 28.25 | 3-OCH₃ | H | H | 5-CH₃ | 1 | |
| 28.26 | 3-OCH₃ | H | CH₃ | 5-CH₃ | 1 | |
| 28.27 | 3-Cl | 4-F | H | 5-CH₃ | 1 | |
| 28.28 | 3-Cl | 4-F | CH₃ | 5-CH₃ | 1 | |
| 28.29 | H | H | H | 5-cyclopropyl | 1 | |
| 28.30 | H | H | CH₃ | 5-cyclopropyl | 1 | |
| 28.31 | 3-F | H | H | 5-cyclopropyl | 1 | |
| 28.32 | 3-Cl | H | CH₃ | 5-cyclopropyl | 1 | |
| 28.33 | 3-Br | H | H | 5-cyclopropyl | 1 | |
| 28.34 | 3-CF₃ | H | CH₃ | 5-cyclopropyl | 1 | |
| 28.35 | 3-CH₃ | H | H | 5-cyclopropyl | 1 | |
| 28.36 | 3-C₂H₅ | H | CH₃ | 5-cyclopropyl | 1 | |
| 28.37 | 3-OCH₃ | H | H | 5-cyclopropyl | 1 | |
| 28.38 | 3-Cl | 4-F | CH₃ | 5-cyclopropyl | 1 | |
| 28.39 | H | H | H | 5-OCH₃ | 1 | |
| 28.40 | H | H | CH₃ | 5-OCH₃ | 1 | |
| 28.41 | H | H | H | 5-OC₂H₅ | 1 | |
| 28.42 | H | H | CH₃ | 5-OC₂H₅ | 1 | |
| 28.43 | 3-F | H | H | 5-OC₂H₅ | 1 | |
| 28.44 | 3-Cl | H | CH₃ | 5-OC₂H₅ | 1 | |
| 28.45 | 3-Br | H | H | 5-OC₂H₅ | 1 | |
| 28.46 | 3-CF₃ | H | CH₃ | 5-OC₂H₅ | 1 | |
| 28.47 | 3-CH₃ | H | H | 5-OC₂H₅ | 1 | |
| 28.48 | 3-C₂H₅ | H | CH₃ | 5-OC₂H₅ | 1 | |
| 28.49 | 3-OCH₃ | H | H | 5-OC₂H₅ | 1 | |
| 28.50 | 3-Cl | H | H | 5-OC₂H₅ | 1 | |
| 28.51 | H | H | H | 5-Cl | 1 | |
| 28.52 | H | H | CH₃ | 5-Cl | 1 | |
| 28.53 | 3-F | H | H | 5-Cl | 1 | |
| 28.54 | 3-Cl | H | CH₃ | 5-Cl | 1 | |
| 28.55 | 3-Br | H | H | 5-Cl | 1 | |
| 28.56 | 3-CF₃ | H | CH₃ | 5-Cl | 1 | |
| 28.57 | 3-CH₃ | H | H | 5-Cl | 1 | |
| 28.58 | 3-C₂H₅ | H | CH₃ | 5-Cl | 1 | |
| 28.59 | 3-OCH₃ | H | H | 5-Cl | 1 | |
| 28.60 | 3-Cl | 4-F | CH₃ | 5-Cl | 1 | |
| 28.61 | H | H | H | 4-CH₃ | 1 | |
| 28.62 | H | H | CH₃ | 4-CH₃ | 1 | |
| 28.63 | 3-F | H | H | 4-CH₃ | 1 | |
| 28.64 | 3-Cl | H | CH₃ | 4-CH₃ | 1 | |
| 28.65 | 3-Br | H | H | 4-CH₃ | 1 | |
| 28.66 | 3-CF₃ | H | CH₃ | 4-CH₃ | 1 | |
| 28.67 | 3-CH₃ | H | H | 4-CH₃ | 1 | |
| 28.68 | 3-C₂H₅ | H | CH₃ | 4-CH₃ | 1 | |
| 28.69 | 3-OCH₃ | H | H | 4-CH₃ | 1 | |
| 28.70 | 3-Cl | 4-F | CH₃ | 4-CH₃ | 1 | |
| 28.71 | H | H | H | 4-cyclopropyl | 1 | |
| 28.72 | H | H | CH₃ | 4-cyclopropyl | 1 | |
| 28.73 | 3-F | H | H | 4-cyclopropyl | 1 | |
| 28.74 | 3-Cl | H | CH₃ | 4-cyclopropyl | 1 | |
| 28.75 | 3-Br | H | H | 4-cyclopropyl | 1 | |
| 28.76 | 3-CF₃ | H | CH₃ | 4-cyclopropyl | 1 | |
| 28.77 | 3-CH₃ | H | H | 4-cyclopropyl | 1 | |
| 28.78 | 3-C₂H₅ | H | CH₃ | 4-cyclopropyl | 1 | |
| 28.79 | 3-OCH₃ | H | H | 4-cyclopropyl | 1 | |
| 28.80 | 3-Cl | 4-F | CH₃ | 4-cyclopropyl | 1 | |
| 28.81 | H | H | H | 4-OCH₃ | 1 | |
| 28.82 | H | H | H | 4-OC₂H₅ | 1 | |
| 28.83 | H | H | CH₃ | 4-OC₂H₅ | 1 | |
| 28.84 | 3-F | H | H | 4-OC₂H₅ | 1 | |
| 28.85 | 3-Cl | H | CH₃ | 4-OC₂H₅ | 1 | |
| 28.86 | 3-Br | H | H | 4-OC₂H₅ | 1 | |
| 28.87 | 3-CF₃ | H | CH₃ | 4-OC₂H₅ | 1 | |
| 28.88 | 3-CH₃ | H | H | 4-OC₂H₅ | 1 | |
| 28.89 | 3-C₂H₅ | H | CH₃ | 4-OC₂H₅ | 1 | |
| 28.90 | 3-OCH₃ | H | H | 4-OC₂H₅ | 1 | |

TABLE 28-continued

Structure: R¹, R² substituted phenyl-O-phenyl-O-CH(R⁴)-C(=N)-[thiazole with (R⁵)ₙ]

| Comp. No. | R¹ | R² | R⁴ | R⁵ | n | Phys. data (mp. °C.) |
|---|---|---|---|---|---|---|
| 28.91 | 3-Cl | 4-F | CH₃ | 4-OC₂H₅ | 1 | |
| 28.92 | H | H | H | 4-Cl | 1 | |
| 28.93 | H | H | CH₃ | 4-Cl | 1 | |
| 28.94 | 3-F | H | H | 4-Cl | 1 | |
| 28.95 | 3-Cl | H | CH₃ | 4-Cl | 1 | |
| 28.96 | 3-Br | H | H | 4-Cl | 1 | |
| 28.97 | 3-CF₃ | H | CH₃ | 4-Cl | 1 | |
| 28.98 | 3-CH₃ | H | H | 4-Cl | 1 | |
| 28.99 | 3-C₂H₅ | H | CH₃ | 4-Cl | 1 | |
| 28.100 | 3-OCH₃ | H | H | 4-Cl | 1 | |
| 28.101 | 3-Cl | 4-F | CH₃ | 4-Cl | 1 | |

TABLE 29

Structure: R¹, R² substituted phenyl-O-phenyl-O-CH(R⁴)-C(=N)-[oxazole with (R⁵)ₙ]

| Comp. No. | R¹ | R² | R⁴ | R⁵ | n | Phys. data (mp. °C.) |
|---|---|---|---|---|---|---|
| 29.1 | H | H | H | — | 0 | |
| 29.2 | H | H | CH₃ | — | 0 | |
| 29.3 | 3-F | H | H | — | 0 | |
| 29.4 | 3-Cl | H | H | — | 0 | |
| 29.5 | 3-Br | H | H | — | 0 | |
| 29.6 | 3-CF₃ | H | H | — | 0 | |
| 29.7 | 3-CH₃ | H | H | — | 0 | |
| 29.8 | 3-C₂H₅ | H | H | — | 0 | |
| 29.9 | 3-OCH₃ | H | H | — | 0 | |
| 29.10 | 3-Cl | 4-F | H | — | 0 | |
| 29.11 | H | H | H | 5-CH₃ | 1 | |
| 29.12 | 3-F | H | H | 5-CH₃ | 1 | |
| 29.13 | 3-Cl | H | H | 5-CH₃ | 1 | |
| 29.14 | 3-Br | H | H | 5-CH₃ | 1 | |
| 29.15 | 3-CF₃ | H | H | 5-CH₃ | 1 | |
| 29.16 | 3-CH₃ | H | H | 5-CH₃ | 1 | |
| 29.17 | 3-C₂H₅ | H | H | 5-CH₃ | 1 | |
| 29.18 | 3-OCH₃ | H | H | — | 0 | |
| 29.19 | 3-Cl | 4-F | H | — | 0 | |
| 29.20 | H | H | H | 5-cyclopropyl | 1 | |
| 29.21 | 3-F | H | H | 5-cyclopropyl | 1 | |
| 29.22 | 3-Cl | H | H | 5-cyclopropyl | 1 | |
| 29.23 | 3-CN | H | H | 5-cyclopropyl | 1 | |
| 29.24 | 3-Br | H | H | 5-cyclopropyl | 1 | |
| 29.25 | 3-CF₃ | H | H | 5-cyclopropyl | 1 | |
| 29.26 | 3-CH₃ | H | H | 5-cyclopropyl | 1 | |
| 29.27 | 3-C₂H₅ | H | H | 5-cyclopropyl | 1 | |
| 29.28 | 3-OCH₃ | H | H | 5-cyclopropyl | 1 | |
| 29.29 | 3-Cl | 4-F | H | 5-cyclopropyl | 1 | |
| 29.30 | H | H | H | 4-CH₃ | 1 | |
| 29.31 | 3-F | H | H | 4-CH₃ | 1 | |
| 29.32 | 3-Cl | H | H | 4-CH₃ | 1 | |
| 29.33 | 3-Br | H | H | 4-CH₃ | 1 | |
| 29.34 | 3-CF₃ | H | H | 4-CH₃ | 1 | |
| 29.35 | 3-CH₃ | H | H | 4-CH₃ | 1 | |
| 29.36 | 3-C₂H₅ | H | H | 4-CH₃ | 1 | |
| 29.37 | 3-OCH₃ | H | H | 4-CH₃ | 1 | |
| 29.38 | 3-Cl | 4-F | H | 4-CH₃ | 1 | |
| 29.39 | H | H | H | 4-cyclopropyl | 1 | |
| 29.40 | 3-F | H | H | 4-cyclopropyl | 1 | |
| 29.41 | 3-Cl | H | H | 4-cyclopropyl | 1 | |
| 29.42 | 3-Br | H | H | 4-cyclopropyl | 1 | |
| 29.43 | 3-CF₃ | H | H | 4-cyclopropyl | 1 | |
| 29.44 | 3-CH₃ | H | H | 4-cyclopropyl | 1 | |
| 29.45 | 3-C₂H₅ | H | H | 4-cyclopropyl | 1 | |
| 29.46 | 3-OCH₃ | H | H | 4-cyclopropyl | 1 | |
| 29.47 | 3-Cl | 4-F | H | 4-cyclopropyl | 1 | |
| 29.48 | H | H | H | 4-OCH₃ | 1 | |
| 29.49 | H | H | H | 4-OC₂H₅ | 1 | |
| 29.50 | 3-F | H | H | 4-OC₂H₅ | 1 | |
| 29.51 | 3-Cl | H | H | 4-OC₂H₅ | 1 | |
| 29.52 | 3-Br | H | H | 4-OC₂H₅ | 1 | |
| 29.53 | 3-CF₃ | H | H | 4-OC₂H₅ | 1 | |
| 29.54 | 3-CH₃ | H | H | 4-OC₂H₅ | 1 | |
| 29.55 | 3-C₂H₅ | H | H | 4-OC₂H₅ | 1 | |
| 29.56 | 3-OCH₃ | H | H | 4-OC₂H₅ | 1 | |
| 29.57 | 3-Cl | 4-F | H | 4-OC₂H₅ | 1 | |
| 29.58 | H | H | H | 5-OCH₃ | 1 | |
| 29.59 | H | H | H | 5-OC₂H₅ | 1 | |
| 29.60 | 3-F | H | H | 5-OC₂H₅ | 1 | |
| 29.61 | 3-Cl | H | H | 5-OC₂H₅ | 1 | |
| 29.62 | 3-Br | H | H | 5-OC₂H₅ | 1 | |
| 29.63 | 3-CF₃ | H | H | 5-OC₂H₅ | 1 | |
| 29.64 | 3-CH₃ | H | H | 5-OC₂H₅ | 1 | |
| 29.65 | 3-C₂H₅ | H | H | 5-OC₂H₅ | 1 | |
| 29.66 | 3-OCH₃ | H | H | 5-OC₂H₅ | 1 | |
| 29.67 | 3-Cl | 4-F | H | 5-OC₂H₅ | 1 | |
| 29.68 | H | H | H | 5-Cl | 1 | |
| 29.69 | 3-F | H | H | 5-Cl | 1 | |
| 29.70 | 3-Cl | H | H | 5-Cl | 1 | |
| 29.71 | 3-CF₃ | H | H | 5-Cl | 1 | |
| 29.72 | 3-CH₃ | H | H | 5-Cl | 1 | |
| 29.73 | 3-OCH₃ | H | H | 5-Cl | 1 | |
| 29.74 | 3-Cl | H | H | 5-Cl | 1 | |

TABLE 30

Structure: R¹ substituted phenyl-O-(R³ substituted phenyl)-O-CH(R⁴)-C(=N)-[imidazole with (R⁵)ₙ and R⁶]

| Comp. No. | R¹ | R³ | R⁴ | R⁵ | R⁶ | n | Phys. data (mp. °C.) |
|---|---|---|---|---|---|---|---|
| 30.1 | H | H | H | — | CH₃ | 0 | 84–86 |
| 30.2 | H | H | CH₃ | — | CH₃ | 0 | |
| 30.3 | 3-F | H | H | — | CH₃ | 0 | 97–99 |
| 30.4 | 3-Cl | H | H | — | CH₃ | 0 | |
| 30.5 | 3-Br | H | H | — | CH₃ | 0 | |
| 30.6 | 3-CF₃ | H | H | — | CH₃ | 0 | |
| 30.7 | 3-CH₃ | H | H | — | CH₃ | 0 | |
| 30.8 | 3-C₂H₅ | H | H | — | CH₃ | 0 | 300 MHz-¹H-NMR in CDCl₃ [ppm]: 3.78(s) |
| 30.9 | 3-OCH₃ | H | H | — | CH₃ | 0 | |
| 30.10 | 3-OC₂H₅ | H | H | — | CH₃ | 0 | |
| 30.11 | 4-F | H | H | 5-CH₃ | CH₃ | 1 | |
| 30.12 | 3-F | H | H | 5-CH₃ | CH₃ | 1 | |
| 30.13 | 3-Cl | H | H | 5-CH₃ | CH₃ | 1 | |
| 30.14 | 3-Br | H | H | 5-CH₃ | CH₃ | 1 | |
| 30.15 | 3-CF₃ | H | H | 5-CH₃ | CH₃ | 1 | |
| 30.16 | 3-CH₃ | H | H | 5-CH₃ | CH₃ | 1 | |
| 30.17 | 3-C₂H₅ | H | H | 5-CH₃ | CH₃ | 1 | |
| 30.18 | 3-OCH₃ | H | H | 5-CH₃ | CH₃ | 1 | |
| 30.19 | 3-OC₂H₅ | H | H | 5-CH₃ | CH₃ | 1 | |
| 30.20 | 4-F | H | H | 5-CH₃ | CH₃ | 1 | |

TABLE 30-continued

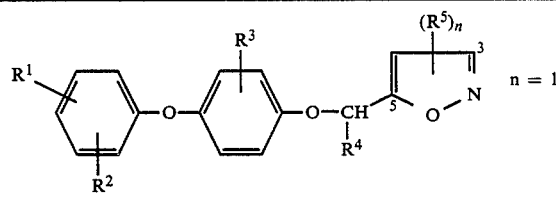

| Comp. No. | R¹ | R³ | R⁴ | R⁵ | R⁶ | n | Phys. data (mp. °C.) |
|---|---|---|---|---|---|---|---|
| 30.21 | 3-F | H | $CH_3$ | 5-$CH_3$ | $CH_3$ | 1 | |
| 30.22 | 3-Cl | H | $CH_3$ | 5-$CH_3$ | $CH_3$ | 1 | |
| 30.23 | 3-Br | H | $CH_3$ | 5-$CH_3$ | $CH_3$ | 1 | |
| 30.24 | 3-$CF_3$ | H | $CH_3$ | 5-$CH_3$ | $CH_3$ | 1 | |
| 30.25 | 3-$CH_3$ | H | $CH_3$ | 5-$CH_3$ | $CH_3$ | 1 | |
| 30.26 | 3-$C_2H_5$ | H | $CH_3$ | 5-$CH_3$ | $CH_3$ | 1 | |
| 30.27 | 3-$OCH_3$ | H | $CH_3$ | 5-$CH_3$ | $CH_3$ | 1 | |
| 30.28 | 3-$OC_2H_5$ | H | $CH_3$ | 5-$CH_3$ | $CH_3$ | 1 | |
| 30.29 | 4-F | H | $CH_3$ | 5-$CH_3$ | $CH_3$ | 1 | |
| 30.30 | 3-F | H | $CH_3$ | — | $CH_3$ | 0 | |
| 30.31 | 3-Cl | H | $CH_3$ | — | $CH_3$ | 0 | |
| 30.32 | 3-Br | H | $CH_3$ | — | $CH_3$ | 0 | |
| 30.33 | 3-$CF_3$ | H | $CH_3$ | — | $CH_3$ | 0 | |
| 30.34 | 3-$CH_3$ | H | $CH_3$ | — | $CH_3$ | 0 | |
| 30.35 | 3-$C_2H_5$ | H | $CH_3$ | — | $CH_3$ | 0 | |
| 30.36 | 3-$OCH_3$ | H | $CH_3$ | — | $CH_3$ | 0 | |
| 30.37 | 3-$OC_2H_5$ | H | $CH_3$ | — | $CH_3$ | 0 | |
| 30.38 | 4-F | H | $CH_3$ | — | $CH_3$ | 0 | |
| 30.39 | 3-F | 3-F | H | — | $CH_3$ | 0 | |
| 30.40 | 3-Cl | 3-F | H | — | $CH_3$ | 0 | |
| 30.41 | 3-Br | 3-F | H | — | $CH_3$ | 0 | |
| 30.42 | 3-$CF_3$ | 3-F | H | — | $CH_3$ | 0 | |
| 30.43 | 3-$CH_3$ | 3-F | H | — | $CH_3$ | 0 | |
| 30.44 | 3-$C_2H_5$ | 3-F | H | — | $CH_3$ | 0 | |
| 30.45 | 3-$OCH_3$ | 3-F | H | — | $CH_3$ | 0 | |
| 30.46 | 3-$OC_2H_5$ | 3-F | H | — | $CH_3$ | 0 | |
| 30.47 | 4-F | 3-F | H | — | $CH_3$ | 0 | |

TABLE 31 n = 1

| Comp. No. | R¹ | R² | R³ | R⁴ | R⁵ in 3-position | Phys. data (mp. °C.) |
|---|---|---|---|---|---|---|
| 31.1 | H | H | H | H | $OC_2H_5$ | 54–58 |
| 31.2 | 3-F | H | H | H | $OC_2H_5$ | 42–43 |
| 31.3 | 3-Cl | H | H | H | $OC_2H_5$ | 57–58 |
| 31.4 | 3-Br | H | H | H | $OC_2H_5$ | 68–71 |
| 31.5 | 3-$CF_3$ | H | H | H | $OC_2H_5$ | 51–53 |
| 31.6 | 3-$OCH_3$ | H | H | H | $OC_2H_5$ | |
| 31.7 | 3-$CH_3$ | H | H | H | $OC_2H_5$ | 43–44 |
| 31.8 | 3-$C_2H_5$ | H | H | H | $OC_2H_5$ | 300 MHz-$^1$H-NMR in $CDCl_3$ [ppm]: 5.98(s) |
| 31.9 | 3-Cl | 4-F | H | H | $OC_2H_5$ | 55–56 |
| 31.10 | H | H | H | $CH_3$ | $OC_2H_5$ | 300 MHz-$^1$H-NMR in $CDCl_3$ [ppm]: 5.78(s) |
| 31.11 | 3-F | H | H | $CH_3$ | $OC_2H_5$ | |
| 31.12 | 3-Cl | H | H | $CH_3$ | $OC_2H_5$ | |
| 31.13 | 3-Br | H | H | $CH_3$ | $OC_2H_5$ | |
| 31.14 | 3-$CF_3$ | H | H | $CH_3$ | $OC_2H_5$ | |
| 31.15 | 3-$OCH_3$ | H | H | $CH_3$ | $OC_2H_5$ | |
| 31.16 | 3-$CH_3$ | H | H | $CH_3$ | $OC_2H_5$ | |
| 31.17 | 3-$C_2H_5$ | H | H | $CH_3$ | $OC_2H_5$ | |
| 31.18 | H | H | 3-F | H | $OC_2H_5$ | |
| 31.19 | H | H | 3-Cl | H | $OC_2H_5$ | |
| 31.20 | H | H | H | H | $OCH_3$ | 62–63 |
| 31.21 | H | H | H | H | Cl | |
| 31.22 | H | H | 3-F | $CH_3$ | $OC_2H_5$ | |
| 31.23 | H | H | 3-Cl | $CH_3$ | $OC_2H_5$ | |
| 31.24 | H | H | H | $CH_3$ | $OCH_3$ | 300 MHz-$^1$H-NMR in $CDCl_3$ [ppm]: 5.82(s) |
| 31.25 | H | H | H | H | $CH_3$ | 48–51 |
| 31.26 | 4-F | H | H | H | $CH_3$ | |
| 31.27 | H | H | H | H | iso-$C_3H_7$ | 200 MHz-$^1$H-NMR in $CDCl_3$ [ppm]: 1.26(6H); 3.04(1H); 5.05(2H); 6.2(1H); 6.8–7.35(9H) |
| 31.28 | H | H | H | H | tert.-$C_4H_9$ | 200-MHz-$^1$H-NMR in $CDCl_3$ [ppm]: 1.35 (9H); 5.1(2H); 6.3(1H); 6.9–7.4(9H) |
| 31.29 | H | H | H | H | ethyl | 300-MHz-$^1$H-NMR in $CDCl_3$ [ppm]: 1.25(3H); 2.9(2H); 5.1(2H); 6.2(1H); 6.8–7.1(7H); |

TABLE 31-continued $$R^1\text{-}C_6H_{?}\text{-}O\text{-}C_6H_3(R^3)\text{-}O\text{-}CH(R^4)\text{-}\text{isoxazoline}(R^5)_n$$ n = 1

| Comp. No. | R[1] | R[2] | R[3] | R[4] | R[5] in 3-position | Phys. data (mp. °C.) |
|---|---|---|---|---|---|---|
| 31.30 | H | H | H | H | phenyl | 7.2–7.4(2H) 100 |
| 31.31 | H | H | H | H | cyclohexyl | 94–95 |
| 31.32 | H | H | H | H | iso-$C_3H_7$ | 300-MHz-$^1$H-NMR in $CDCl_3$ [ppm]: 1.28(6H); 3.03((1H); 5.05(2H); 6.2(1H); 6.8–7.1 (7H); 7.2–7.35(2H) |
| 31.33 | H | H | H | H | (2,2-di-methyl-vinyl | |
| 31.34 | 4-$CF_3$ | H | H | H | $CH_3$ | |
| 31.35 | 4-$CF_3$ | 2-Cl | H | H | $CH_3$ | 57–62 |
| 31.36 | 4-$OCF_3$ | H | H | H | $CH_3$ | |
| 31.37 | 4-$OCH_3$ | H | H | H | $CH_3$ | |
| 31.38 | 4-iso-$C_3H_7$ | H | H | H | $CH_3$ | |
| 31.39 | 4-F | 2-Cl | H | H | $CH_3$ | 60–62 |
| 31.40 | H | H | H | H | $CH_2$—O—$CH_3$ | 300-MHz-$^1$H-NMR in $CDCl_3$ [ppm]: 3.38 (s) |
| 31.41 | H | H | H | $CH_3$ | iso-$C_3H_7$ | 300-MHz-$^1$H-NMR in $CDCl_3$ [ppm]: 1.66 (3H) |
| 31.42 | H | H | 2-F | H | iso-$C_3H_7$ | |
| 31.43 | 4-F | 3-F | 3-F | H | iso-$C_3H_7$ | |
| 31.44 | H | H | H | H | p-chloro-phenyl | |
| 31.45 | 4-$NO_2$ | H | H | H | (2,2-di-methyl)vinyl | |
| 31.46 | 4-CN | H | H | $CH_3$ | iso-$C_3H_7$ | |
| 31.47 | H | H | H | H | $CF_3$ | 40–42 |
| 31.48 | 4-F | 3-Cl | H | H | $CH_3$ | 86–87 |
| 31.49 | 4-Cl | 3-Cl | H | H | $CH_3$ | |
| 31.50 | 4-F | 3-F | H | H | $CH_3$ | 87–89 |
| 31.51 | H | H | 3-F | H | $CH_3$ | 300-MHz-$^1$H-NMR in $CDCl_3$ [ppm]: 2.34 (3H) |
| 31.52 | H | H | 3-Cl | H | $CH_3$ | |
| 31.53 | H | 3-F | H | H | $CH_3$ | 71–72 |
| 31.54 | H | 3-Cl | H | H | $CH_3$ | |
| 31.55 | H | 3-Br | H | H | $CH_3$ | 76–77 |
| 31.56 | H | 3-$OCH_3$ | H | H | $CH_3$ | 59–61 |
| 31.57 | H | 3-$C_2H_5$ | H | H | $CH_3$ | 68–70 |
| 31.58 | H | 3-$CF_3$ | H | H | $CH_3$ | 76–77 |
| 31.59 | H | 3-F | 3-Cl | H | $CH_3$ | |
| 31.60 | H | 3-Cl | 3-Cl | H | $CH_3$ | 87–90 |
| 31.61 | H | 3-Br | 3-Cl | H | $CH_3$ | 90–92 |
| 31.62 | H | 3-$OCH_3$ | 3-Cl | H | $CH_3$ | |
| 31.63 | H | 3-$C_2H_5$ | 3-Cl | H | $CH_3$ | |
| 31.64 | H | 3-$CF_3$ | 3-Cl | H | $CH_3$ | |
| 31.65 | H | 3-Cl | 3-Cl | H | $CH_3$ | |
| 31.66 | H | 3-F | 3-F | H | $CH_3$ | |
| 31.67 | H | 3-Cl | 3-F | H | $CH_3$ | 300-MHz-$^1$H-NMR in $CDCl_3$ [ppm]: 2.32 (3H) |
| 31.68 | H | 3-Br | 3-F | H | $CH_3$ | |
| 31.69 | H | 3-$OCH_3$ | 3-F | H | $CH_3$ | |
| 31.70 | H | 3-$C_2H_5$ | 3-F | H | $CH_3$ | |
| 31.71 | H | 3-$CF_3$ | 3-F | H | $CH_3$ | |
| 31.72 | 4-F | 3-Cl | 3-F | H | $CH_3$ | |
| 31.73 | 4-F | 3-Cl | H | $CH_3$ | $CH_3$ | |
| 31.74 | H | H | H | H | $CH_3$ | |
| 31.75 | H | H | 3-F | $CH_3$ | $CH_3$ | |
| 31.76 | H | 3-F | H | $CH_3$ | $CH_3$ | |
| 31.77 | H | H | H | H | cyclopropyl | 85–88 |
| 31.78 | 4-F | H | H | H | cyclopropyl | |
| 31.79 | 4-F | 3-Cl | H | H | cyclopropyl | 71–72 |
| 31.80 | 4-Cl | 3-Cl | H | H | cyclopropyl | |
| 31.81 | H | 3-F | H | H | cyclopropyl | 73–74 |
| 31.82 | H | 3-Cl | H | H | cyclopropyl | 72–73 |
| 31.83 | H | 3-Br | H | H | cyclopropyl | 41–42 |
| 31.84 | H | 3-$OCH_3$ | H | H | cyclopropyl | 42–44 |

TABLE 31-continued

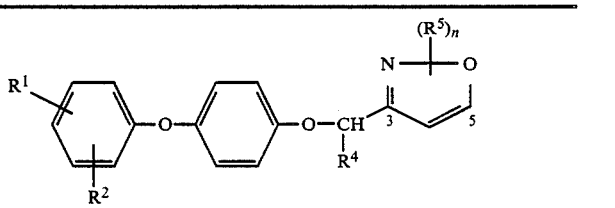
n = 1

| Comp. No. | R¹ | R² | R³ | R⁴ | R⁵ in 3-position | Phys. data (mp. °C.) |
|---|---|---|---|---|---|---|
| 31.85 | H | 3-C$_2$H$_5$ | H | H | cyclopropyl | 41–43 |
| 31.86 | H | 3-CF$_3$ | H | H | cyclopropyl | 96–97 |
| 31.87 | H | H | 3-F | H | cyclopropyl | 64–66 |
| 31.88 | 4-F | 3-F | H | H | cyclopropyl | |
| 31.89 | H | H | 3-Cl | H | cyclopropyl | |
| 31.90 | H | 3-F | 3-F | H | cyclopropyl | |
| 31.91 | F | 3-Cl | 3-F | H | cyclopropyl | |
| 31.92 | H | 3-CH$_3$ | 3-F | H | cyclopropyl | |
| 31.93 | H | 3-OCH$_3$ | 3-F | H | cyclopropyl | |
| 31.94 | H | 3-C$_2$H$_5$ | 3-F | H | cyclopropyl | |
| 31.95 | H | 3-CF$_3$ | 3-F | H | cyclopropyl | 300 MHz-$^1$H-NMR in CDCl$_3$ [ppm]: 5.38 (2H) |
| 31.96 | 4-F | 3-Cl | 3-F | H | cyclopropyl | |
| 31.97 | H | H | H | CH$_3$ | cyclopropyl | |
| 31.98 | 4-F | H | H | CH$_3$ | cyclopropyl | |
| 31.99 | H | 3-F | H | CH$_3$ | cyclopropyl | |
| 31.100 | H | 3-Cl | H | CH$_3$ | cyclopropyl | |
| 31.101 | H | 3-Br | H | CH$_3$ | cyclopropyl | |
| 31.102 | H | 3-OCH$_3$ | H | CH$_3$ | cyclopropyl | |
| 31.103 | H | 3-C$_2$H$_5$ | H | CH$_3$ | cyclopropyl | |
| 31.104 | H | 3-CF$_3$ | H | CH$_3$ | cyclopropyl | |
| 31.105 | 4-Cl | 3-Cl | H | CH$_3$ | cyclopropyl | |
| 31.106 | H | 3-CH$_3$ | H | H | cyclopropyl | 58–59 |
| 31.107 | H | 3-CH$_3$ | 3-F | H | cyclopropyl | |
| 31.108 | H | 3-CH$_3$ | H | H | CH$_3$ | 77–78 |
| 31.109 | H | 3-tert.—C$_4$—H$_9$ | H | H | CH$_3$ | 89–90 |
| 31.110 | 4-Cl | H | H | H | cyclopropyl | |
| 31.111 | 4-Br | H | H | H | cyclopropyl | |
| 31.112 | 4-CH$_3$ | H | H | H | cyclopropyl | |
| 31.113 | 4-OCH$_3$ | H | H | H | cyclopropyl | |
| 31.114 | 4-C$_2$H$_5$ | H | H | H | cyclopropyl | |
| 31.115 | 2-F | H | H | H | cyclopropyl | |
| 31.116 | 2-Cl | H | H | H | cyclopropyl | |
| 31.117 | 2-Br | H | H | H | cyclopropyl | |
| 31.118 | 2-CH$_2$ | H | H | H | cyclopropyl | |
| 31.119 | 3-Cl | 2-Cl | H | H | cyclopropyl | |
| 31.120 | 3-Cl | 5-Cl | H | H | cyclopropyl | 300-MHz-$^1$H-NMR in CDCl$_3$ [ppm]: 5.11 (s) |
| 31.121 | H | H | H | H | cyclobutyl | 300-MHz-$^1$H-NMR in CDCl$_3$ [ppm]: 5.11 (s) |
| 31.122 | 3-Br | H | H | H | cyclobutyl | 53–56 |

TABLE 32

| Comp. No. | R¹ | R² | R⁴ | R⁵ | n | Phys. data (mp. °C.) |
|---|---|---|---|---|---|---|
| 32.1 | H | H | H | 5-OC$_2$H$_5$ | 1 | |
| 32.2 | 3-F | H | H | 5-OC$_2$H$_5$ | 1 | |
| 32.3 | 3-Cl | H | H | 5-OC$_2$H$_5$ | 1 | |
| 32.4 | 3-Br | H | H | 5-OC$_2$H$_5$ | 1 | |
| 32.5 | 3-OCH$_3$ | H | H | 5-OC$_2$H$_5$ | 1 | |
| 32.6 | 3-CF$_3$ | H | H | 5-OC$_2$H$_5$ | 1 | |
| 32.7 | 3-CH$_3$ | H | H | 5-OC$_2$H$_5$ | 1 | |
| 32.8 | 3-C$_2$H$_5$ | H | H | 5-OC$_2$H$_5$ | 1 | |
| 32.9 | 3-Cl | 4-F | H | 5-OC$_2$H$_5$ | 1 | |
| 32.10 | H | H | CH$_3$ | 5-OC$_2$H$_5$ | 1 | |

TABLE 32-continued $R^1 \diagdown \diagup \diagdown \diagup O \diagdown \diagup \diagdown \diagup O-CH(R^4)-C_3=C_5-N(R^5)_n-O$ (ring)

| Comp. No. | $R^1$ | $R^2$ | $R^4$ | $R^5$ | n | Phys. data (mp. °C.) |
|---|---|---|---|---|---|---|
| 32.11 | 3-F | H | CH$_3$ | 5-OC$_2$H$_5$ | 1 | |
| 32.12 | 3-CH$_3$ | H | CH$_3$ | 5-OC$_2$H$_5$ | 1 | |
| 32.13 | 3-OCH$_3$ | H | CH$_3$ | 5-OC$_2$H$_5$ | 1 | |
| 32.14 | 3-CF$_3$ | H | CH$_3$ | 5-OC$_2$H$_5$ | 1 | |
| 32.15 | H | H | H | 5-Cl | 1 | |
| 32.16 | H | H | CH$_3$ | 5-Cl | 1 | |
| 32.17 | H | H | H | 5-cyclopropyl | 1 | 80–84 |
| 32.18 | 3-F | H | H | 5-cyclopropyl | 1 | 300 MHz-$^1$H—NMR in CDCl$_3$ [ppm]: 5.06 (s) |
| 32.19 | 3-Cl | H | H | 5-cyclopropyl | 1 | 48–52 |
| 32.20 | 3-Br | H | H | 5-cyclopropyl | 1 | |
| 32.21 | 3-CH$_3$ | H | H | 5-cyclopropyl | 1 | |
| 32.22 | 3-C$_2$H$_5$ | H | H | 5-cyclopropyl | 1 | |
| 32.23 | 3-OCH$_3$ | H | H | 5-cyclopropyl | 1 | |
| 32.24 | 3-CF$_3$ | H | H | 5-cyclopropyl | 1 | |
| 32.25 | 4-F | H | H | 5-cyclopropyl | 1 | |
| 32.26 | 4-Cl | H | H | 5-cyclopropyl | 1 | |
| 32.27 | 4-Br | H | H | 5-cyclopropyl | 1 | |
| 32.28 | 4-CH$_3$ | H | H | 5-cyclopropyl | 1 | |
| 32.29 | 4-C$_2$H$_5$ | H | H | 5-cyclopropyl | 1 | |
| 32.30 | 4-OCH$_3$ | H | H | 5-cyclopropyl | 1 | |
| 32.31 | 4-Cl | 3-Cl | H | 5-cyclopropyl | 1 | |
| 32.32 | 4-Cl | 2-Cl | H | 5-cyclopropyl | 1 | |

TABLE 33

$R^1 \diagdown \diagup \diagdown \diagup O \diagdown \diagup \diagdown \diagup O-CH_2-C_3=C_4-C_5-N(R^5)_n-O$ (ring)

| Comp. No. | $R^1$ | $R^5$ | n | Phys. data (mp. °C.) |
|---|---|---|---|---|
| 33.1 | H | 3-OC$_2$H$_5$ | 1 | |
| 33.2 | 3-F | 3-OC$_2$H$_5$ | 1 | |
| 33.3 | H | 5-OC$_2$H$_5$ | 2 | |
| 33.4 | 3-F | 5-OC$_2$H$_5$ | 1 | |
| 33.5 | H | 3-iso-C$_3$H$_7$, 5-CH$_3$ | 2 | 78–82 |
| 33.6 | H | 3-CH$_3$, 5-Br | | |

Use Examples

The concentrations at which the candidate compounds achieved a 100% kill rate or inhibition are the minimum concentrations. At least one replicate was used for each concentration.

EXAMPLE A

*Dysdercus intermedicus* (cotton stainer), breeding experiment

Petri dishes 10 cm in diameter were lined with 1 ml of acetonic solutions of the active ingredients. After the solvent had evaporated, 20 larvae of the penultimate stage were introduced into each dish. After 24 hours the surviving animals were transferred to 1 l jars containing 200 g of sterile quartz sand (particle size: 0 to 3 mm). Prior to commencement of the experiment, 25 ml of aqueous formulations of the active ingredients was poured onto the sand. The food proffered was swollen cotton seeds, which were changed weekly. The soil was also moistened weekly with pure water.

The temperature was kept at 25° to 27° C. The experiment was monitored until the control eggs hatched.

In this experiment the mortal dose of compound no. 31.25 was 10 ppm.

EXAMPLE B

Ovicidal action on *Dysdercus intermedicus* (cotton stainer)

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent the eggs coming into contact with the paper. The markers were then placed in plastic trays (adhesive strip at the top). Half a roll of absorbent cotton was moistened with water and placed in each beaker to prevent drying out, and the trays were covered with a glass plate. Assessment took place after the control bugs hatched (after about 8 days).

In this experiment, the lethal dose of compound no. 31.25 was 0.002%.

EXAMPLE C

Action on the laying of eggs by *Epilachna varivestis* (Mexican bean beetle)

Groups of 20 eggs of the Mexican bean beetle were dipped, together with the leaves they were on, for 3 seconds in aqueous formulations of the active ingredients. They were then placed on a moistened filter paper and introduced into plastic cages. The number of viable larvae which hatched (recognizable from the acceptance of the food proffered) was registered.

In this experiment, the lethal dose of compound no. 31.25 was 0.02 ppm.

EXPERIMENT D

Inhibition of the development of *Heliothis virescens* on treated nutrient medium 100 g of the standard nutrient medium for *Heliothis virescens* was filled into 250 ml beakers and carefully mixed, while warm, with aqueous formulations of the active ingredients. After the medium had cooled, 10 caterpillars of the third larval stage (1.5 to 1.8 cm) were introduced into each vessel, and the vessels were stored at 23° C. Pupation and hatching of the moths were assessed.

In this experiment, the mortal dose of compound no. 31.25 was 1 ppm.

We claim:

1. (p-Phenoxyphenoxy)-methyl-five-membered hetaryls of the formula I

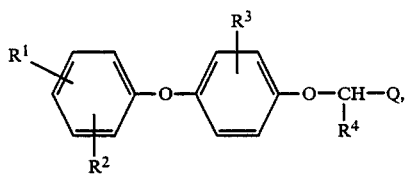

where the substituents have the following meanings:

$R^1$, $R^2$, $R^3$ hydrogen, halogen, $C_1$–$C_8$-alkyl, $C_1$–$C_8$-alkoxy, $C_1$–$C_4$-haloalkyl, $C_1$–$C_4$-haloalkoxy, $C_3$–$C_{10}$-cycloalkyl, nitro or cyano, $R^4$ hydrogen or $C_1$–$C_4$-alkyl, Q a five-membered hetaryl radical of the formulae II.31 to II.33

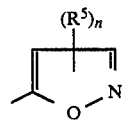

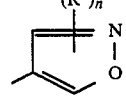

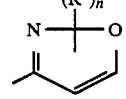

where $R^5$ is halogen, $C_1$–$C_8$-alkyl, $C_2$–$C_8$-alkenyl, $C_1$–$C_4$-haloalkyl, $C_1$–$C_8$-alkoxy, $C_2$–$C_8$-alkoxyalkyl, $C_3$–$C_{10}$-cycloalkyl, phenyl or $C_7$–$C_{20}$-phenylalkyl, the phenyl and $C_7$–$C_{20}$-phenylalkyl being unsubstituted or monosubstituted, disubstituted or trisubstituted in the aryl moiety by halogen, $C_1$–$C_8$-alkyl, $C_1$–$C_8$-alkoxy, $C_1$–$C_4$-haloalkyl or $C_1$–$C_4$-haloalkoxy or cyano or monosubstituted or disubstituted by nitro, and n is 0, 1, 2 or 3.

2. (p-Phenoxyphenoxy)-methylisoxazoles of the formula Ia

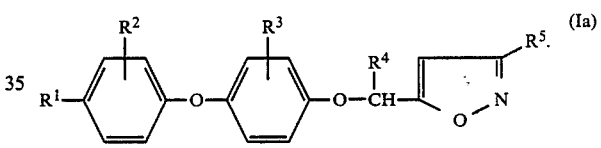

where the radicals $R^1$ to $R^5$ have the meanings given in claim 1.

3. 5-[(p-Phenoxy)-phenoxymethyl]-3-methylisoxazole.

4. A pesticidal composition containing an effective amount of a (p-phenoxyphenoxy)methyl-five-membered hetaryl of the formula I as set forth in claim 1 together with a suitable carrier.

5. A pesticide as set forth in claim 4, containing from 0.1 to 95 wt% of a (p-phenoxyphenoxy)-methyl-five-membered hetaryl of the formula I.

6. A process for combating pests, wherein the pests, or the areas or spaces to be kept free from pests are treated with a pesticidally effective amount of a (p-phenoxyphenoxy)-methyl-five-membered hetaryl of the formula I as set forth in claim 1.

* * * * *